United States Patent
Cabirol et al.

(10) Patent No.: US 9,803,178 B2
(45) Date of Patent: *Oct. 31, 2017

(54) BIOCATALYSTS FOR THE PREPARATION OF HYDROXY SUBSTITUTED CARBAMATES

(71) Applicant: Codexis, Inc., Redwood City, CA (US)

(72) Inventors: Fabien Louis Cabirol, Dusseldorf (DE); Haibin Chen, Beijing (CN); Anupam Gohel, Bekasi (ID); Steven J. Collier, Concord, MA (US); Derek J. Smith, Singapore (SG); Birgit Kosjek, Westfield, NJ (US); Jacob Janey, New York, NY (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/211,990

(22) Filed: Jul. 15, 2016

(65) Prior Publication Data

US 2016/0319247 A1 Nov. 3, 2016

Related U.S. Application Data

(60) Continuation of application No. 14/825,688, filed on Aug. 13, 2015, now Pat. No. 9,422,531, which is a division of application No. 14/357,964, filed as application No. PCT/US2012/065046 on Nov. 14, 2012, now Pat. No. 9,139,819.

(60) Provisional application No. 61/561,665, filed on Nov. 18, 2011.

(51) Int. Cl.
| | |
|---|---|
| C07H 21/04 | (2006.01) |
| C12N 15/70 | (2006.01) |
| C12N 9/02 | (2006.01) |
| C12N 9/04 | (2006.01) |
| C12P 41/00 | (2006.01) |
| C12P 13/00 | (2006.01) |
| C12P 13/02 | (2006.01) |

(52) U.S. Cl.
CPC ............ *C12N 9/0006* (2013.01); *C12P 13/00* (2013.01); *C12P 13/001* (2013.01); *C12P 13/02* (2013.01); *C12P 41/002* (2013.01); *C12Y 101/01184* (2013.01); *C12N 15/70* (2013.01); *Y02P 20/52* (2015.11)

(58) Field of Classification Search
CPC ...... C12N 9/0006; C12N 15/00; C12N 15/70; C12P 13/00; C12P 13/02; C12Y 101/01184
USPC .... 435/320.1, 252.33, 252.3, 189, 122, 156, 435/69.1, 254.11; 536/23.2
See application file for complete search history.

(56) References Cited

U.S. PATENT DOCUMENTS

| | | | |
|---|---|---|---|
| 5,538,867 | A | 7/1996 | Durliat et al. |
| 5,559,030 | A | 9/1996 | Matsuyama et al. |
| 5,700,670 | A | 12/1997 | Yamagishi et al. |
| 5,846,514 | A | 12/1998 | Foster et al. |
| 5,891,685 | A | 4/1999 | Yamagishi et al. |
| 6,117,679 | A | 9/2000 | Stemmer |
| 6,376,246 | B1 | 4/2002 | Crameri et al. |
| 6,399,339 | B1 | 6/2002 | Wolbert et al. |
| 6,495,023 | B1 | 12/2002 | Zeikus et al. |
| 6,503,921 | B2 | 1/2003 | Naicker et al. |
| 6,537,746 | B2 | 3/2003 | Arnold et al. |
| 6,586,182 | B1 | 7/2003 | Patten et al. |
| 6,613,739 | B1 | 9/2003 | Naicker et al. |
| 6,645,746 | B1 | 11/2003 | Kizaki et al. |
| 6,800,477 | B2 | 10/2004 | Patel et al. |
| 7,705,036 | B2 | 4/2010 | Chou et al. |
| 9,139,819 | B2 | 9/2015 | Cabirol et al. |
| 2005/0095619 | A1 | 5/2005 | Davis et al. |
| 2005/0153417 | A1 | 7/2005 | Davis et al. |
| 2006/0195947 | A1 | 8/2006 | Davis et al. |
| 2006/0286646 | A1 | 12/2006 | Patel et al. |
| 2008/0220990 | A1 | 9/2008 | Fox |
| 2008/0318295 | A1 | 12/2008 | Ching et al. |
| 2009/0093031 | A1 | 4/2009 | Liang et al. |
| 2009/0155863 | A1 | 6/2009 | Liang et al. |
| 2009/0162909 | A1 | 6/2009 | Campopiano et al. |
| 2009/0191605 | A1 | 7/2009 | Liang et al. |
| 2009/0312196 | A1 | 12/2009 | Colbeck et al. |
| 2010/0055751 | A1 | 3/2010 | Voladri et al. |
| 2010/0062499 | A1 | 3/2010 | Mundorff et al. |

FOREIGN PATENT DOCUMENTS

| | | |
|---|---|---|
| WO | 95/22625 A1 | 8/1995 |
| WO | 97/00078 A1 | 1/1997 |
| WO | 97/35966 A1 | 10/1997 |
| WO | 98/27230 A1 | 6/1998 |
| WO | 00/42651 A1 | 7/2000 |
| WO | 00/53731 A2 | 9/2000 |
| WO | 01/40450 A1 | 6/2001 |

(Continued)

OTHER PUBLICATIONS

Altschul, S.F., et al., "Gapped BLAST and PSI-BLAST: a new generation of protein database search programs," Nucleic Acids Res., 25(17):3389-3402 (1997).

(Continued)

*Primary Examiner* — Robert Mondesi
*Assistant Examiner* — Younus Meah
(74) *Attorney, Agent, or Firm* — Codexis, Inc.

(57) ABSTRACT

The present disclosure relates to engineered ketoreductase polypeptides for the preparation of hydroxyl substituted carbamate compounds, and polynucleotides, vectors, host cells, and methods of making and using the ketoreductase polypeptides.

19 Claims, No Drawings

(56) References Cited

FOREIGN PATENT DOCUMENTS

| WO | 01/75767 A2 | 10/2001 |
|---|---|---|
| WO | 2005/018579 A2 | 3/2005 |
| WO | 2005/054491 A1 | 6/2005 |
| WO | 2008/103248 A1 | 8/2008 |
| WO | 2009/008908 A2 | 1/2009 |
| WO | 2009/029554 A2 | 3/2009 |
| WO | 2009/036404 A2 | 3/2009 |
| WO | 2009/042984 A1 | 4/2009 |
| WO | 2009/046153 A1 | 4/2009 |
| WO | 2009/124166 A1 | 10/2009 |
| WO | 2009/124167 A1 | 10/2009 |
| WO | 2010/025085 A1 | 3/2010 |
| WO | 2010/025238 A2 | 3/2010 |
| WO | 2010/025287 A2 | 3/2010 |
| WO | 2010/027710 A2 | 3/2010 |
| WO | 2011/022548 A2 | 2/2011 |
| WO | 2011/140219 A1 | 11/2011 |

OTHER PUBLICATIONS

Altschul, S., et al., "Basic local alignment search tool," J. Mol. Biol., 215: 403-410 (1990).
Beaucage, S.L., et al., "Deoxynucleoside phosphoamidites—A new class of key intermediates for deoxypolynucleotide synthesis," Tetrahedron Letters, 22(20):1859-62 (1981).
Black, M.E., et al., "Creation of drug-specific herpes simplex virus type 1 thymidine kinase mutants for gene therapy," Proc Natl Acad Sci USA, 93:3525-3529 (1996).
Botstein, D., et al., "Strategies and applications of in vitro mutagenesis," Science, 229(4719):1193-1201, 1985.
Broussy, S., et al., "Enantioselective, ketoreductase-based entry into pharmaceutical building blocks: ethanol as tunable nicotinamide reductant," Org Lett., 11(2):305-308 [2009].
Caldwell, R.C., et al., "Mutagenic PCR," PCR Methods Appl., 3:S136-S140 (1994).
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
Henikoff, S., et al., "Amino acid substitution matrices from protein blocks," Proc. Natl. Acad. Sci. USA, 89:10915-10919 [1992].
Hummel, W., et al., "Dehydrogenases for the synthesis of chiral compounds," Eur. J. Biochem., 184:1-13 [1989].
Igawa, Y., et al., "Functional and molecular biological evidence for a possible beta3-adrenoceptor in the human detrusor muscle," Br J Pharmacol. 126(3):819-25 [1999].
Igawa, Y., et al., "Beta3-adrenoceptor agonists: possible role in the treatment of overactive bladder," Korean J Urol., 51:811-818 [2010].
Koszelewski, D., et al., "Immobilization of omega-transaminases by encapsulation in a sol-gel/celite matrix," Journal of Molecular Catalysis B: Enzymatic, 63: 39-44 (2010).
Kramer, B., et al., "Different base/base mismatches are corrected with different efficiencies by the methyl-directed DNA mismatch-repair system of E. coli," Cell, 38(3):879-887, 1984.
Ling, M., et al., "Approaches to DNA Mutagenesis: An Overview," Anal. Biochem., 254:157-78 (1997).
Martin, A.R., et al., "Characterization of free and immobilized (S)-aminotransferase for acetophenone production," Applied Microbiology and Biotechnology, 76(4): 843-851 (2007).
Mateo, C., et al., "Epoxy sepabeads: a novel epoxy support for stabilization of industrial enzymes via very intense multipoint covalent attachment," Biotechnology Progress 18(3):629-34 (2002).
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Puigbo, P., et al., "OPTIMIZER: a web server for optimizing the codon usage of DNA sequences," Nucleic Acids Res., 35 (Web Server issue): W126-31 (2007).
Romanos, M.A., et al., "Foreign gene expression in yeast: a review," Yeast 8:423-488 [1992].
Santaniello, E., et al., "Chiral synthesis of a component of Amanita muscaria, (−)-4-Hydroxypyrrolidin-2-one, and assessment of its absolute confirguration," J. Chem. Res.(S), pp. 132-133 [1984].
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Truppo, M.D., et al., "Development of an Improved Immobilized CAL-B for the Enzymatic Resolution of a Key Intermediate to Odanacatib," Organic Process Research & Development, 15:1033-1035 (2011).
Wells, J.A., et al., "Cassette mutagenesis: an efficient method for generation of multiple mutations at defined sites," Gene, 34:315-323 (1985).
Yi, S., et al., "Covalent immobilization of omega-transaminase from Vibrio fluvialis JS17 on chitosan beads," Process Biochemistry 42(5): 895-898 (2007).
Zhang, J-H., et al., "Directed evolution of a fucosidase from a galactosidase by DNA shuffling and screening," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Zhou, B., et al., "Stereochemical control of yeast reductions. 1. Asymmetric synthesis of L-carnitine," J. Am. Chem. Soc., 105:5925-5926 [1983].

SEQUENCE LISTING

<160> NUMBER OF SEQ ID NOS: 172

<210> SEQ ID NO 1
<211> LENGTH: 756
<212> TYPE: DNA
<213> ORGANISM: Artificial Sequence
<220> FEATURE:
<223> OTHER INFORMATION: Codon-optimized L. kefir ketoreductase gene

<400> SEQUENCE: 1

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag  catcatcaat     420
atgagcagta ttgagggggt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacag                               756
```

<210> SEQ ID NO 2
<211> LENGTH: 252
<212> TYPE: PRT
<213> ORGANISM: Lactobacillus kefir

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Tyr Ile Lys
            180                 185                 190
Thr Pro Leu Val Asp Asp Leu Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 3
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 3

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300
gacactacca cggaggaatg gcgtaaactg ctgtccgtta atctggatgg tgttttttc     360
ggcacccgtc tgggcattca gcgcatgaaa ataaaggct tgggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag                               756
```

<210> SEQ ID NO 4
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 4

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Val
```

```
                85                  90                  95
Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
            130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Met Ser Gln
            195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 5
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 5

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt cgacaccac cgaggaggca     240
ttcggcccgg ttacgaccgt cgtgaacaat gcagggattg ggttcttaa aagcgttgaa     300
gacactacca cggaggaatg cgtaaaactg ctgtccgtta tctggatgg tgttttttc      360
ggcacccgtc tgggcattca gcgcatgaaa ataaaggct tgggcgctag catcatcaat     420
atgagcagta ttttcgggat ggtaggcgat ccgactaccg ggcatacaa cgcttccaag     480
ggggcggtac gtatcatgtc gaaaagcgca gcgctggatt gcgcactgaa ggactacgat     540
gtgcgtgtca acacagtaca tccgggccc atcaagaccc cgatgctcga tgattatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag                               756
```

<210> SEQ ID NO 6
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 6

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 7
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 7

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagta ttttcgggat ggtaggcgat ccgactaccg gggcatacaa cgcttccaag     480 gggcggtac gtatcatgtc gaaaagcgca gcgctggatt gcgcactgaa ggactacgat      540
gtgcgtgtca acacagtaca tccgggcccc atcaagaccc cggctctcga tgattatgaa     600
```

| ggtgctgagg aaatgatgtc acagcgtacg aaaaccccta tgggccacat tggcgaaccg | 660 |
| aatgacatcg catgggtctg tgtgtacctg gcatctgacg aatcgaaatt tgcgacgggt | 720 |
| gcagaatttg tggtcgacgg cgggtggacc gcacag | 756 |

<210> SEQ ID NO 8
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 8

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Ala Leu Asp Asp Tyr Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 9
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 9

| atgaccgatc gtctgaaggg caaagtagcc atcgtaaccg gcgggacact gggtatcggt | 60 |

```
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcaggattg gggttgttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttttcgggat ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaaccccta tgggccacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 10
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 10

```
Met Thr Asp Arg Leu Lys Gly Lys Val Ala Ile Val Thr Gly Gly Thr
 1               5                  10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Trp Thr Ala Gln
            245                 250

<210> SEQ ID NO 11
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 11

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcaggattg gggttcttaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttttcgggat ggtaggcgat ccgactaccg gggcatacaa cgcttccaag   480
ggggcggtac gtatcatgtc gaaaagcgca cgcctggatt cgcactgaa ggactacgat   540
gtgcgtgtca acacagtaca tccgggcccc atcaagaccc cgatgctcga tgattatgaa   600
ggtgctgagg aaatgatgtc acagcgtacg aaaacccccta tgggtcacat ggcgaaccg   660
aatgacatcg catgggtctg tgtgtacctg gcatctgacg aatcgaaatt tgcgacgggt   720
gcagaatttg tggtcgacgg cgggtggacc gcacag                            756
```

<210> SEQ ID NO 12
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 12

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 13
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 13
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttgttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta tttttcggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 14
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 14

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala

```
                50                  55                  60
Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 15
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 15

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg ggttgttaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttttcgggat ggtaggcgat ccgactaccg ggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cggctctcga tgattatgaa    600
ggtgctgagg aaatgatgtc acagcgtacg aaaacccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 16
<211> LENGTH: 252
<212> TYPE: PRT

<213> ORGANISM: Artificial Sequence
<220> FEATURE:
<223> OTHER INFORMATION: Engineered variant of Lactobacillus kefir ketoreductase

<400> SEQUENCE: 16

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Ala Leu Asp Asp Tyr Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 17
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 17

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcaggattc ctgttgttaa aagcgttgaa    300
gacactacca cggaggaatg cgtaaactg ctgtccgtta atctggatgg tgttttttc    360 ggcacccgtc tgggcattca gcgcatgaaa aataaaggct gggcgctag catcatcaat    420
```

```
atgagcagta ttttcgggat ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaaacccta tgggtcacat ggcgaaccg     660 aatgacatcg catgggtctg tgtgtacctg gcatctgacg aatcgaaatt tgcgacgggt    720
gcagaatttg tggtcgacgg cgggtggacc gcacag                              756
```

```
<210> SEQ ID NO 18
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 18
```

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

```
<210> SEQ ID NO 19
<211> LENGTH: 756
<212> TYPE: DNA
<213> ORGANISM: Artificial Sequence
<220> FEATURE:
<223> OTHER INFORMATION: Engineered variant of Lactobacillus kefir
``` ketoreductase

<400> SEQUENCE: 19

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gatggttaa aagcgttgaa      300
gacactacca cggaggaatg gcgtaaactg ctgtccgtta atctggatgg tgttttttc      360
ggcacccgtc tgggcattca gcgcatgaaa aataaaggct tgggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat ggcgaaccg      660
aatgacatcg catgggtctg tgtgtacctg gcatctgacg aatcgaaatt tgcgacgggt     720
gcagaatttg tggtcgacgg cgggtggacc gcacag                                756
```

<210> SEQ ID NO 20
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 20

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Met Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp Tyr Glu Gly Ala Glu Glu Met Phe Ser Gln
        195                 200                 205
```

```
Arg Thr Lys Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
            245                 250

<210> SEQ ID NO 21
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 21
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg gggttgttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagtg ttttcgggat ggtaggcgat ccgactaccg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgattatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtggacc gcacag                             756

<210> SEQ ID NO 22
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 22

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110
```

Val Asn Leu Asp Gly Val Phe Phe Gly Thr Arg Leu Gly Ile Gln Arg
         115                 120                 125

Met Lys Asn Lys Gly Leu Gly Ala Ser Ile Ile Asn Met Ser Ser Val
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 23
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 23
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttgttaa aagcgttgaa     300
gacactacca cggaggaatg gcgtaaactg ctgtccgtta atctggatgg tgttttttc      360 ggcacccgtc tgggcattca gcgcatgaaa ataaaggct gggcgctag catcatcaat      420 atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                                756

<210> SEQ ID NO 24
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 24

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala

```
            20                  25                  30
Lys Val Val Ile Thr Gly Arg Arg Ala Asp Val Gly Glu Lys Ala Ala
         35                  40                  45
Lys Ser Ile Gly Gly Thr Asp Val Ile Arg Phe Val Gln His Asp Ala
     50                  55                  60
Ser Asp Glu Ala Gly Trp Thr Lys Leu Phe Asp Thr Thr Glu Glu Ala
 65                  70                  75                  80
Phe Gly Pro Val Thr Thr Val Val Asn Asn Ala Gly Ile Gly Val Val
                 85                  90                  95
Lys Ser Val Glu Asp Thr Thr Thr Glu Glu Trp Arg Lys Leu Leu Ser
                100                 105                 110
Val Asn Leu Asp Gly Val Phe Phe Gly Thr Arg Leu Gly Ile Gln Arg
            115                 120                 125
Met Lys Asn Lys Gly Leu Gly Ala Ser Ile Ile Asn Met Ser Ser Ile
        130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
                180                 185                 190
Thr Pro Met Met Asp Asp Tyr Glu Gly Ala Glu Met Phe Ser Gln
            195                 200                 205
Arg Thr Lys Thr Pro Met Gly His Ile Gly Glu Pro Asn Asp Ile Ala
        210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250

<210> SEQ ID NO 25
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 25
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc      180 cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc      360 ggcacccgtc tgggcattca gcgcatgaaa aataaaggct ggggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga ttcgtatgaa     600
ggtgctgagg aaatgttttc acagcgtacg aaaacccccta tgggtcacat tggcgaaccg     660
aatgacatcg catgggtctg tgtgtacctg gcatctgacg aatcgaaatt tgcgacgggt     720
```
gcagaatttg tggtcgacgg cgggtggacc gcacag       756

<210> SEQ ID NO 26
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 26

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Ser Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 27
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 27
atgaccgatc gtctgaaggg caaagtagcc atcgtaaccg gcgggacact gggtatcggt       60
ttggcaatcg ccgataaatt tgtagaggag ggtgcgaaag tagttattac tggtcgtcgt      120
gcggatgtag gtgaaaaggc cgccaaatca atcggcggca ctgatgttat tcgctttgtc      180
cagcacgatg tttccgatga agcaggctgg acgaaactgt tcgacaccac cgaggaggca      240

```
ttcggcccgg ttacgacctt agtgaacaat gcagggattg gggttgttaa aagcgttgaa        300
gacactacca cggaggaatg gcgtaaactg ctgtccgtta atctggatgg tgttttttc         360 ggcacccgtc tgggcattca gcgcatgaaa aataaaggct tgggcgctag catcatcaat       420
atgagcagta ttttcgggca ggtaggcgat ccgactaccg gggcatacaa cgcttccaag       480
ggggcggtac gtatcatgtc gaaaagcgca gcgctggatt gcgcactgaa ggactacgat       540
gtgcgtgtca acacagtaca tccgggcccc atcaagaccc cgatgctcga tgatcatgaa       600
ggtgctgagg aaatgttttc acagcgtacg aaaaccccta tgggtcacat tggcgaaccg       660
aatgacatcg catgggtctg tgtgtacctg gcatctgacg aatcgaaatt tgcgacgggt       720
gcagaatttg tggtcgacgg cgggtggacc gcacag                                 756
```

<210> SEQ ID NO 28
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 28

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 29
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 29

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgaccgt cgtgaacaat gcagggattg ggttgttaa aagcgttgaa      300
gacactacca cggaggaatg gcgtaaactg ctgtccgtta atctggatgg tgttttttc     360
ggcacccgtc tgggcattca gcgcatgaaa aataaaggct tgggcgctag catcatcaat     420
atgagcagta ttttcgggca ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                                756
```

<210> SEQ ID NO 30
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 30

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Pro Ile Lys
            180                 185                 190

Thr Pro Met Leu Asp Asp His Glu Gly Ala Glu Met Phe Ser Gln
        195                 200                 205

Arg Thr Lys Thr Pro Met Gly His Ile Gly Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

```
<210> SEQ ID NO 31
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 31
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggattcc ggttgttaa aagcgttgaa      300 gacactacca cggaggaatg cgtaaactg ctgtccgtta atctggatgg tgtttttttc      360
ggcacccgtc tgggcattca gcgcatgaaa aataaaggct gggcgctag catcatcaat     420 atgagcagtg tgttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756
```

```
<210> SEQ ID NO 32
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 32

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80
```

Phe Gly Pro Val Thr Thr Val Val Asn Asn Ala Gly Ile Pro Val Val
            85                  90                  95

Lys Ser Val Glu Asp Thr Thr Thr Glu Glu Trp Arg Lys Leu Leu Ser
        100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 33
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 33
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaagca     240
ttcggcccgg ttacgaccgt agtgaacaat gcaggattcc gatggttaa aagcgttgaa     300 gacactacca cggaggaatg cgtaaactg ctgtccgtta atctggatgg tgttttttc     360 ggcgcccgtc tgggcattca gcgcatgaaa aataaaggct gggcgctag catcatcaat     420 atgagcagtg tgttcgggat gtaggcgac ccgactaccg gggcatactg tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tagctatgaa     600
ggtgctgagg aaatgttttc acagcgtacg aaaacccta tgggtcacat tggcgaaccg     660
aatgacatcg catgggtctg tgtgtacctg gcatctgacg aatcgaaatt tgcgacgggt     720
gcagaatttg tggtcgacgg cgggtacacc gcacag                               756

<210> SEQ ID NO 34
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 34

```
Met Thr Asp Arg Leu Lys Gly Lys Val Ala Ile Val Thr Gly Thr
1               5                   10                  15
Gln Gly Ile Gly Leu Ala Ile Ala Asp Lys Phe Val Glu Glu Gly Ala
                20                  25                  30
Lys Val Val Ile Thr Gly Arg Arg Ala Asp Val Gly Glu Lys Ala Ala
            35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Met Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Ala Arg Leu Gly Ile Gln Arg
        115                 120                 125
Met Lys Asn Lys Gly Leu Gly Ala Ser Ile Ile Asn Met Ser Ser Val
130                 135                 140
Phe Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Ser Tyr Glu Gly Ala Glu Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 35
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 35

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgttcgggat tgtaggcgac ccgactaccg ggcatactg tgcttccaag      480
ggggcggtac gtatcatgtc gaaaagcgca gcgctggatt gcgcactgaa ggactacgat      540
```

```
gtgcgtgtca acacagtaca tccgggcccc atcaagaccc cgatgatgga tgattatgaa      600
ggtgctgagg aaatgttttc acagcgtacg aaaacccta tgggtcacat tggcgaaccg        660
aatgacatcg catgggtctg tgtgtacctg gcatctgacg aatcgaaatt tgcgacgggt      720
gcagaatttg tggtcgacgg cgggttcacc gcacag                                756
```

<210> SEQ ID NO 36
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 36

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 37
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 37

```
atgaccgatc gtctgaaggg caaagtagcc atcgtaaccg gcgggacaat gggtatcggt      60
```

```
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg actaaactgt tcgacaccac cgaggaagca    240
ttcggcccgg ttacgacctt agtgaacaat gcaggggattc cggttgttaa aagcgttgaa    300
gacactacca cggaggaatg gcgtaaactg ctgtccgtta atctggatgg tgttttttc    360 ggcacccgtc tgggcattca gcgcatgaaa aataaaggct tgggcgctag catcatcaat    420
atgagcagtg tgttcgggat ggtaggcgac ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccc atcaagaccc cgatgatgga tagccatgaa    600
ggtgctgagg aaatgttttc acagcgtacg aaaacccta tgggtcacat tggcgaaccg    660
aatgacatcg catgggtctg tgtgtacctg gcatctgacg aatcgaaatt tgcgacgggt    720
gcagaatttg tggtcgacgg cgggttcacc gcacag                              756
```

<210> SEQ ID NO 38
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 38

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Met Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser His Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
```

```
                225                 230                 235                 240
Ala Glu Phe Val Val Asp Gly Gly Phe Thr Ala Gln
                    245                 250

<210> SEQ ID NO 39
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 39
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg actaaactgt tcgacaccac cgaggaggca     240
ttcggcccgg ttacgacctt agtgaacaat gcagggattc cggttgttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgttcgggat tgtaggctac ccgactaccg gggcatactg tgcttccaag     480
ggagcggtac gtatcatgtc gaaaagcgca gcgctggatt gcgcactgaa ggactacgat     540
gtgcgtgtca acacagtaca tccgggcccc atcaagaccc cgatgatgga tagctatgaa     600
ggtgctgagg aaatgttttc acagcgtacg aaaacccta tgggtcacat ggcgaaccg      660 aatgacatcg catgggtctg tgtgtacctg gcatctgacg aatcgaaatt tgcgacgggt     720
gcagaatttg tggtcgacgg cgggtggacc gcacag                                756

<210> SEQ ID NO 40
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 40

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140
```

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 41
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 41
atgaccgatc gtctgaaggg caaagtagcc atcgtaaccg gcgggacaca aggtatcggt      60
ttggcagtcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt cgacaccac cgaggaggca     240 ttcggcccgg ttacgacctt agtgaacaat gcagggattc cgatggttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgttcgggat tgtaggcgac ccgactggtg gggcatactg tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tagctatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggttcacc gcacag                              756

<210> SEQ ID NO 42
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 42

Met Thr Asp Arg Leu Lys Gly Lys Val Ala Ile Val Thr Gly Gly Thr
1               5                   10                  15

Gln Gly Ile Gly Leu Ala Val Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
50                  55                  60

Ser Asp Glu Ala Gly Trp Pro Lys Leu Phe Asp Thr Thr Glu Ala
65                  70                  75                  80

Phe Gly Pro Val Thr Thr Leu Val Asn Asn Ala Gly Ile Pro Met Val
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Phe Gly Ile Val Gly Asp Pro Thr Gly Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Ser Tyr Glu Gly Ala Glu Glu Met Phe Ser Gln
                195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 43
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 43
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cgatggttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagtg tgttcgggat ggtaggctac ccgactaccg gggcatacaa tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tagctatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 44
<211> LENGTH: 252

<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 44

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Met Val Gly Tyr Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 45
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 45
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg gggtttataa aagcgttgaa   300
gacactacca cggaggaatg gcgtaaactg ctgtccgtta atctggatgg tgttttttc   360

```
ggcacccgtc tgggcattca gcgcatgaaa aataaaggct tgggcgctag catcatcaat      420
atgagcagta ttttcgggat ggtaggcgat ccgactaccg gggcatacaa cgcttccaag      480
ggggcggtac gtatcatgtc gaaaagcgca gcgctggatt gcgcactgaa ggactacgat      540
gtgcgtgtca acacagtaca tccgggcccc atcaagaccc cgatgctcga tgattatgaa      600
ggtgctgagg aaatgatgtc acagcgtacg aaaacccta tgggccacat tggcgaaccg       660
aatgacatcg catgggtctg tgtgtacctg gcatctgacg aatcgaaatt tgcgacgggt      720
gcagaatttg tggtcgacgg cgggtggacc gcacag                                756
```

<210> SEQ ID NO 46
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 46

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 47
<211> LENGTH: 756
<212> TYPE: DNA
<213> ORGANISM: Artificial Sequence
<220> FEATURE:

<223> OTHER INFORMATION: Engineered variant of Lactobacillus kefir
ketoreductase

<400> SEQUENCE: 47

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat cgctttgtc      180
cagcacgatg cgtccgatga agcaggctgg acgaaactgt tcgacaccac cgaggaggca     240
ttcggcccgg ttacgaccgt cgtgaacaat gcagggattg ggttgttaa agcgttgaa       300
gacactacca cggaggaatg gcgtaaactg ctgtccgtta atctggatgg tgtttttttc     360
ggcacccgtc tgggcattca gcgcatgaaa aataaaggct gggcgctag catcatcaat      420
atgagcagta ttttggggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag                               756
```

<210> SEQ ID NO 48
<211> LENGTH: 252
<212> TYPE: PRT
<213> ORGANISM: Artificial Sequence
<220> FEATURE:
<223> OTHER INFORMATION: Engineered variant of Lactobacillus kefir
ketoreductase

<400> SEQUENCE: 48

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Leu Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Met Ser Gln
```

```
                       195                 200                 205
Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 49
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 49
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttgttaa agcgttgaa      300
gacactacca cggaggaatg gcgtaaactg ctgtccgtta atctggatgg tgttttttc      360
ggcacccgtc tgggcattca gcgcatgaaa ataaaggct tgggcgctag catcatcaat      420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cggggctcga tgattatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 50
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 50

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110
```

```
Val Asn Leu Asp Gly Val Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Gly Leu Asp Asp Tyr Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 51
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 51
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggattg gggttgttaa aagcgttgaa      300
gacactacca cggaggaatg gcgtaaactg ctgtccgtta tctggatgg tgtttttttc      360 ggcacccgtc tgggcattca gcgcatgaaa aataaaggct ggggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 52
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 52

Met Thr Asp Arg Leu Lys Gly Lys Val Ala Ile Val Thr Gly Gly Thr
1               5                   10                  15
```

Leu Gly Ile Gly Leu Ala Ile Ala Asp Lys Phe Val Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Leu Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 53
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 53
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggattgg ggttgttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttttcgggat ggtaggcgat ccgactaccg ggcatacaa cgcttccaag      480 ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacag 756

<210> SEQ ID NO 54
<211> LENGTH: 252
<212> TYPE: PRT
<213> ORGANISM: Artificial Sequence
<220> FEATURE:
<223> OTHER INFORMATION: Engineered variant of Lactobacillus kefir
       ketoreductase

<400> SEQUENCE: 54

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp His Glu Gly Ala Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 55
<211> LENGTH: 756
<212> TYPE: DNA
<213> ORGANISM: Artificial Sequence
<220> FEATURE:
<223> OTHER INFORMATION: Engineered variant of Lactobacillus kefir
       ketoreductase

<400> SEQUENCE: 55
atgaccgatc gtctgaaggg caaagtagcc atcgtaaccg gcgggacaca gggtatcggt    60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180

```
cagcacgatg cgtccgatga agcaggctgg acgaaactgt tcgacaccac cgaggaggca    240
ttcggcccgg ttacgaccgt cgtgaacaat gcaggattg gggttgttaa aagcgttgaa    300
gacactacca cggaggaatg gcgtaaactg ctgtccgtta atctggatgg tgttttttttc  360 ggcacccgtc tgggcattca gcgcatgaaa aataaaggct tgggcgctag catcatcaat   420
atgagcagta ttttcgggat ggtaggcgat ccgactaccg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgattatgaa   600
ggtgctgagg aaatgttttc acagcgtacg aaaacccct tgggtcacat ggcgaaccg     660 aatgacatcg catgggtctg tgtgtacctg gcatctgacg aatcgaaatt tgcgacgggt   720
gcagaatttg tggtcgacgg cgggtggacc gcacag                              756
```

```
<210> SEQ ID NO 56
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 56
```

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 57
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 57

```
atgaccgatc gtctgaaggg caaagtagcc atcgtaaccg gcgggacacg gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggggattg gggttgttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat ggcgaaccg     660
aatgacatcg catgggtctg tgtgtacctg gcatctgacg aatcgaaatt tgcgacgggt     720
gcagaatttg tggtcgacgg cgggtggacc gcacag                              756
```

<210> SEQ ID NO 58
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 58

```
Met Thr Asp Arg Leu Lys Gly Lys Val Ala Ile Val Thr Gly Gly Thr
  1               5                  10                  15

Arg Gly Ile Gly Leu Ala Ile Ala Asp Lys Phe Val Glu Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Ala
     50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
```

```
                165                 170                 175
Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
            195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
            245                 250

<210> SEQ ID NO 59
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 59
atgaccgatc gtctgaaggg caaagtagcc atcgtaaccg gcgggacact gggtatcggt      60
ttggcaatcg ccgataaatt tgtaggggag ggtgcgaaag tagttattac tggtcgtcgt     120
gcggatgtag gtgaaaaggc cgccaaatca atcggcggca ctgatgttat cgctttgtc      180 cagcacgatg cgtccgatga agcaggctgg cctaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                               756

<210> SEQ ID NO 60
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 60

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Gly Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Pro Lys Leu Phe Asp Thr Thr Glu Glu Ala
65                  70                  75                  80
```

```
Phe Gly Pro Val Thr Thr Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp Tyr Glu Gly Ala Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 61
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 61

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattc tgttgttaa aagcgttgaa     300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttttcgggat ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaacccta tggtcacat ggcgaaccg      660
aatgacatcg catgggtctg tgtgtacctg gcatctgacg aatcgaaatt tgcgacgggt   720
gcagaatttg tggtcgacgg cgggtggacc gcacag                              756
```

<210> SEQ ID NO 62
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase -continued

<400> SEQUENCE: 62

| | | | | | | | | | | | | | | |
|---|---|---|---|---|---|---|---|---|---|---|---|---|---|---|
| Met | Thr | Asp | Arg | Leu | Lys | Gly | Lys | Val | Ala | Ile | Val | Thr | Gly | Thr |
| 1 | | | | 5 | | | | | 10 | | | | | 15 |
| Leu | Gly | Ile | Gly | Leu | Ala | Ile | Ala | Asp | Lys | Phe | Val | Glu | Glu | Gly | Ala |
| | | | 20 | | | | | 25 | | | | | 30 | | |
| Lys | Val | Val | Ile | Thr | Gly | Arg | Arg | Ala | Asp | Val | Gly | Glu | Lys | Ala | Ala |
| | | | 35 | | | | | 40 | | | | | 45 | | |
| Lys | Ser | Ile | Gly | Gly | Thr | Asp | Val | Ile | Arg | Phe | Val | Gln | His | Asp | Ala |
| | 50 | | | | | 55 | | | | | 60 | | | | |
| Ser | Asp | Glu | Ala | Gly | Trp | Thr | Lys | Leu | Phe | Asp | Thr | Thr | Glu | Glu | Ala |
| 65 | | | | | 70 | | | | | 75 | | | | | 80 |
| Phe | Gly | Pro | Val | Thr | Thr | Val | Val | Asn | Asn | Ala | Gly | Ile | Ala | Val | Val |
| | | | | 85 | | | | | 90 | | | | | 95 | |
| Lys | Ser | Val | Glu | Asp | Thr | Thr | Thr | Glu | Glu | Trp | Arg | Lys | Leu | Leu | Ser |
| | | | | 100 | | | | | 105 | | | | | 110 | |
| Val | Asn | Leu | Asp | Gly | Val | Phe | Phe | Gly | Thr | Arg | Leu | Gly | Ile | Gln | Arg |
| | | | | 115 | | | | | 120 | | | | | 125 | |
| Met | Lys | Asn | Lys | Gly | Leu | Gly | Ala | Ser | Ile | Ile | Asn | Met | Ser | Ser | Ile |
| | | 130 | | | | | 135 | | | | | 140 | | | |
| Phe | Gly | Met | Val | Gly | Asp | Pro | Thr | Thr | Gly | Ala | Tyr | Asn | Ala | Ser | Lys |
| 145 | | | | | 150 | | | | | 155 | | | | | 160 |
| Gly | Ala | Val | Arg | Ile | Met | Ser | Lys | Ser | Ala | Leu | Asp | Cys | Ala | Leu |
| | | | | 165 | | | | | 170 | | | | | 175 |
| Lys | Asp | Tyr | Asp | Val | Arg | Val | Asn | Thr | Val | His | Pro | Gly | Pro | Ile | Lys |
| | | | 180 | | | | | 185 | | | | | 190 | | |
| Thr | Pro | Met | Leu | Asp | Asp | Tyr | Glu | Gly | Ala | Glu | Glu | Met | Phe | Ser | Gln |
| | | | | 195 | | | | | 200 | | | | | 205 | |
| Arg | Thr | Lys | Thr | Pro | Met | Gly | His | Ile | Gly | Glu | Pro | Asn | Asp | Ile | Ala |
| | | 210 | | | | | 215 | | | | | 220 | | | |
| Trp | Val | Cys | Val | Tyr | Leu | Ala | Ser | Asp | Glu | Ser | Lys | Phe | Ala | Thr | Gly |
| 225 | | | | | 230 | | | | | 235 | | | | | 240 |
| Ala | Glu | Phe | Val | Val | Asp | Gly | Gly | Trp | Thr | Ala | Gln |
| | | | | 245 | | | | | 250 | | |

<210> SEQ ID NO 63
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 63

| | |
|---|---|
| atgaccgatc gtctgaaggg caaagtagcc atcgtaaccg gcgggacact gggtatcggt | 60 |
| ttggcaatcg ccgataaatt tgtagaggag ggtgcgaaag tagttattac tggtcgtcgt | 120 |
| gcggatgtag gtgaaaaggc cgccaaatca atcggcggca ctgatgttat tcgctttgtc | 180 |
| cagcacgatg cgtccgatga agcaggctgg acgaaactgt tcgacaccac cgaggaggca | 240 |
| ttcggcccgg ttacgaccgt cgtgaacaat gcaggattat gttgttaa aagcgttgaa | 300 |
| gacactacca cggaggaatg gcgtaaactg ctgtccgtta atctggatgg tgtttttttc | 360 |
| ggcacccgtc tgggcattca gcgcatgaaa aataaaggct gggcgctag catcatcaat | 420 |
| atgagcagta ttttcgggat ggtaggcgat ccgactaccg ggcatacaa cgcttccaag | 480 |
| ggggcggtac gtatcatgtc gaaaagcgca gcgctggatt gcgcactgaa ggactacgat | 540 |

```
gtgcgtgtca acacagtaca tccgggcccc atcaagaccc cgatgctcga tgattatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 64
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 64

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 65
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 65

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg gggttgttaa aagcgttgaa   300
gacactacca cggaggaatg gcgtaaactg ctgtccgtta atctggatgg tgttttttc    360 ggcacccgtc tgggcattca gcgcatgaaa agtaaaggct gggcgctag catcatcaat   420 atgagcagta ttttcgggat ggtaggcgat ccgactaccg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgattatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtggacc gcacag                             756
```

<210> SEQ ID NO 66
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 66

```
Met Thr Asp Arg Leu Lys Gly Lys Val Ala Ile Val Thr Gly Gly Thr
 1               5                  10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Ser Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220
```

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 67
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 67

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttgttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttttcgggat ggtaggctat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat ggcgaaccg     660
aatgacatcg catgggtctg tgtgtacctg gcatctgacg aatcgaaatt tgcgacgggt     720
gcagaatttg tggtcgacgg cgggtggacc gcacag                               756
```

<210> SEQ ID NO 68
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 68

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile

Phe Gly Met Val Gly Tyr Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 69
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 69
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc      180 cagcacgatg cgtccgatga agcaggctgg acgaaactgt cgacaccac cgaggaggca      240 ttcggcccgg ttacgaccgt cgtgaacaat gcagggattg gggttgttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttttcgggat ggtaggcgat ccggggaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 70
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 70

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Phe Gly Met Val Gly Asp Pro Gly Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Leu Asp Asp Tyr Glu Gly Ala Glu Met Phe Ser Gln
            195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

```
<210> SEQ ID NO 71
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 71
atgaccgatc gtctgaaggg caaagtagcc atcgtaaccg cgggacact  gggtatcggt      60 ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa  aagcgttgaa     300 gacactacca cggaggaatg gcgtaaactg ctgtccgtta atctggatgg tgttttttc     360 ggcacccgtc tgggcattca gcgcatgaaa aataaaggct gggcgctag  catcatcaat     420 atgagcagta ttttcgggat ggtaggcgat ccgactaccg gggcatactg tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tggtcacat  tggcgaaccg     660 aatgacatcg catgggtctg tgtgtacctg gcatctgacg aatcgaaatt tgcgacgggt     720
gcagaatttg tggtcgacgg cgggtggacc gcacag                                756

<210> SEQ ID NO 72
```

<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 72

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 73
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 73

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg cgtaaactg ctgtccgtta atctggatgg tgttttttc      360
```

```
ggcacccgtc tgggcattca gcgcatgaaa aataaaggct tgggcgctag catcatcaat    420
atgagcagta ttttcgggat ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgggtctcga tgattatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 74
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase
<400> SEQUENCE: 74

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Gly Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 75
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 75

| | | | | | |
|---|---|---|---|---|---|
| atgaccgatc | gtctgaaggg | caaagtagcc | atcgtaaccg | gcgggacact | gggtatcggt | 60 |
| ttggcaatcg | ccgataaatt | tgtagaggag | ggtgcgaaag | tagttattac | tggtcgtcgt | 120 |
| gcggatgtag | gtgaaaaggc | cgccaaatca | atcggcggca | ctgatgttat | tcgctttgtc | 180 |
| cagcacgatg | cgtccgatga | agcaggctgg | acgaaactgt | tcgacaccac | cgaggaggca | 240 |
| ttcggcccgg | ttacgaccgt | cgtgaacaat | gcagggattg | gggttgttaa | aagcgttgaa | 300 |
| gacactacca | cggaggaatg | gcgtaaactg | ctgtccatta | atctggatgg | tgtttttttc | 360 |
| ggcacccgtc | tgggcattca | gcgcatgaaa | aataaaggct | tgggcgctag | catcatcaat | 420 |
| atgagcagta | ttttcgggat | ggtaggcgat | ccgactaccg | gggcatacaa | cgcttccaag | 480 |
| ggggcggtac | gtatcatgtc | gaaaagcgca | gcgctggatt | gcgcactgaa | ggactacgat | 540 |
| gtgcgtgtca | acacagtaca | tccgggcccc | atcaagaccc | cgatgcttga | tgattatgaa | 600 |
| ggtgctgagg | aaatgttttc | acagcgtacg | aaaaccccta | tgggtcacat | tggcgaaccg | 660 |
| aatgacatcg | catgggtctg | tgtgtacctg | gcatctgacg | aatcgaaatt | tgcgacgggt | 720 |
| gcagaatttg | tggtcgacgg | cgggtggacc | gcacag | | | 756 |

<210> SEQ ID NO 76
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 76

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Ile Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 77
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 77
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcaggggattg gggttgttaa aagcgttgaa    300
gacactacca cggaggaatg gcgtaaactg ctgtccgtta atctggatgg tgttttttc    360 ggcacccgtc tgggcattca gcgcatgaaa aataaaggct tgggcgctag catcatcaat    420
atgagcagta ttttcgggat ggtaggcgat ccgactaccg gggcatacaa cgcttccaag    480
ggggcggtac gtatcatgtc gaaaagcgca cgcgtggatt cgcactgaa ggactacgat    540 gtgcgtgtca acacagtaca tccgggcccc atcaagaccc cgatgatgga tgattatgaa    600
ggtgctgagg aaatgttttc acagcgtacg aaaaacccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756

<210> SEQ ID NO 78
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 78

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser

```
                100                 105                 110
Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 79
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 79

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggattgg ggttgttaa aagcgttgaa      300
gacactacca cggaggaatg cgtaaactg ctgtccgtta atctggatgg tgttttttc       360
ggcacccgtc tgggcattca gcgcatgaaa ataaaggct tgggcgctag catcatcaat      420
atgagcagta ttttcgggat ggtaggcgat ccgactaccg ggcatacaa cgcttccaag      480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cggggtacc gcacag                                756
```

<210> SEQ ID NO 80
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 80

```
Met Thr Asp Arg Leu Lys Gly Lys Val Ala Ile Val Thr Gly Gly Thr
1               5                   10                  15
```

```
Leu Gly Ile Gly Leu Ala Ile Ala Asp Lys Phe Val Glu Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Ala
     50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Thr Ala Gln
                245                 250
```

<210> SEQ ID NO 81
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 81

```
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgacctt agtgaacaat gcagggattg ggtttacaa agcgttgaa      300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttttcgggct ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgttttc acagcgtacg aaaaccccta tgggtcacat tggcgaaccg     660
```

```
aatgacatcg catgggtctg tgtgtacctg gcatctgacg aatcgaaatt tgcgacgggt    720
gcagaatttg tggtcgacgg agggtggacc gcacag                             756
```

<210> SEQ ID NO 82
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 82

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Leu Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 83
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 83

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
```

```
cagcacgatg cgtccgatga agcaggctgg acgaaactgt tcgacaccac cgaggaggca    240
ttcggcccgg ttacgacctt agtgaacaat gcagggattg gggttgttaa aagcgttgaa    300
gacactacca cggaggaatg gcgtaaactg ctgtccgtta atctggatgg tgttttttc     360 ggcacccgtc tgggcattca cgcatgaaa aataaaggct tgggcgctag catcatcaat     420
atgagcagta ttttcgggct ggtaggcgat ccgactaccg gggcatacaa cgcttccaag    480
ggggcggtac gtatcatgtc gaaaagcgca gcgctgttat gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

```
<210> SEQ ID NO 84
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 84
```

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Leu Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 85
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 85

```
atgaccgatc gtctgaaggg caaagtagcc atcgtaaccg gcgggacaat gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tttccgatga agcaggctgg acgaaactgt tcgacaccac cgaggaggca    240
ttcggcccgg ttacgacctt agtgaacaat gcagggattg gggttgttaa aagcgttgaa    300
gacactacca cggaggaatg gcgtaaactg ctgtccgtta atctggatgg tgttttttc     360
ggcacccgtc tgggcattca gcgcatgaaa aataaaggct gggcgctag catcatcaat    420
atgagcagta ttttcgggca ggtaggcgat ccgactaccg gggcatacaa cgcttccaag    480
ggggcggtac gtatcatgtc gaaaagcgca gcgctgttat gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat ggcgaaccg     660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 86
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 86

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160
```

Gly Ala Val Arg Ile Met Ser Lys Ser Ala Leu Leu Cys Ala Leu
            165                 170                 175

Lys Asp Tyr Asp Val Arg Val Asn Thr Val His Pro Gly Pro Ile Lys
        180                 185                 190

Thr Pro Met Leu Asp Asp His Glu Gly Ala Glu Glu Met Phe Ser Gln
    195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 87
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 87
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgacctt agtgaacaat gcagggattg gggttctgaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                                 756

<210> SEQ ID NO 88
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 88

Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala

```
            65                  70                  75                  80
        Phe Gly Pro Val Thr Thr Leu Val Asn Asn Ala Gly Ile Gly Val Leu
                        85                  90                  95

Lys Ser Val Glu Asp Thr Thr Glu Glu Trp Arg Lys Leu Leu Ser
                    100                 105                 110

Val Asn Leu Asp Gly Val Phe Phe Gly Thr Arg Leu Gly Ile Gln Arg
                    115                 120                 125

Met Lys Asn Lys Gly Leu Gly Ala Ser Ile Ile Asn Met Ser Ser Ile
                    130                 135                 140

Phe Gly Met Val Gly Asp Pro Thr Thr Gly Ala Tyr Asn Ala Ser Lys
        145                 150                 155                 160

Gly Ala Val Arg Ile Met Ser Lys Ser Ala Ala Leu Asp Cys Ala Leu
                        165                 170                 175

Lys Asp Tyr Asp Val Arg Val Asn Thr Val His Pro Gly Pro Ile Lys
                    180                 185                 190

Thr Pro Met Leu Asp Asp His Glu Gly Ala Glu Glu Met Phe Ser Gln
                    195                 200                 205

Arg Thr Lys Thr Pro Met Gly His Ile Gly Glu Pro Asn Asp Ile Ala
                    210                 215                 220

Trp Val Cys Val Tyr Leu Ala Ser Asp Glu Ser Lys Phe Ala Thr Gly
        225                 230                 235                 240

Ala Glu Phe Val Val Asp Gly Gly Trp Thr Ala Gln
                        245                 250

<210> SEQ ID NO 89
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 89
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtctgatga agcaggctgg acgaaactgt tcgacaccac cgaggaggca     240
ttcggcccgg ttacgaccgt cgtgaacaat gcagggattg gggttctgaa agcgttgaa      300 gacactacca cggaggaatg gcgtaaactg ctgtccgtta atctggatgg tgttttttc      360 ggcacccgtc tgggcattca cgcatgaaa ataaaggct tgggcgctag catcatcaat       420
atgagcagta ttttcgggca ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756

<210> SEQ ID NO 90
<211> LENGTH: 252
<212> TYPE: PRT
<213> ORGANISM: Artificial Sequence
<220> FEATURE:
<223> OTHER INFORMATION: Engineered variant of Lactobacillus kefir
``` ketoreductase

<400> SEQUENCE: 90

```
Met Thr Asp Arg Leu Lys Gly Lys Val Ala Ile Val Thr Gly Gly Thr
1               5                   10                  15
Met Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Leu
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Gln Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp Tyr Glu Gly Ala Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 91
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 91

```
atgaccgatc gtctgaaggg caaagtagcc atcgtaaccg gcgggacaat gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tttccgatga agcaggctgg acgaaactgt tcgacaccac cgaggaggca    240
ttcggcccgg ttacgacctt agtgaacaat gcagggattg ggtttacaa agcgttgaa      300
gacactacca cggaggaatg gcgtaaactg ctgtccgtta atctggatgg tgttttttc     360
ggcacccgtc tgggcattca gcgcatgaaa aataaaggct gggcgctag catcatcaat    420
atgagcagta ttttcgggca ggtaggcgat ccgactaccg gggcatacaa cgcttccaag    480
```

```
ggggcggtac gtatcatgtc gaaaagcgca gcgctggatt gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccca tgggtcacat ggcgaaccg     660 aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 92
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 92

```
Met Thr Asp Arg Leu Lys Gly Lys Val Ala Ile Val Thr Gly Gly Thr
1               5                  10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 93
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 93

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgacctt agtgaacaat gcagggattg gggttctgaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagta ttttcgggca ggtaggcgat ccgactaccg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgatgctcga tgatcatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtggacc gcacag                             756
```

<210> SEQ ID NO 94
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 94

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220
```

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
            245                 250

<210> SEQ ID NO 95
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 95

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttctgaa aagcgttgaa     300
gacactacca cggaggaatg gcgtaaactg ctgtccgtta tctggatgg tgttttttc       360
ggcacccgtc tgggcattca gcgcatgaaa aataaaggct tgggcgctag catcatcaat     420
atgagcagta ttttcgggca gtaggcgat ccgactaccg gggcatacaa cgcttccaag      480
ggggcggtac gtatcatgtc gaaaagcgca gcgctgttat gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                              756
```

<210> SEQ ID NO 96
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 96

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
            130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 97
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 97
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt cgacaccac cgaggaggca     240 ttcggcccgg ttacgaccgt cgtgaacaat gcagggattg gggttgttaa aagcgttgaa     300
gacactacca cggaggaatg cgtaaactg ctgtccgtta atctggatgg tgttttttc      360 ggcacccgtc tgggcattca gcgcatgaaa aataaaggct tgggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgatcacgaa     600
ggtgctgagg aaatgttttc acagcgtacg aaaacccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                               756

<210> SEQ ID NO 98
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 98

Met Thr Asp Arg Leu Lys Gly Lys Val Ala Ile Val Thr Gly Gly Thr
1                 5                 10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala

```
                35                  40                  45
Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Ile
                130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Leu Asp Asp His Glu Gly Ala Glu Met Phe Ser Gln
                195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 99
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 99

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgacctt agtgaacaat gcagggattg ggttgttaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttttcgggca ggtaggcgat ccgactaccg ggcatacaa cgcttccaag    480
ggggcggtac gtatcatgtc gaaaagcgca gcgctgttat gcgcactgaa ggactacgat   540
gtgcgtgtca acacagtaca tccgggcccc atcaagaccc cgatgctcga tgattatgaa   600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 100
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 100

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg Arg Ala Asp Val Gly Lys Ala Ala
        35                  40                  45
Lys Ser Ile Gly Gly Thr Asp Val Ile Arg Phe Val Gln His Asp Ala
50                  55                  60
Ser Asp Glu Ala Gly Trp Thr Lys Leu Phe Asp Thr Thr Glu Glu Ala
65                  70                  75                  80
Phe Gly Pro Val Thr Thr Leu Val Asn Asn Ala Gly Ile Gly Val Val
                85                  90                  95
Lys Ser Val Glu Asp Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
130                 135                 140
Phe Gly Gln Val Gly Asp Pro Thr Thr Gly Ala Tyr Asn Ala Ser Lys
145                 150                 155                 160
Gly Ala Val Arg Ile Met Ser Lys Ser Ala Ala Leu Leu Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp Tyr Glu Gly Ala Glu Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 101
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 101

```
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg ggttgttaa aagcgttgaa     300
```

```
gacactacca cggaggaatg gcgtaaactg ctgtccgtta atctggatgg tgttttttc    360 ggcacccgtc tgggcattca gcgcatgaaa aataaaggct tgggcgctag catcatcaat    420
atgagcagta ttttcgggca ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaaccccta tgggtcacat ggcgaaccg    660 aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 102
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 102

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 103
<211> LENGTH: 756
<212> TYPE: DNA

<213> ORGANISM: Artificial Sequence
<220> FEATURE:
<223> OTHER INFORMATION: Engineered variant of Lactobacillus kefir
      ketoreductase

<400> SEQUENCE: 103

```
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgacctt agtgaacaat gcagggattg gggtttacaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagta ttttcgggat ggtaggcgat ccgactaccg gggcatacaa cgcttccaag     480
ggggcggtac gtatcatgtc gaaaagcgca gcgctgttat gcgcactgaa ggactacgat     540
gtgcgtgtca acacagtaca tccgggcccc atcaagaccc cgatgctcga tgattatgaa     600
ggtgctgagg aaatgttttc acagcgtacg aaaaacccta tgggtcacat ggcgaaccg      660 aatgacatcg catgggtctg tgtgtacctg gcatctgacg aatcgaaatt tgcgacgggt     720
gcagaatttg tggtcgacgg cgggtggacc gcacag                                756
```

<210> SEQ ID NO 104
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 104

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Gly Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190
```

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 105
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 105
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgaccgt cgtgaacaat gcagggattg ggttgttaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgttttc acagcgtacg aaaaccccta tgggtcacat tggcgaaccg     660
agtgacatcg catgggtctg tgtgtacctg gcatctgacg aatcgaaatt tgcgacgggt     720
gcagaatttg tggtcgacgg cgggtggacc gcacag                              756

<210> SEQ ID NO 106
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 106

Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

```
Lys Ser Val Glu Asp Thr Thr Thr Glu Glu Trp Arg Lys Leu Leu Ser
                100                 105                 110
Val Asn Leu Asp Gly Val Phe Phe Gly Thr Arg Leu Gly Ile Gln Arg
            115                 120                 125
Met Lys Asn Lys Gly Leu Gly Ala Ser Ile Ile Asn Met Ser Ser Ile
        130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp His Glu Gly Ala Glu Glu Met Phe Ser Gln
        195                 200                 205
Arg Thr Lys Thr Pro Met Gly His Ile Gly Glu Pro Ser Asp Ile Ala
        210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 107
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 107

```
atgaccgatc gtctgaaggg caaagtagcc atcgtaaccg gcgggacaat gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg ggttgttaa aagcgttgaa     300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta tttcgggat ggtaggcgat ccgactaccg gggcatacaa cgcttccaag    480
gggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaaccccta tggtcacat ggccgaaccg     660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 108
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 108

Met Thr Asp Arg Leu Lys Gly Lys Val Ala Ile Val Thr Gly Gly Thr

```
  1               5                  10                 15
Met Gly Ile Gly Leu Ala Ile Ala Asp Lys Phe Val Glu Glu Gly Ala
             20                 25                 30
Lys Val Val Ile Thr Gly Arg Arg Ala Asp Val Gly Glu Lys Ala Ala
             35                 40                 45
Lys Ser Ile Gly Gly Thr Asp Val Ile Arg Phe Val Gln His Asp Ala
         50                 55                 60
Ser Asp Glu Ala Gly Trp Thr Lys Leu Phe Asp Thr Thr Glu Glu Ala
 65                 70                 75                 80
Phe Gly Pro Val Thr Thr Val Val Asn Asn Ala Gly Ile Gly Val Val
                 85                 90                 95
Lys Ser Val Glu Asp Thr Thr Thr Glu Glu Trp Arg Lys Leu Leu Ser
                100                105                110
Val Asn Leu Asp Gly Val Phe Phe Gly Thr Arg Leu Gly Ile Gln Arg
                115                120                125
Met Lys Asn Lys Gly Leu Gly Ala Ser Ile Ile Asn Met Ser Ser Ile
        130                135                140
Phe Gly Met Val Gly Asp Pro Thr Thr Gly Ala Tyr Asn Ala Ser Lys
145                150                155                160
Gly Ala Val Arg Ile Met Ser Lys Ser Ala Ala Leu Asp Cys Ala Leu
                165                170                175
Lys Asp Tyr Asp Val Arg Val Asn Thr Val His Pro Gly Pro Ile Lys
                180                185                190
Thr Pro Met Leu Asp Asp Tyr Glu Gly Ala Glu Glu Met Phe Ser Gln
                195                200                205
Arg Thr Lys Thr Pro Met Gly His Ile Gly Glu Pro Asn Asp Ile Ala
        210                215                220
Trp Val Cys Val Tyr Leu Ala Ser Asp Glu Ser Lys Phe Ala Thr Gly
225                230                235                240
Ala Glu Phe Val Val Asp Gly Gly Trp Thr Ala Gln
                245                250
```

<210> SEQ ID NO 109
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 109

```
atgaccgatc gtctgaaggg caaagtagcc atcgtaaccg gcgggacaat gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tttccgatga agcaggctgg acgaaactgt tcgacaccac cgaggaggca    240
ttcggcccgg ttacgaccgt cgtgaacaat gcagggattg ggtttacaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttttcgggat gtaggcgat ccgactaccg ggcatacaa cgcttccaag    480
ggggcggtac gtatcatgtc gaaaagcgca gcgctgttat gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat tggcgaaccg    660
```

```
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 110
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 110

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Tyr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Ile Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 111
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 111

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
```

```
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg gggttctgaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttttcgggca ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaacccta tgggtcacat tggcgaaccg     660
aatgacatcg catgggtctg tgtgtacctg gcatctgacg aatcgaaatt tgcgacgggt    720
gcagaatttg tggtcgacgg cgggtacacc gcacag                              756
```

<210> SEQ ID NO 112
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 112

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
```

<210> SEQ ID NO 113
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 113

```
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgaccgt cgtgaacaat gcagggattg gggttgttaa agcgttgaa      300
gacactacca cggaggaatg gcgtaaactg ctgtccgtta atctggatgg tgttttttc      360
ggcacccgtc tgggcattca gcgcatgaaa aataaaggct gggcgctag  catcatcaat    420
atgagcagta ttttcgggca ggtaggcgat ccgactaccg gggcatacaa cgcttccaag    480
ggggcggtac gtatcatgtc gaaaagcgca gcgctgttat gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 114
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 114

```
Met Thr Asp Arg Leu Lys Gly Lys Val Ala Ile Val Thr Gly Gly Thr
  1               5                  10                  15

Met Gly Ile Gly Leu Ala Ile Ala Asp Lys Phe Val Glu Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Val
     50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160
```

Gly Ala Val Arg Ile Met Ser Lys Ser Ala Ala Leu Leu Cys Ala Leu
            165                 170                 175

Lys Asp Tyr Asp Val Arg Val Asn Thr Val His Pro Gly Pro Ile Lys
        180                 185                 190

Thr Pro Met Leu Asp Asp His Glu Gly Ala Glu Met Phe Ser Gln
    195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
            245                 250

<210> SEQ ID NO 115
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 115
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgacctt agtgaacaat gcagggattg gggtttacaa agcgttgaa      300 gacactacca cggaggaatg gcgtaaactg ctgtccgtta atctggatgg tgtttttttc     360
ggcacccgtc tgggcattca gcgcatgaaa aataaaggct tgggcgctag catcatcaat     420
atgagcagta ttttcgggat tgtaggcgat ccgactaccg gggcatacaa cgcttccaag     480
ggggcggtac gtatcatgtc gaaaagcgca gcgctgttat gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                               756

<210> SEQ ID NO 116
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 116

Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

```
Ser Asp Glu Ala Gly Trp Thr Lys Leu Phe Asp Thr Thr Glu Glu Ala
 65                  70                  75                  80

Phe Gly Pro Val Thr Thr Leu Val Asn Asn Ala Gly Ile Gly Val Tyr
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Ile Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 117
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 117
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgacctt agtgaacaat gcagggattg gggtttacaa agcgttgaa     300 gacactacca cggaggaatg cgtaaactg ctgtccgtta tctggatgg tgttttttc       360 ggcacccgtc tgggcattca gcgcatgaaa aataaaggct gggcgctag catcatcaat    420 atgagcagta ttttcgggca ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtacacc gcacag                              756

<210> SEQ ID NO 118
<211> LENGTH: 252
<212> TYPE: PRT
<213> ORGANISM: Artificial Sequence
<220> FEATURE:
```

<223> OTHER INFORMATION: Engineered variant of Lactobacillus kefir
       ketoreductase

<400> SEQUENCE: 118

Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Thr Lys Leu Phe Asp Thr Thr Glu Glu Ala
65                  70                  75                  80
Phe Gly Pro Val Thr Thr Leu Val Asn Asn Ala Gly Ile Gly Val Tyr
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Gln Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Leu Asp Asp His Glu Gly Ala Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250

<210> SEQ ID NO 119
<211> LENGTH: 756
<212> TYPE: DNA
<213> ORGANISM: Artificial Sequence
<220> FEATURE:
<223> OTHER INFORMATION: Engineered variant of Lactobacillus kefir
       ketoreductase

<400> SEQUENCE: 119
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat      420 atgagcagta ttttcgggca ggtaggcgat ccgactaccg gggcatacaa cgcttccaag     480

```
gggcggtac gtatcatgtc gaaaagcgca gcgctggatt gcgcactgaa ggactacgat      540
gtgcgtgtca acacagtaca tccgggcccc atcaagaccc cgatgctcga tgatcatgaa      600
ggtgctgagg aaatgttttc acagcgtacg aaaaccccta tgggtcacat tggcgaaccg      660
aatgacatcg catgggtctg tgtgtacctg gcatctgacg aatcgaaatt tgcgacgggt      720
gcagaatttg tggtcgacgg cgggttcacc gcacag                                756
```

<210> SEQ ID NO 120
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 120

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 121
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 121

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tttccgatga agcaggctgg acgaaactgt tcgacaccac cgaggaggca   240
ttcggcccgg ttacgaccgt cgtgaacaat gcagggattg gggttgttaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttttcgggca ggtaggcgat ccgactaccg gggcatacaa cgcttccaag   480
ggggcggtac gtatcatgtc gaaaagcgca gcgctgttat gcgcactgaa ggactacgat   540
gtgcgtgtca acacagtaca tccgggcccc atcaagaccc cgatgctcga tgattatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtggacc gcacag                             756
```

<210> SEQ ID NO 122
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 122

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
```

-continued

```
                210                 215                 220
Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 123
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 123

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tttccgatga agcaggctgg acgaaactgt tcgacaccac cgaggaggca     240
ttcggcccgg ttacgaccgt cgtgaacaat gcaggattg gggttgttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagta ttttcgggca ggtaggcgat ccgactaccg gggcatacaa cgcttccaag     480
ggggcggtac gtatcatgtc gaaaagcgca gcgctgttat gcgcactgaa ggactacgat     540
gtgcgtgtca acacagtaca tccgggcccc atcaagaccc cgatgctcga tgatcatgaa     600
ggtgctgagg aaatgttttc acagcgtacg aaaacccta tgggtcacat ggcgaaccg      660
aatgacatcg catgggtctg tgtgtacctg gcatctgacg aatcgaaatt tgcgacgggt     720
gcagaatttg tggtcgacgg cgggtggacc gcacag                              756
```

<210> SEQ ID NO 124
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 124

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Ile Thr Gly Arg Arg Ala Asp Val Gly Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125
```

```
Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 125
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 125

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tttccgatga agcaggctgg acgaaactgt tcgacaccac cgaggaggca   240
ttcggcccgg ttacgaccgt cgtgaacaat gcagggattg ggttgttaa aagcgttgaa    300 gacactacca cggaggaatg gcgtaaactg ctgtccgtta atctggatgg tgtttttttc    360
ggcacccgtc tgggcattca gcgcatgaaa aataaaggct gggcgctag catcatcaat    420 atgagcagta ttttcgggct ggtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgattatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 126
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 126

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30
```

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Gly Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Phe Gly Leu Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Met Phe Ser Gln
        195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 127
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 127
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgacctt agtgaacaat gcagggattg ggttgttaa aagcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttttcgggca ggtaggcgat ccgactaccg ggcatacaa cgcttccaag     480 ggggcggtac gtatcatgtc gaaaagcgca gcgctggatt gcgcactgaa ggactacgat     540
gtgcgtgtca acacagtaca tccgggcccc atcaagaccc cgatgctcga tgatcatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                               756

<210> SEQ ID NO 128
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 128

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Ala Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 129
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 129

| | |
|---|---|
| atgaccgatc gtctgaaggg caaagtagcc atcgtaaccg gcgggacaat gggtatcggt | 60 |
| ttggcaatcg ccgataaatt tgtagaggag ggtgcgaaag tagttattac tggtcgtcgt | 120 |
| gcggatgtag gtgaaaaggc cgccaaatca atcggcggca ctgatgttat tcgctttgtc | 180 |
| cagcacgatg tttccgatga agcaggctgg acgaaactgt tcgacaccac cgaggaggca | 240 |
| ttcggcccgg ttacgaccgt cgtgaacaat gcagggattg gggttctgaa aagcgttgaa | 300 |

```
gacactacca cggaggaatg gcgtaaactg ctgtccgtta atctggatgg tgtttttttc    360
ggcacccgtc tgggcattca gcgcatgaaa aataaaggct tgggcgctag catcatcaat    420
atgagcagta ttttcgggat tgtaggcgat ccgactaccg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgatgctcga tgatcatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 130
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 130

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Leu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Ile Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 131
<211> LENGTH: 756

<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 131

```
atgaccgatc gtctgaagag caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttatc     180
cagcacgatg tgtccgatga agcaggctgg acgaaactgt tcgacaccac cgaggaggca     240
ttcggcccgg ttacgaccgt cgtgaacaat gcagggattg gggttgttaa aagcgttgaa     300
gacactacca cggaggaatg gcgtaaactg ctgtccgtta atctggatgg tgttttttc     360
ggcacccgtc tgggcattcg ccgcatgaaa aataaaggct gggcgctag catcatcaat     420
atgagcagta ttttcgggat ggtaggcgat ccgactaccg gggcatacaa cgcttccaag     480
gggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgttttc acagcgtacg aaaaccccta tgggtcgtat tggcgaaccg     660
aatgacatcg catgggtctg tgtgtacctg gcatctgacg aatcgaaatt tgcgacgggt     720
gcagaatttg tgatcgacgg cgggtggacc gcacag                              756
```

<210> SEQ ID NO 132
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 132

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Ile Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Arg Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
```

```
                180               185                190
Thr Pro Met Leu Asp Asp Tyr Glu Gly Ala Glu Glu Met Phe Ser Gln
            195                 200                 205

Arg Thr Lys Thr Pro Met Gly Arg Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Ile Asp Gly Gly Trp Thr Ala Gln
                245                 250
```

<210> SEQ ID NO 133
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 133

```
atgaccgatc gtctgaaggg caaagtagcc atcgtaaccg gcgggacacg cggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcagggattc cggtggttaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagtg tgttcgggat tgtaggcgac ccgactaccg gggcatactg tgcttccaag   480
ggggcggtac gtatcatgtc gaaaagcgca gcgctggatt gcgcactgaa ggactacgat   540
gtgcgtgtca acacagtaca tccgggcccc atcaagaccc cgatgatgga tagctatgaa   600
ggtgctgagg aaatgttttc acagcgtacg aaaaacccta tgggtcacat tggcgaaccg   660
aatgacatcg catgggtctg tgtgtacctg gcatctgacg aatcgaaatt tgcgacgggt   720
gcagaatctg tggtcgacgg cgggtggacc gcacag                            756
```

<210> SEQ ID NO 134
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 134

```
Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95
```

```
Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Ser Val Val Asp Gly Gly Trp Thr Ala Gln
                245                 250
```

<210> SEQ ID NO 135
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 135

```
atgaccgatc gtctgaaggg caaagtagcc atcgtaaccg gcgggacacg cggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg tatccgatga agcaggctgg cctaaactgt tcgacaccac cgaggaggca    240
ttcggcccgg ttacgacctt agtgaacaat gcagggattc cggtggttaa aagcgttgaa    300
gacactacca cggaggaatg cgtaaactg ctgtccgtta atctggatgg tgttttttc     360
ggcacccgtc tgggcattca gcgcatgaaa aataaaggct gggcgctag catcatcaat    420
atgagcagtg tgttcgggat tgtaggctac ccgactaccg gggcatactg tgcttccaag    480
ggagcggtac gtatcatgtc gaaaagcgca gcgctggatt gcgcactgaa ggactacgat    540
gtgcgtgtca acacagtaca tccgggcccc atcaagaccc cgatgatgga tagctatgaa    600
ggtgctgagg aaatgttttc acagcgtacg aaaacccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 136
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 136

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 137
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 137
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc      180 cagcacgatg tatccgatga agcaggctgg actaaactgt tcgacaccac cgaggaggca     240
ttcggcccgg ttacgacctt agtgaacaat gcagggattc cgatggttaa agcgttgaa      300 gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagtg tgttcgggat tgtaggctac ccgactaccg ggcatactg tgcttccaag     480 ggggcggtac gtatcatgtc gaaaagcgca gcgctggatt gcgcactgaa ggactacgat     540
gtgcgtgtca acacagtaca tccgggcccc atcaagaccc cgatgatgga tagctatgaa     600

```
ggtgctgagg aaatgttttc acagcgtacg aaaacccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756
```

```
<210> SEQ ID NO 138
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 138
```

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

```
<210> SEQ ID NO 139
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 139
```

```
atgaccgatc gtctgaaggg caaagtagcc atcgtaaccg gcgggacacg cggtatcggt    60
ttggcaatcg ccgataaatt tgtagaggag ggtgcgaaag tagttattac tggtcgtcgt    120
```

```
gcggatgtag gtgaaaaggc cgccaaatca atcggcggca ctgatgttat tcgctttgtc    180
cagcacgatg tatccgatga agcaggctgg actaaactgt tcgacaccac cgaggaggca    240
ttcggcccgg ttacgacctt agtgaacaat gcagggattc cggttgttaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagtg tgttcgggat gtaggctac ccgactaccg gggcatactg tgcttccaag     480
ggggcggtac gtatcatgtc gaaaagcgca gcgctggatt gcgcactgaa ggactacgat    540
gtgcgtgtca acacagtaca tccgggcccc atcaagaccc cgatgatgga tagctatgaa    600
ggtgctgagg aaatgttttc acggcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                              756

<210> SEQ ID NO 140
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 140

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Glu Met Phe Ser Arg
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Trp Thr Ala Gln
            245                 250

<210> SEQ ID NO 141
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 141
atgaccgatc gtctgaaggg caaagtagcc atcgtaaccg gcgggacaca aggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt agtgaacaat gcagggattc cggtggttaa aagcgttgaa    300
gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgttcgggat gtaggcgac ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccc atcaagaccc cgatgatgga tagctatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtacacc gcacag                              756

<210> SEQ ID NO 142
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 142

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys

```
                145                 150                 155                 160
Gly Ala Val Arg Ile Met Ser Lys Ser Ala Ala Leu Asp Cys Ala Leu
                    165                 170                 175
Lys Asp Tyr Asp Val Arg Val Asn Thr Val His Pro Gly Pro Ile Lys
                    180                 185                 190
Thr Pro Met Met Asp Ser Tyr Glu Gly Ala Glu Met Phe Ser Gln
                    195                 200                 205
Arg Thr Lys Thr Pro Met Gly His Ile Gly Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                    245                 250
```

<210> SEQ ID NO 143
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 143

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt agtgaacaat gcaggggattc cggtggttaa aagcgttgaa   300
gacactacca cggaggaatg cgtaaactg ctgtccgtta atctggatgg tgttttttttc   360
ggcacccgtc tgggcattca gcgcatgaaa aataaaggct gggcgctag catcatcaat   420
atgagcagtg tgttcgggat tgtaggcgac ccgactaccg gggcatactg tgcttccaag   480
gggggcggtac gtatcatgtc gaaaagcgca gcgctggatt gcgcactgaa ggactacgat   540
gtgcgtgtca acacagtaca tccgggcccc atcaagaccc cgatgatgga tagctatgaa   600
ggtgctgagg aaatgttttc acagcgtacg aaaacccta tgggtcacat tggcgaaccg   660
aatgacatcg catgggtctg tgtgtacctg gcatctgacg aatcgaaatt tgcgacgggt   720
gcagaattg tggtcgacgg cgggtacacc gcacag                              756
```

<210> SEQ ID NO 144
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 144

```
Met Thr Asp Arg Leu Lys Gly Lys Val Ala Ile Val Thr Gly Gly Thr
1               5                   10                  15
Met Gly Ile Gly Leu Ala Ile Ala Asp Lys Phe Val Glu Glu Gly Ala
                20                  25                  30
Lys Val Val Ile Thr Gly Arg Arg Ala Asp Val Gly Glu Lys Ala Ala
            35                  40                  45
Lys Ser Ile Gly Gly Thr Asp Val Ile Arg Phe Val Gln His Asp Val
        50                  55                  60
```

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 145
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 145
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag tgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt cgtgaacaat gcaggattc cgatggttaa agcgttgaa       300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagtg tgttcgggat tgaggcgac ccgactaccg gggcatactg tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tgactatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtggacc gcacag                               756

<210> SEQ ID NO 146
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 146

```
Met Thr Asp Arg Leu Lys Gly Lys Val Ala Ile Val Thr Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 147
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 147

```
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg actaaactgt cgacaccac cgaggaggca      240 ttcggcccgg ttacgaccgt cgtgaacaat gcagggattc cggtggttaa aagcgttgaa     300
gacactacca cggaggaatg gcgtaaactg ctgtccgtta atctggatgg tgttttttc     360 ggcacccgtc tgggcattca gcgcatgaaa aataaaggct gggcgctag catcatcaat     420
```

```
atgagcagtg tgttcgggca agtaggctac ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccc atcaagaccc cgatgatgga tgactatgaa    600
ggtgctgagg aaatgttttc acagcgtacg aaaaccccta tgggtcacat ggcgaaccg     660 aatgacatcg catgggtctg tgtgtacctg gcatctgacg aatcgaaatt tgcgacgggt    720
gcagaatttg tggtcgacgg cgggtggacc gcacag                              756
```

<210> SEQ ID NO 148
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 148

```
Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Gln Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 149
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 149

```
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg cctaaactgt tcgacaccac cgaggaggca     240
ttcggcccgg ttacgaccgt agtgaacaat gcagggattc cggtggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgttcgggat gtaggcgac ccgactaccg gggcatactg tgcttccaag      480
ggggcggtac gtatcatgtc gaaaagcgca gcgctggatt gcgcactgaa ggactacgat     540
gtgcgtgtca acacagtaca tccgggcccc atcaagaccc cgatgatgga tagctatgaa     600
ggtgctgagg aaatgttttc acagcgtacg aaaaccccta tgggtcacat ggcgaaccg      660
aatgacatcg catgggtctg tgtgtacctg gcatctgacg aatcgaaatt tgcgacgggt     720
gcagaatttg tggtcgacgg cgggtggacc gcacag                               756
```

<210> SEQ ID NO 150
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 150

```
Met Thr Asp Arg Leu Lys Gly Lys Val Ala Ile Val Thr Gly Gly Thr
1               5                   10                  15
Met Gly Ile Gly Leu Ala Ile Ala Asp Lys Phe Val Glu Glu Gly Ala
            20                  25                  30
Lys Val Val Ile Thr Gly Arg Arg Ala Asp Val Gly Glu Lys Ala Ala
        35                  40                  45
Lys Ser Ile Gly Gly Thr Asp Val Ile Arg Phe Val Gln His Asp Val
    50                  55                  60
Ser Asp Glu Ala Gly Trp Pro Lys Leu Phe Asp Thr Thr Glu Glu Ala
65                  70                  75                  80
Phe Gly Pro Val Thr Thr Val Val Asn Asn Ala Gly Ile Pro Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Phe Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Ser Tyr Glu Gly Ala Glu Glu Met Phe Ser Gln
        195                 200                 205
```

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 151
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 151

```
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg catccgatga agcaggctgg cctaaactgt tcgacaccac cgaggaggca     240
ttcggcccgg ttacgacctt agtgaacaat gcagggattc cggttgttaa agcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagtg tgttcgggat tgtaggctac ccgactaccg gggcatactg tgcttccaag     480
ggggcggtac gtatcatgtc gaaaagcgca gcgctggatt gcgcactgaa ggactacgat     540
gtgcgtgtca acacagtaca tccgggccct atcaagaccc cgatgatgga tgactatgaa     600
ggtgctgagg aaatgttttc acagcgtacg aaaaccccta tgggtcacat ggcgaaccg      660
aatgacatcg catgggtctg tgtgtacctg gcatctgacg aatcgaaatt tgcgacgggt     720
gcagaatttg tggtcgacgg cgggtggacc gcacag                              756
```

<210> SEQ ID NO 152
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 152

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Pro Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg

```
                115                 120                 125
Met Lys Asn Lys Gly Leu Gly Ala Ser Ile Ile Asn Met Ser Ser Val
            130                 135                 140

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
            195                 200                 205

Arg Thr Lys Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 153
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 153

```
atgaccgatc gtctgaaggg caaagtagcc atcgtaaccg gcgggacaat gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat cgctttgtc   180
cagcacgatg tatccgatga agcaggctgg cctaaactgt cgacaccac cgaggaggca   240
ttcggcccgg ttacgaccgt agtgaacaat gcggggattc cggtggttaa aagcgttgaa   300
gacactacca cggggggaatg gcgtaaactg ctgtccgtta atctggatgg tgtttttttc   360
ggcacccgtc tgggcattca gcgcatgaaa aataaaggct gggcgctag catcatcaat   420
atgagcagtg tgttcgggat tgtaggctac ccgactaccg gggcatactg tgcttccaag   480
ggggcggtac gtatcatgtc gaaaagcgca gcgctggatt gcgcactgaa ggactacgat   540
gtgcgtgtca acacagtaca tccgggcccc atcaagaccc cgatgatgga tgaccatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtggacc gcacag                              756
```

<210> SEQ ID NO 154
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 154

```
Met Thr Asp Arg Leu Lys Gly Lys Val Ala Ile Val Thr Gly Gly Thr
1               5                   10                  15

Met Gly Ile Gly Leu Ala Ile Ala Asp Lys Phe Val Glu Glu Gly Ala
            20                  25                  30
```

Lys Val Val Ile Thr Gly Arg Arg Ala Asp Val Gly Glu Lys Ala Ala
                35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Ala
65                  70                  75                  80

Phe Gly Pro Val Thr Val Val Asn Asn Ala Gly Ile Pro Val Val
                85                  90                  95

Lys Ser Val Glu Asp Thr Thr Thr Gly Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Val
                130                 135                 140

Phe Gly Ile Val Gly Tyr Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp His Glu Gly Ala Glu Met Phe Ser Gln
                195                 200                 205

Arg Thr Lys Thr Pro Met Gly His Ile Gly Glu Pro Asn Asp Ile Ala
                210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 155
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 155
atgaccgatc gtctgaaggg caaagtagcc atcgtaaccg gcgggacacg cggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tcgtccgatga agcaggctgg actaaactgt tcgacaccac cgaggaggca   240
ttcggcccgg ttacgaccgt cgtgaacaat gcagggattc cggtggttaa aagcgttgaa   300
gacactacca cggaggaatg gcgtaaactg ctgtccgtta atctggatgg tgttttttc    360 ggcacccgtt tgggcattca gcgcatgaaa aataaaggct gggcgctag catcatcaat    420 atgagcagtg tgttcgggat tgtaggcgac ccgactaccg ggcatactg tgcttccaag    480 ggggcggtac gtatcatgtc gaaaagcgca gcgctggatt gcgcactgaa ggactacgat    540
gtgcgtgtca acacagtaca tccgggcccc atcaagaccc cgatgatgga tagccatgaa    600
ggtgctgagg aaatgttttc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtggacc gcacag                               756

<210> SEQ ID NO 156
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 156

Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser His Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 157
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 157
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg actaaactgt tcgacaccac cgaggaggca     240

```
ttcggcccgg ttacgaccgt cgtgaacaat gcagggattc cgatggttaa aagcgttgaa    300
gacactacca cggaggaatg gcgtaaactg ctgtccgtta atctggatgg tgttttttc     360 ggcacccgtc tgggcattca gcgcatgaaa aataaaggct tgggcgctag catcatcaat   420
atgagcagtg tgttcgggat ggtaggctac ccgactaccg gggcatacaa tgcttccaag   480
ggggcggtac gtatcatgtc gaaaagcgca gcgctggatt gcgcactgaa ggactacgat   540
gtgcgtgtca acacagtaca tccgggcccc atcaagaccc cgatgatgga tgattatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtacacc gcacag                             756
```

<210> SEQ ID NO 158
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 158

```
Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Met Val Gly Tyr Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 159

<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 159

```
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg catccgatga agcaggctgg actaaactgt tcgacaccac cgaggaggca     240
ttcggcccgg ttacgaccgt agtgaacaat gcaggattcc gatggttaa agcgttgaa      300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagtg tgttcgggca gtaggcgac ccgactaccg gggcatacaa tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tagccatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggttcacc gcacag                               756
```

<210> SEQ ID NO 160
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 160

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Pro Ile Lys
            180                 185                 190

Thr Pro Met Met Asp Ser His Glu Gly Ala Glu Met Phe Ser Gln
        195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 161
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 161
atgaccgatc gtctgaaggg caaagtagcc atcgtaaccg gcgggacaca aggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg actaaactgt tcgacaccac cgaggaggca     240
ttcggcccgg ttacgacctt agtgaacaat gcagggattc cggttgttaa agcgttgaa      300 gacactacca cggaggaatg gcgtaaactg ctgtccgtta atctggatgg tgtttttttc     360
ggcacccgtc tgggcattca gcgcatgaaa aataaaggct gggcgctag  catcatcaat     420 atgagcagtg tgttcgggat gtaggcgac ccgactaccg gggcatactg tgcttccaag      480
ggggcggtac gtatcatgtc gaaaagcgca gcgctggatt gcgcactgaa ggactacgat     540
gtgcgtgtca acacagtaca tccgggcccc atcaagaccc cgatgatgga tagccatgaa     600
ggtgctgagg aaatgttttc acagcgtacg aaaacccta tgggtcacat tggcgaaccg      660
aatgacatcg catgggtctg tgtgtacctg gcatctgacg aatcgaaatt tgcgacgggt     720
gcagaatttg tggtcgacgg cgggtggacc gcacag                             756

<210> SEQ ID NO 162
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 162

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Thr Lys Leu Phe Asp Thr Thr Glu Glu Ala
65                  70                  75                  80

Phe Gly Pro Val Thr Thr Leu Val Asn Asn Ala Gly Ile Pro Val Val
```

```
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Phe Gly Ile Val Gly Asp Pro Thr Thr Gly Ala Tyr Cys Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Met Met Asp Ser His Glu Gly Ala Glu Met Phe Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250

<210> SEQ ID NO 163
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 163
atgaccgatc gtctgaaggg caaagtagcc atcgtaaccg gcgggacaca aggtatcggt    60
ttggcaatcg ccgataaact tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt cgacaccac cgaggaggca   240 ttcggcccgg ttacgaccgt cgtgaacaat gcagggattc cgatggttaa aagcgttgaa   300
gacactacca cggaggaatg cgtaaaactg ctgtccgtta atctggatgg tgttttttc    360 ggcacccgtc tgggcattca gcgcatgaaa aataaaggct ggggcgctag catcatcaat   420
atgagcagtg tgttcgggat tgtaggcgac ccgactaccg gggcatacaa tgcttccaag   480
ggggcggtac gtatcatgtc gaaaagcgca gcgctggatt gcgcactgaa ggactacgat   540
gtgcgtgtca acacagtaca tccgggcccc atcaagaccc cgatgatgga tagctatgaa   600
ggtgctgagg aaatgttttc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtacacc gcacag                              756

<210> SEQ ID NO 164
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 164
```

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Leu Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 165
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 165
atgaccgatc gtctgaaggg caaagtagcc atcgtaaccg gcgggacaca aggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg tatccgatga agcaggctgg cctaaactgt tcgacaccac cgaggaggca   240
ttcggcccgg ttacgaccgt cgtgaacaat gcagggattc cggttgttaa agcgttgaa    300 gacactacca cggaggaatg gcgtaaactg ctgtccgtta atctggatgg tgttttttc    360 ggcacccgtc tgggcattca gcgcatgaaa aataaaggct gggcgctag catcatcaat    420 atgagcagtg tgttcgggat ggtaggcgat ccgactaccg gggcatactg tgcttccaag   480
ggggcggtac gtatcatgtc gaaaagcgca gcgctggatt gcgcactgaa ggactacgat   540
gtgcgtgtca acacagtaca tccgggcccc atcaagaccc cgatgatgga tgactatgaa   600
```

```
ggtgctgagg aaatgttttc acagcgtacg aaaacccta tgggtcacat tggcgaaccg    660
aatgacatcg catgggtctg tgtgtacctg gcatctgacg aatcgaaatt tgcgacgggt    720
gcagaatttg tggtcgacgg cgggtacacc gcacag                              756
```

<210> SEQ ID NO 166
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 166

```
Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Phe Gly Met Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 167
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 167

```
atgaccgatc gtctgaaggg caaagtagcc atcgtaaccg gcgggacacg cggtatcggt    60
```

```
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg catccgatga agcaggctgg cctaaactgt tcgacaccac cgaggaggca    240
ttcggcccgg ttacgacctt agtgaacaat gcaggattc cggtggtaa aagcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagtg tgttcgggat gtaggcgac ccgactaccg gggcatactg tgcttccaag    480
ggggcggtac gtatcatgtc gaaaagcgca gcgctggatt gcgcactgaa ggactacgat    540
gtgcgtgtca acacagtaca tccgggcccc atcaagaccc cgatgatgga tgactatgaa    600
ggtgctgagg aaatgttttc acagcgtacg aaaaccccta tgggtcacat ggcgaaccg     660 aatgacatcg catgggtctg tgtgtacctg gcatctgacg aatcgaaatt tgcgacgggt    720
gcagaatttg tggtcgacgg cgggttcacc gcacag                              756
```

<210> SEQ ID NO 168
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 168

```
Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
                20                  25                  30

Lys Val Val Ile Thr Gly Arg Arg Ala Asp Val Gly Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Pro Lys Leu Phe Asp Thr Thr Glu Glu Ala
65                  70                  75                  80

Phe Gly Pro Val Thr Thr Leu Val Asn Asn Ala Gly Ile Pro Val Val
                85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
    130                 135                 140

Phe Gly Ile Val Gly Asp Pro Thr Thr Gly Ala Tyr Cys Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Asp Tyr Glu Gly Ala Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Phe Thr Ala Gln
                245                 250

<210> SEQ ID NO 169
<211> LENGTH: 756
<212> TYPE: DNA
<213> ORGANISM: Artificial Sequence
<220> FEATURE:
<223> OTHER INFORMATION: Engineered variant of Lactobacillus kefir
      ketoreductase

<400> SEQUENCE: 169

| | | | | | |
|---|---|---|---|---|---|
| atgaccgatc | gtctgaaggg | caaagtagcc | atcgtaaccg | gcgggacaca | aggtatcggt | 60 |
| ttggcaatcg | ccgataaatt | tgtagaggag | ggtgcgaaag | tagttattac | tggtcgtcgt | 120 |
| gcggatgtag | gtgaaaaggc | cgccaaatca | atcggcggca | ctgatgttat | tcgctttgtc | 180 |
| cagcacgatg | tatccgatga | agcaggctgg | cctaaactgt | tcgacaccac | cgaggaggca | 240 |
| ttcggcccgg | ttacgaccgt | cgtgaacaat | gcaggattc | cggttgttaa | aagcgttgaa | 300 |
| gacactacca | cggaggaatg | gcgtaaactg | ctgtccgtta | atctggatgg | tgttttttc | 360 |
| ggcacccgtc | tgggcattca | gcgcatgaaa | aataaaggct | tgggcgctag | catcatcaat | 420 |
| atgagcagtg | tgttcgggat | tgtaggcgac | ccgactaccg | gggcatataa | tgcttccaag | 480 |
| ggggcggtac | gtatcatgtc | gaaaagcgca | gcgctggatt | gcgcactgaa | ggactacgat | 540 |
| gtgcgtgtca | acacagtaca | tccgggcccc | atcaagaccc | cgatgatgga | tagctatgaa | 600 |
| ggtgctgagg | aaatgttttc | acagcgtacg | aaaacccta | tgggtcacat | ggcgaaccg | 660 |
| aatgacatcg | catgggtctg | tgtgtacctg | gcatctgacg | aatcgaaatt | tgcgacgggt | 720 |
| gcagaatttg | tggtcgacgg | cgggtggacc | gcacag | | | 756 |

<210> SEQ ID NO 170
<211> LENGTH: 252
<212> TYPE: PRT
<213> ORGANISM: Artificial Sequence
<220> FEATURE:
<223> OTHER INFORMATION: Engineered variant of Lactobacillus kefir
      ketoreductase

<400> SEQUENCE: 170

Met Thr Asp Arg Leu Lys Gly Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Ala
65                  70                  75                  80

Phe Gly Pro Val Thr Thr Val Val Asn Asn Ala Gly Ile Pro Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

```
Phe Gly Ile Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Met Asp Ser Tyr Glu Gly Ala Glu Glu Met Phe Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250
```

<210> SEQ ID NO 171
<211> LENGTH: 756
<212> TYPE: DNA
<213> ORGANISM: Artificial Sequence
<220> FEATURE:
<223> OTHER INFORMATION: Engineered variant of Lactobacillus kefir ketoreductase

<400> SEQUENCE: 171

```
atgaccgatc gtctgaaggg caaagtagcc atcgtaaccg gcgggacacg cggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg tatccgatga agcaggctgg actaaactgt tcgacaccac cgaggaggca     240
ttcggcccgg ttacgaccgt cgtgaacaat gcagggattc cgatggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg tgttcgggat ggtaggcgac ccgactaccg gggcatactg tgcttccaag     480
ggggcggtac gtatcatgtc gaaaagcgca gcgctggatt gcgcactgaa ggactacgat     540
gtgcgtgtca acacagtaca tccgggcccc atcaagaccc cgatgatgga tgaccatgaa     600
ggtgctgagg aaatgttttc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggttcacc gcacag                               756
```

<210> SEQ ID NO 172
<211> LENGTH: 252
<212> TYPE: PRT
<213> ORGANISM: Artificial Sequence
<220> FEATURE:
<223> OTHER INFORMATION: Engineered variant of Lactobacillus kefir ketoreductase

<400> SEQUENCE: 172

```
Met Thr Asp Arg Leu Lys Gly Lys Val Ala Ile Val Thr Gly Gly Thr
1               5                   10                  15

Arg Gly Ile Gly Leu Ala Ile Ala Asp Lys Phe Val Glu Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
```

-continued

```
                50                   55                     60
Ser Asp Glu Ala Gly Trp Thr Lys Leu Phe Asp Thr Thr Glu Glu Ala
65                       70                  75                    80

Phe Gly Pro Val Thr Thr Val Val Asn Asn Ala Gly Ile Pro Met Val
                    85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Val
            130                 135                 140

Phe Gly Met Val Gly Asp Pro Thr Thr Gly Ala Tyr Cys Ala Ser Lys
145                     150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Met Met Asp Asp His Glu Gly Ala Glu Glu Met Phe Ser Gln
            195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

BIOCATALYSTS FOR THE PREPARATION OF HYDROXY SUBSTITUTED CARBAMATES

The present application is a continuation of U.S. application Ser. No. 14/825,688 filed Aug. 13, 2015, now U.S. Pat. No. 9,422,531, which is a Divisional of U.S. patent application Ser. No. 14/357,964, filed May 13, 2014, now U.S. Pat. No. 9,139,819 which is a national stage application filed under 35 USC §371 and claims priority to international application PCT/US2012/065046, filed Nov. 14, 2012, and U.S. Provisional Patent Application Ser. No. 61/561,665, filed Nov. 18, 2011. The present application hereby incorporates each of these priority applications by reference, in their entireties and for all purposes.

1. TECHNICAL FIELD

The present disclosure relates to biocatalyst-mediated processes for producing chiral compounds and biocatalysts used in the processes.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-103WO1_ST25.txt", a creation date of Nov. 13, 2012, and a size of 290,640 bytes. The Sequence Listing has only minor formatting changes relative to the Sequence Listing with file name "CX2-103USP1_ST25.txt" that was filed with the parent U.S. provisional application 61/561,665 on Nov. 18, 2011. The Sequence Listing filed via EFS-Web is part of the specification and is hereby incorporated in its entirety by reference herein.

3. BACKGROUND

The β-adrenergic receptors are members of the superfamily of G protein-coupled receptors and mediate responses to external ligands, particularly epinephrine and norepinephrine, by coupling the stimulation of $G_{\alpha s}$ to the activation of adenylyl cyclase, resulting in increased intracellular second messenger cAMP. Three subtypes of β-adrenergic receptors are known. The $\beta_1$-receptor is expressed primarily in the heart, coronary artery, kidney, muscle, and central nervous system and affects cardiac stimulation, coronary vasodilation and relaxation of the colon and esophagus. Polymorphisms in the $\beta_1$-receptor are associated with several forms of hypertension and heart failure and effects on resting heart rate. The $\beta_2$-adrenergic receptor is found in the lungs, gastrointestinal tract, liver, uterus, vascular smooth muscle, heart and skeletal muscle, where it regulates, in part, smooth muscle relaxation (e.g., bronchodilation). The $\beta_3$-adrenergic receptor is expressed primarily in adipose tissue (brown and white), urinary bladder, gallbladder, colon and heart.

There is differential, species specific expression of the various adrenergic receptor subtypes, suggesting the role of different subtypes in the same tissue of different species. In humans, the $\beta_3$-adrenoreceptor is expressed in the urinary bladder detrusor, and the $\beta_3$-adrenergic receptor mRNA is the predominant mRNA in patients undergoing radical cystectomy. Moreover, $\beta_1$ and $\beta_2$ selective agonists have no effect on detrusor function while $\beta_3$-selective agonists produce concentration-dependent relaxation (Igawa Y. et al., 1999, Br J Pharmacol. 126:819-25). These observations have led to the development of $\beta_3$-adrenoreceptor agonists for treatment of various forms of overactive bladder syndromes (see, e.g., Igawa Y. et al., 2010, Korean J Urol. 51:811-818). $\beta_3$-adrenoreceptor specific agonists based on hydroxymethyl pyrrolidines are described in WO2009124167 and WO 2009124166. Synthesis of the hydroxy pyrrolidine drug can use intermediates having the structures (a) and (b), where Ar represents an aryl group and $R^{10}$ and $R^{11}$ represent protecting groups.

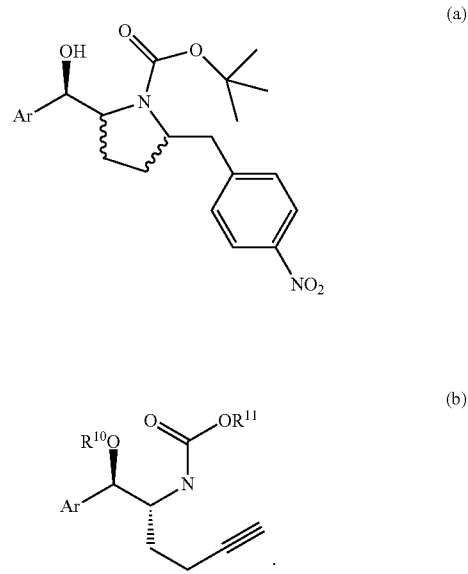

The intermediate (a) exists as cis and trans isomers that must be separated and purified to obtain chiral intermediates for synthesis of the final drug product. The synthetic route for obtaining intermediate (b) uses the starting compound 5-hexynoic acid and reaction with either (S)-(−)-4-benzyl or (S)-(−)-4-phenyl-2-oxazolidinone to set the chirality of the hydroxyl group and the left side of the pyrrolidine group (see, e.g., WO2009124167 and WO 2009124166, incorporated herein by reference).

In view of the need for separation of chiral intermediates or use of chiral specific agents for synthesis of $\beta_3$-adrenoreceptor agonists, it is desirable to find alternative synthetic routes, particularly processes that result in high diastereomeric excess of specific stereoisomers of interest, provide efficient conversion of starting material to desired product, use mild conditions, and avoids use of chiral specific chemical agents.

4. SUMMARY

The present disclosure provides non-naturally occurring, engineered polypeptides having ketoreductase activity, polynucleotides encoding the polypeptides, methods of making the polypeptides and methods of using the polypeptides for the conversion of substrate compound (2), tert-butyl(1-oxo-1-phenylhex-5-yn-2-yl)carbamate, or structural analogs thereof, to product compound (1), tert-butyl(1-hydroxy-1-phenylhex-5-yn-2-yl)carbamate, or corresponding structural analogs, as shown in Scheme 1.

Scheme 1

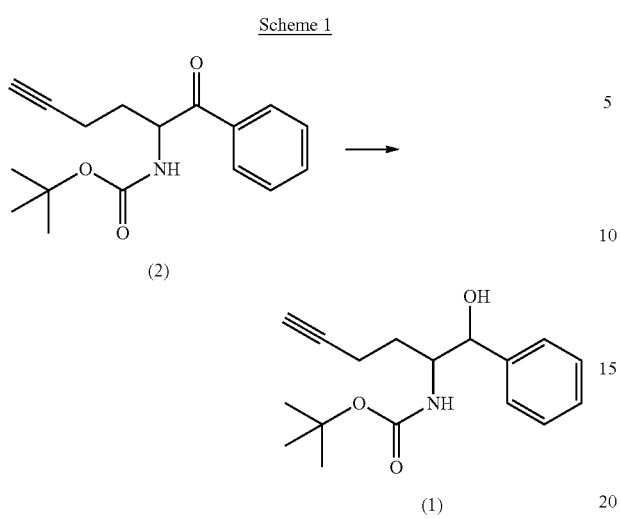

The engineered ketoreductase polypeptides developed for improved properties in the conversion of Scheme 1 have one or more residue differences as compared to the naturally occurring ketoreductase polypeptide from *Lactobacillus kefir* having amino acid sequence of SEQ ID NO:2, or the reference engineered ketoreductase having amino acid sequence of SEQ ID NO:4. These residue differences occur at residue positions affecting, among others, activity, stereoselectivity, substrate binding, stability (thermal and solvent), expression, and various combinations thereof.

In one aspect, the engineered ketoreductase polypeptide comprises an amino acid sequence having at least 80% sequence identity to a reference sequence selected from SEQ ID NO: 4, 6, 8, 10, 12, 14, 16, 18, 20, 22, 24, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 96, 98, 102, 104, 106, 108, 110, 114, 116, 122, 124, 126, 128, 130, 132, 136, 138, 140, 142, 144, 146, 148, 150, 152, 154, 156, 158, 160, 162, 164, 168, 170 and 172 and one or more residue differences as compared to SEQ ID NO:2 or 4 selected from X7S; X17M; X17Q; X17R; X23V; X27L; X29G; X40R; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X206F; X206L; X208R; X216R; X221S; X243S; X245I; X249F; X249G; and X249Y. As provided herein, in some embodiments, the disclosed amino acid differences can be used singly or in various combinations to generate the engineered ketoreductase polypeptides having the improved enzyme properties.

In some embodiments, the ketoreductase polypeptide comprises an amino acid sequence having at least 80% sequence identity to SEQ ID NO:4 and the features X40R and X206L or F, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y.

In some embodiments, the engineered ketoreductase comprises an amino acid sequence having the features X40R and X206F or L and at least one or more residue differences as compared to SEQ ID NO:4 selected from: X17Q/R/M; X64V; X94P; X144V; X147Q/I/L; X157C; and X196M.

In some embodiments, the engineered ketoreductase polypeptide with improved properties in the conversion of substrate compound (2) to product compound (1) comprises an amino acid sequence selected from SEQ ID NO: 4, 6, 8, 10, 12, 14, 16, 18, 20, 22, 24, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 96, 98, 102, 104, 106, 108, 110, 114, 116, 122, 124, 126, 128, 130, 132, 136, 138, 140, 142, 144, 146, 148, 150, 152, 154, 156, 158, 160, 162, 164, 168, 170 and 172, and in particular an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase polypeptide is capable of forming product compounds (1a) and (1c)

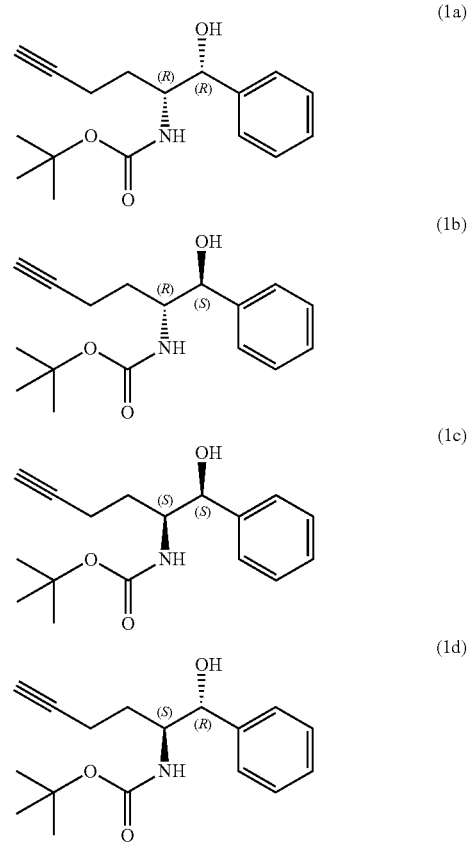

in diastereomeric excess of compounds (1b) and (1d) under suitable reaction conditions.

In some embodiments, the engineered ketoreductase polypeptide is capable of forming product compound (1a) in diastereomeric excess of compound (1c) under suitable reaction conditions.

In some embodiments, the engineered ketoreductase polypeptide capable of forming product compounds (1a) and (1c) in diastereomeric excess of compounds (1b) and (1d), or capable of forming product compound (1a) in diastereomeric excess of compound (1c), comprises an amino acid sequence having the features X40R and 206F or L, and at least one or more residue differences as compared to SEQ ID NO:4 selected from: X17Q; X64V; X71P; X87L; X147I; X157C; X196M; and X249F.

Exemplary polypeptides displaying the relevant stereoselectivity can be selected from SEQ ID NO: 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase is capable of forming compounds (1b) and (1d) in diastereomeric excess of compounds (1a) and (1c) under suitable reaction conditions. In some embodiments, the engineered ketoreductase capable of forming compounds (1b) and (1d) in diastereomeric excess of compounds (1a) and (1c) comprises an amino acid sequence having the feature X195G. Exemplary polypeptides displaying this stereoselectivity can be selected from the polypeptides of SEQ ID NO: 50 and 74.

In some embodiments, the engineered ketoreductase polypeptides are immobilized on a solid support. In some embodiments, the solid support is a bead or resin comprising polymethacrylate with epoxide functional groups, polymethacrylate with amino epoxide functional groups, styrene/DVB copolymer or polymethacrylate with octadecyl functional groups.

In another aspect, the present disclosure provides polynucleotides encoding the engineered ketoreductases, as well as expression vectors comprising the polynucleotides, and host cells capable of expressing the polynucleotides encoding the polypeptides. In some embodiments, the present disclosure also provides methods of manufacturing the engineered ketoreductase polypeptides. Exemplary polynucleotide sequences encoding the engineered ketoreductases include the sequences of SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171, in particular the sequences of SEQ ID NO: 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171.

In another aspect, the engineered ketoreductase polypeptides can be used in a process for the preparation of hydroxyl compounds of formula (I) useful for synthesis of drug compounds. Accordingly, in some embodiments, the engineered ketoreductases can be used in the conversion of substrate compounds of formula (II) to product compounds of formula (I), as shown in Scheme 2

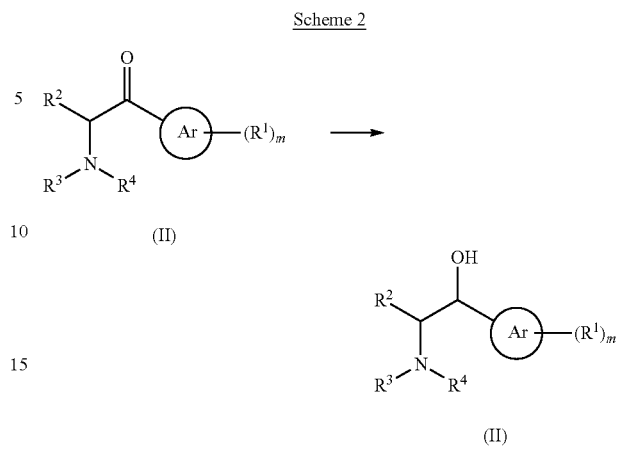

Scheme 2 wherein
Ar is a 5 to 7-membered carbocyclic or heterocyclic ring;
each occurrence of $R^1$ is independently selected from halo, $-COOR^a$, $-C(O)R^b$, $-OR^c$, $-SO_2$, $-SR^d$, $-S(O)R^e$, $-NR^fR^g$, $-C(O)NR^hR^i$, $-NO_2$, $-CN$, alkyl, heteroalkyl, cycloalkyl, cycloalkylalkyl, heterocycloalkyl, heterocycloalkylalkyl, aryl, arylalkyl, heteroaryl and heteroarylalkyl, wherein $R^a$, $R^b$, $R^c$, $R^d$, $R^e$, $R^f$, $R^g$, $R^h$ and $R^i$ are independently selected from H and an optionally substituted alkyl, heteroalkyl, cycloalkyl, cycloalkylalkyl, heterocycloalkyl, heterocycloalkylalkyl, aryl, arylalkyl, heteroaryl, and heteroarylalkyl;

$R^2$ is selected from an optionally substituted alkyl, alkenyl, alkynyl, heteroalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, alkylthio, alkylsulfinyl, and arylsulfinyl;

$R^3$ and $R^4$ are, independently of the other, selected from H, an optionally substituted alkyl, cycloalkyl, cycloalkylalkyl, heterocycloalkyl, heterocycloalkylalkyl, aryl, arylalkyl, heteroaryl, heteroarylalkyl, alkyloxycarbonyl, arylalkyloxycarbonyl, heteroarylalkyloxycarbonyl, and a protecting group, or one of $R^3$ and $R^4$ forms an optionally substituted 5 to 7-membered heterocyclic ring with $R^2$, and
m is 0 to 10.

Accordingly, a process for preparing the compound of formula (I) can comprise contacting the compound of formula (II)

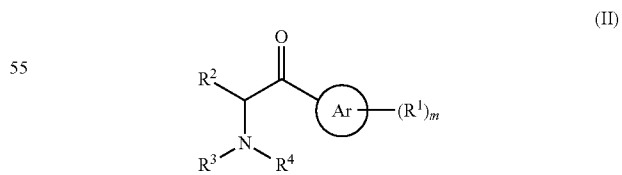

wherein
$R^1$, $R^2$, $R^3$, $R^4$, and m are as defined above;
with an engineered ketoreductase polypeptide described herein in presence of cofactor NADPH or NADH under suitable reaction conditions.

In some embodiments of the process, the compound of formula (I) comprises the compound of formula (Ib)

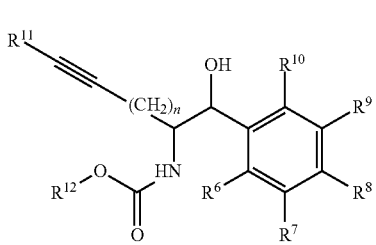

(Ib)

wherein

R⁶, R⁷, R⁸, R⁹, and R¹⁰, are each independently selected from H, halo, —COORª, —C(O)Rᵇ, —ORᶜ, —SO₂, —SRᵈ, —S(O)Rᶜ, —NRᶠRᵍ, —C(O)NRʰRⁱ, —NO₂, —CN, alkyl, heteroalkyl, cycloalkyl, cycloalkylalkyl, heterocycloalkyl, heterocycloalkylalkyl, aryl, arylalkyl, heteroaryl and heteroarylalkyl, wherein Rª, Rᵇ, Rᶜ, Rᵈ, Rᵉ, Rᶠ, Rᵍ, Rʰ and Rⁱ are independently selected from H and an optionally substituted alkyl, heteroalkyl, cycloalkyl, cycloalkylalkyl, heterocycloalkyl, heterocycloalkylalkyl, aryl, arylalkyl, heteroaryl, and heteroarylalkyl;

n is 1 to 4,

R¹¹ is selected from H and an optionally substituted alkyl, heteroalkyl, cycloalkyl, cycloalkylalkyl, aryl, arylalkyl, heteroaryl, and heteroarylalkyl; and R¹² is selected from H, an optionally substituted alkyl, cycloalkyl, cycloalkylalkyl, heterocycloalkyl, heterocycloalkylalkyl, aryl, arylalkyl, heteroaryl, heteroarylalkyl and a protecting group.

The compound of formula (Ib) can be prepared by contacting the substrate compound of formula (IIb)

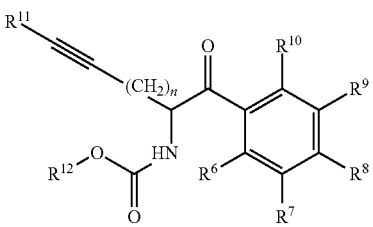

(IIb)

wherein

R⁶, R⁷, R⁸, R⁹, R¹⁰, R¹¹, R¹² and n are as defined above, with an engineered ketoreductase polypeptide of the disclosure in presence of cofactor NADPH or NADH under suitable reaction conditions.

In some embodiments, the product compound of formula (Ib) comprises the compounds of formula (Ib1) and (Ib3), and the process forms the product compounds of formula (Ib1) and (Ib3) in diastereomeric excess of compounds of formula (Ib2) and (Ib4)

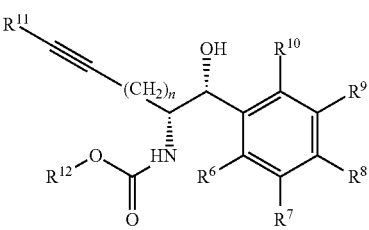

(Ib1)

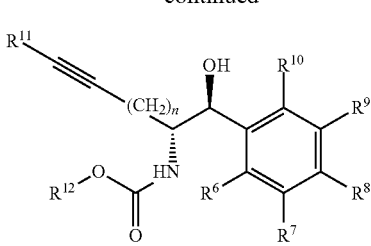

(Ib2)

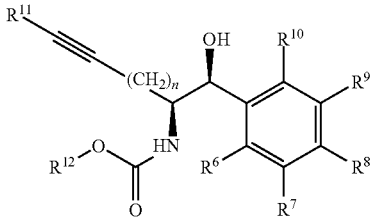

(Ib3)

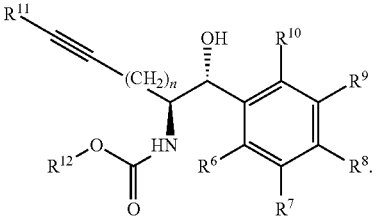

(Ib4)

Accordingly, in some embodiments, a process for preparing product compounds of formula (Ib1) and (Ib3) in diastereomeric excess of compounds of formula (Ib2) and (Ib4) comprises contacting the substrate compound of formula (IIb) with an engineered ketoreductase having diastereoselectivity for compounds of formula (Ib1) and (Ib3) over compounds of formula (Ib2) and (Ib4).

In some embodiments, the product compound of formula (Ib) comprises the compound of formula (Ib1), and the process forms the product compound of formula (Ib1) in diastereomeric excess of the compound of formula (Ib3). Accordingly, in some embodiments, a process for preparing product compound of formula (Ib1) in diastereomeric excess of compounds of formula (Ib3) comprises contacting the substrate compound of formula (IIb) with an engineered ketoreductase having diastereoselectivity for compound of formula (Ib1) over compound of formula (Ib3).

Exemplary engineered ketoreductase polypeptides having diastereoselectivity for compounds of formula (Ib1) and (Ib3) over compounds of formula (Ib2) and (Ib4) or diastereoselectivity for compound of formula (Ib1) over compound of formula (Ib3) can comprise an amino acid sequence selected from SEQ ID NO:18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the product compound of formula (Ib) comprises the compounds of formula (Ib2) and (Ib4), and the process forms the product compounds of formula (Ib2) and (Ib4) in diastereomeric excess of compounds of formula (Ib1) and (Ib3). In some embodiments, the process for preparing product compounds of formula (Ib2) and (Ib4) in diastereomeric excess of compounds of formula (Ib1) and (Ib3) comprises contacting the substrate compound of formula (IIb) with an engineered ketoreductase having diastereoselectivity for compounds of formula (Ib2) and (Ib4) over compounds of formula (Ib1) and (Ib3).

Exemplary engineered ketoreductase polypeptides having diastereoselectivity for compounds of formula (Ib2) and (Ib4) over compounds of formula (Ib1) and (Ib3) can comprise an amino acid sequence selected from SEQ ID NO: 50 and 74.

In some embodiments, the processes for preparing compounds of formula (Ib1) and (Ib3) in diastereomeric excess of compounds of formula (Ib2) and (Ib4), the compound of formula (Ib1) in diastereomeric excess of compound of formula (Ib3), and the compounds of formula (Ib2) and (Ib4) in diastereomeric excess of the compounds of formula (Ib1) and (Ib3) can be carried out under suitable reaction conditions that promote equilibration between the substrate compounds of formula (IIb1) and (IIb2)

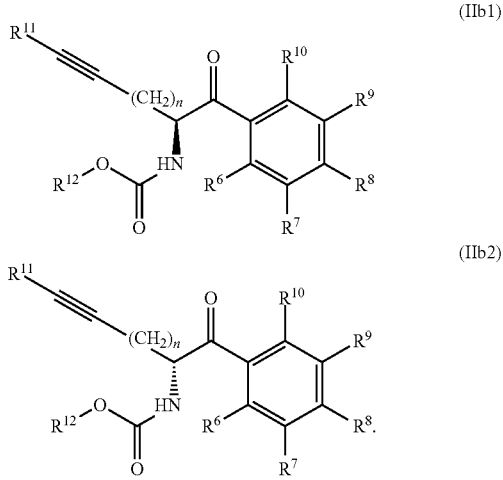

The equilibration between substrate compounds (IIb1) and (IIb2) during the conversion to product can—by dynamic kinetic resolution—increase the yield of product compound beyond the initial concentration of compounds of formula (IIb1) and (IIb2) present in the reaction solution.

In some embodiments of the processes herein using the substrate compound of formula (IIb), n is selected from 2, 3 or 4. In some embodiments, n is 2. In some embodiments, n is 2 and $R^6$, $R^7$, $R^8$, $R^9$, $R^{10}$ and $R^{11}$ are H.

Parameters for carrying out the biocatalytic processes, including among others substrate compound loading, enzyme loading, cofactor loading, solvent conditions (e.g., buffer, isopropyl alcohol, etc.), pH and temperature are further described in the detailed description below.

In some embodiments, a suitable reaction conditions can comprise: (a) engineered ketoreductase polypeptide concentration of about 1 g/L to about 10 g/L; (b) substrate compound at a loading concentration of about 50 g/L to about 200/g/L; (c) NADP(H) concentration of about 0.1 g/L to about 0.5 g/L; (d) a co-solvent solution of an aqueous buffer and about 30% to about 70% (v/v) of IPA; and (e) a temperature of 35° C. to about 60° C. In some embodiments, a suitable reaction conditions can comprise: (a) engineered ketoreductase polypeptide concentration of about 0.1 g/L to about 1 g/L; (b) substrate compound at a loading concentration of about 5 g/L to about 50 g/L; (c) NADP(H) concentration of about 0.01 g/L to about 0.1 g/L; (d) a co-solvent solution of an aqueous buffer, and about 30% to about 70% (v/v) of IPA; and (e) a temperature of about 30° C. to about 45° C.

In some embodiments, the reaction conditions for equilibration of substrate compounds of formula (IIb1) and (IIb2) for dynamic kinetic resolution can comprise a pH of about 9 to about 12 and a temperature of about 45° C. to about 60° C.

Various embodiments as well as guidance on making and using the engineered polypeptides, the polynucleotides encoding the polypeptides and the processes for biocatalytic conversion are provided in the following detailed description.

5. DETAILED DESCRIPTION

For the descriptions herein and the appended claims, the singular forms "a", "an" and "the" include plural referents unless the context clearly indicates otherwise. Thus, for example, reference to "a polypeptide" includes more than one polypeptide, and reference to "a compound" refers to more than one compound.

It is to be further understood that where descriptions of various embodiments use the term "comprising," those skilled in the art would understand that in some specific instances, an embodiment can be alternatively described using language "consisting essentially of" or "consisting of."

Also, the use of "or" means "and/or" unless stated otherwise. Similarly, "comprise," "comprises," "comprising" "include," "includes," "including," "has," "have," and "having" are interchangeable and not intended to be limiting.

The foregoing general description and the detailed description are exemplary and explanatory only and are not restrictive of this disclosure.

The section headings used herein are for organizational purposes only and not to be construed as limiting the subject matter described.

5.1. Abbreviations

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon (Cα). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

5.2. Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic acid" refers to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases, such as, for example, inosine, xanthine, hypoxanthine, etc. Preferably, such modified or synthetic nucleobases will be encoding nucleobases.

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Non-naturally occurring" or "engineered" or "recombinant" when used in the present disclosure with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn" as further described below, is to be construed as referring to "a residue corresponding to", unless specifically denoted otherwise.

"Stereoselectivity" refers to the preferential formation in a chemical or enzymatic reaction of one stereoisomer over another stereoisomer or another set of stereoisomers. Stereoselectivity can be partial, where the formation of a stereoisomer is favored over another, or it may be complete where only one stereoisomer is formed. When the stereoisomers are enantiomers, the stereoselectivity is referred to as enantioselectivity, the fraction (typically reported as a percentage) of one enantiomer in the sum of both enantiomers. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. It is also to be understood that stereoselectivity is not limited to single stereoisomers and can be described for sets of stereoisomers, for example stereoselectivity for compounds (1a) and (1c) over compounds (1b) and (1d), as further described herein.

"Highly stereoselective" refers to a chemical or enzymatic reaction that is capable of converting a substrate, e.g., compound (2), to its corresponding chiral alcohol product, e.g., compounds (1a) and (1c), with at least about 85% stereomeric excess.

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

"Solvent stable" refers to the ability of a polypeptide to maintain similar activity (e.g., more than e.g., 60% to 80%) after exposure to varying concentrations (e.g., 5-99%) of solvent (e.g., isopropyl alcohol, tetrahydrofuran, 2-methyl-tetrahydrofuran, acetone, toluene, butylacetate, methyl tert-butylether, etc.) for a period of time (e.g., 0.5-24 hrs) compared to the untreated enzyme.

"Amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X40 as compared to SEQ ID NO: 4" refers to a difference of the amino acid residue at the polypeptide position corresponding to position 40 of SEQ ID NO:4. Thus, if the reference polypeptide of SEQ ID NO: 4 has a histidine at position 40, then a "residue difference at position X40 as compared to SEQ ID NO:4" refers to an amino acid substitution of any residue other than histidine at the position of the polypeptide corresponding to position 40 of SEQ ID NO: 4. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances (e.g., in Tables 2A, 2B, and 2C), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X192A/G). The present disclosure includes engineered polypeptide sequences comprising one or more amino acid differences that include either/or both conservative and non-conservative amino acid substitutions. The amino acid sequences of the specific recombinant carbonic anhydrase polypeptides included in the Sequence Listing of the present disclosure include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO: 4 at position Xn" as used herein may refer to position "Xn" or to the corresponding position (e.g., position (X−1)n) in a reference sequence that has been processed so as to lack the starting methionine.

"Conservative amino acid substitutions" refer to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1.

TABLE 1

| Residue | Possible Conservative Substitutions |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

"Insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to engineered ketoreductase polypeptides. Insertions can be in the internal portions of the polypeptide, or to the carboxy or amino terminus Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can typically have about 80%, 90%, 95%, 98%, and 99% of the full-length ketoreductase polypeptide, for example the polypeptide of SEQ ID NO:4.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present disclosure can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 95% or more, and about 98% or more of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Cofactor regeneration system" or "cofactor recycling system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

"Secondary alcohol dehydrogenase" is used herein to refer to an NAD+ or NADP+-dependent enzyme that catalyzes the conversion of a secondary alcohol (e.g., isopropyl alcohol) and NAD+ or NADP+ to a ketone and NADH or NADPH, respectively.

"Suitable reaction conditions" refer to those conditions in the biocatalytic reaction solution (e.g., ranges of enzyme loading, substrate loading, cofactor loading, temperature, pH, buffers, co-solvents, etc.) under which a ketoreductase polypeptide of the present disclosure is capable of converting a substrate compound to a product compound (e.g., conversion of compound (2) to compound (1)). Exemplary "suitable reaction conditions" are provided in the present disclosure and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the ketoreductase biocatalyst in the process disclosed herein is compound (2).

"Product" in the context of a biocatalyst mediated process refers to the compound or molecule resulting from the action of the biocatalyst. For example, an exemplary product for the ketoreductase biocatalyst in the process disclosed herein is compound (1).

"Equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

"Alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., $(C_1-C_4)$alkyl refers to an alkyl of 1 to 4 carbon atoms.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Heteroalkyl, "heteroalkenyl," and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —NR$^\alpha$—, —PH—, —S(O)—, —S(O)2-, —S(O)NR$^\alpha$—, —S(O)$_2$NR$^\alpha$—, and the like, including combinations thereof, where each R$^\alpha$ is independently selected from hydrogen, alkyl, heteroalkyl, cycloalkyl, heterocycloalkyl, aryl, and heteroaryl.

"Alkoxy" refers to the group —OR$^\beta$ wherein R$^\beta$ is an alkyl group is as defined above including optionally substituted alkyl groups as also defined herein.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to an alkyl substituted with an aryl, i.e., aryl-alkyl- groups, preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

"Arylalkenyl" refers to an alkenyl substituted with an aryl, i.e., aryl-alkenyl- groups, preferably having from 2 to 6 carbon atoms inclusively in the alkenyl moiety and from 6 to 12 carbon atoms inclusively in the aryl moiety.

"Arylalkynyl" refers to an alkynyl substituted with an aryl, i.e., aryl-alkynyl- groups, preferably having from 2 to 6 carbon atoms inclusively in the alkynyl moiety and from 6 to 12 carbon atoms inclusively in the aryl moiety.

"Carbocycle" and "carbocyclic" are used interchangeably herein to refer to ring structures of 3 to 12 atoms where all the ring atoms are carbon atoms. Carbocycle includes cycloalkyl and aryl groups. Exemplary carbocycles include, but are not limited to, cyclopentyl, cyclohexyl, cycloheptyl, cyclooctyl, cyclopentenyl, cyclohexenyl, cyclohexadienyl, and phenyl.

"Cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to an alkyl substituted with a cycloalkyl, i.e., cycloalkyl-alkyl- groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

"Cycloalkylalkenyl" refers to an alkenyl substituted with a cycloalkyl, i.e., cycloalkyl-alkenyl- groups, preferably having from 2 to 6 carbon atoms inclusively in the alkenyl moiety and from 3 to 12 carbon atoms inclusively in the cycloalkyl moiety.

"Cycloalkylalkynyl" refers to an alkynyl substituted with a cycloalkyl, i.e., cycloalkyl-alkynyl- groups, preferably having from 1 to 6 carbon atoms inclusively in the alkynyl moiety and from 3 to 12 carbon atoms inclusively in the cycloalkyl moiety.

"Amino" refers to the group —NH$_2$. Substituted amino refers to the group —NHR$^\delta$, NR$^\delta$R$^\delta$, and NR$^\delta$R$^\delta$R$^\delta$, where each R$^\delta$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylysulfonylamino, furanyl-oxy-sulfamino, and the like.

"Alkylamino" refers to a —NHR$^\delta$ group, where R$^\delta$ is an alkyl, an N-oxide derivative, or a protected derivative thereof, e.g., methylamino, ethylamino, n-propylamino, iso-propylamino, n-butylamino, iso-butylamino, tert-butylamino, or methylamino-N-oxide, and the like.

"Aminoalkyl" refers to an alkyl group in which one or more of the hydrogen atoms are replaced with an amino group as defined herein, including a substituted amino group.

"Oxo" refers to =O.

"Oxy" refers to a divalent group —O—, which may have various substituents to form different oxy groups, including ethers and esters.

"Carboxy" refers to —COOH. "Carbonyl" refers to —C(O)—, which may have a variety of substituents to form different carbonyl groups including acids, acid halides, aldehydes, amides, esters, and ketones.

"Carbonyl" refers to —C(O)—, which may have various substituents to form different carbonyl groups, including esters and ketones.

"Alkyloxycarbonyl" refers to —C(O)OR$^\epsilon$, where R$^\epsilon$ is an alkyl group as defined herein, which can be optionally substituted.

"Aryloxycarbonyl" refers to —C(O)OR$^\zeta$, where R$^\zeta$ is an aryl group as defined herein, which can be optionally substituted.

"Arylalkyloxycarbonyl" refers to —C(O)OR$^\rho$, where R$^\rho$ is an aryl-alkyl- group as defined herein, which can be optionally substituted.

"Heteroaryloxycarbonyl" refers to —C(O)OR$^\sigma$ where R$^\sigma$ is a heteroaryl group as defined herein, which can be optionally substituted.

"Heteroarylalkyloxycarbonyl" refers to —C(O)OR$^\omega$ where R$^\omega$ is a heteroarylalkyl group as defined herein, which can be optionally substituted.

"Aminocarbonyl" refers to —C(O)NH$_2$. Substituted aminocarbonyl refers to —C(O)NR$^\delta$R$^\delta$, where the amino group NR$^\delta$R$^\delta$ is as defined herein.

"Halogen" or "halo" refers to fluoro, chloro, bromo and iodo.

"Hydroxy" refers to —OH.

"Cyano" refers to —CN.

"Alkylthio" refers to —S—R$^\eta$. where R$^\eta$ is an alkyl. Typical alkylthio include, but are not limited to, methylthio, ethylthio, n-propylthio, and the like.

"Sulfonyl" refers to —SO$_2$—. Substituted sulfonyl refers to —SO$_2$R$^\kappa$, where R$^\kappa$ is an alkyl, aryl or other suitable substituent as described below.

"Alkylsulfonyl" refers to —SO$_2$R$^\kappa$, where R$^\kappa$ is an alkyl group as defined herein.

"Arylsulfonyl" refers to —SO$_2$R$^\kappa$, where R$^\kappa$ is an aryl group as defined herein.

"Sulfinyl" refers to a —S(O)R$^\lambda$, where R$^\lambda$ is selected from alkyl, cycloalkyl, aryl, heteroaryl (bonded through a ring carbon) and heterocycle (bonded through a ring carbon).

"Alkylsulfinyl" refers to a —S(O)R$^\lambda$ where R$^\lambda$ is an alkyl group as defined herein.

"Arylsulfinyl" refers to —S(O)R$^\lambda$ where R$^\lambda$ is an aryl group as defined herein.

"Aminosulfonyl" refers to —SO$_2$NH$_2$. Substituted aminosulfonyl refers to —SO$_2$NR$^\delta$R$^\delta$, where the amino group —NR$^\delta$R$^\delta$ is as defined herein.

"Haloalkyl" refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "($C_1$ $C_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to an alkyl substituted with a heteroaryl, i.e., heteroaryl-alkyl- groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

"Heteroarylalkenyl" refers to an alkenyl substituted with a heteroaryl, i.e., heteroaryl-alkenyl- groups, preferably having from 2 to 6 carbon atoms inclusively in the alkenyl moiety and from 5 to 12 ring atoms inclusively in the heteroaryl moiety.

"Heteroarylalkynyl" refers to an alkynyl substituted with a heteroaryl, i.e., heteroaryl-alkynyl- groups, preferably having from 2 to 6 carbon atoms inclusively in the alkynyl moiety and from 5 to 12 ring atoms inclusively in the heteroaryl moiety.

"Heterocycle", "heterocyclic" and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Heterocycloalkylalkyl" refers to an alkyl substituted with a heterocycloalkyl, i.e., heterocycloalkyl-alkyl- groups, preferably having from 1 to 6 carbon atoms inclusively in the alkyl moiety and from 3 to 12 ring atoms inclusively in the heterocycloalkyl moiety.

"Heterocycloalkylalkenyl" refers to an alkenyl substituted with a heterocycloalkyl, i.e., heterocycloalkyl-alkenyl-groups, preferably having from 2 to 6 carbon atoms inclusively in the alkenyl moiety and from 3 to 12 ring atoms inclusively in the heterocycloalkyl moiety.

"Heterocycloalkylalkynyl" refers to an alkynyl substituted with a heterocycloalkyl, i.e., heterocycloalkyl-alkynyl-groups, preferably having from 2 to 6 carbon atoms inclusively in the alkynyl moiety and from 3 to 12 ring atoms inclusively in the heterocycloalkyl moiety.

"Membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

"Optional" or "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

"Protecting group" refers to a group of atoms that mask, reduce or prevent the reactivity of the functional group when attached to a reactive functional group in a molecule. Typically, a protecting group may be selectively removed as desired during the course of a synthesis. Examples of protecting groups can be found in Wuts and Greene, "Greene's Protective Groups in Organic Synthesis," $4^{th}$ Ed., Wiley Interscience (2006), and Harrison et al., Compendium of Synthetic Organic Methods, Vols. 1-8, 1971-1996, John Wiley & Sons, NY. Functional groups that can have a protecting group include, but are not limited to, hydroxy, amino, and carboxy groups. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers. Other protecting groups can be found in the references noted herein.

5.3. Engineered Ketoreductase Polypeptides

Ketoreductase (KRED) or carbonyl reductase biocatalysts (EC 1.1.1.184) are useful for the synthesis of alcohols from aldehydes and ketones, and optically active secondary alcohols from the corresponding prostereoisomeric ketone substrates. KREDs may also catalyze the reverse reaction, i.e., oxidation of an alcohol substrate to the corresponding aldehydes/ketone product. The reduction of aldehydes and ketones and the oxidation of alcohols by KREDs uses a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD+ and NADP+ serve as electron acceptors.

KREDs can be found in a wide range of bacteria and yeasts (for reviews see, e.g., Kraus and Waldman, Enzyme catalysis in organic synthesis Vols. 1&2.VCH Weinheim 1995; Faber, K., Biotransformations in organic chemistry, 4th Ed. Springer, Berlin Heidelberg New York. 2000; Hummel and Kula Eur. J. Biochem. 1989 184:1-13). Numerous KRED genes and enzyme sequences have been reported, including: *Candida magnoliae* (Genbank Acc. No. JC7338; GI:11360538); *Candida parapsilosis* (Genbank Acc. No. BAA24528.1; GI:2815409), *Sporobolomyces salmonicolor* (Genbank Acc. No. AF160799; GI:6539734); *Lactobacillus kefir* (Genbank Acc. No. AAP94029.1; GI: 33112056); *Lactobacillus brevis* (Genbank Acc. No. 1NXQ_A; GI: 30749782); and *Thermoanaerobium brockii* (Genbank Acc. No. P14941; GI: 1771790).

The stereoselectivity of ketoreductases have been applied to the preparation of important pharmaceutical building blocks (see, e.g., Broussy et al., 2009, Org Lett. 11(2):305-308). Specific applications of naturally occurring or engineered KREDs in biocatalytic processes to generate useful chemical compounds have been demonstrated for reduction of 4-chloroacetoacetate esters (Zhou, J. Am. Chem. Soc. 1983 105:5925-5926; Santaniello, J. Chem. Res. (S) 1984: 132-133; U.S. Pat. No. 5,559,030; U.S. Pat. No. 5,700,670 and U.S. Pat. No. 5,891,685), reduction of dioxocarboxylic acids (e.g., U.S. Pat. No. 6,399,339), reduction of tert-butyl (S)-chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

As discussed herein, tert-butyl(1-hydroxy-1-phenylhex-5-yn-2-yl)carbamate is an intermediate in the synthesis of hydroxymethyl pyrrolidine based $\beta_3$-adrenoreceptor agonists (e.g., WO2009124167 and WO 2009124166, incorporated herein by reference). Naturally occurring and previously engineered KREDs do not efficiently convert substrate compound (2), tert-butyl(1-oxo-1-phenylhex-5-yn-2-yl)carbamate, to product compound (1), tert-butyl(1-hydroxy-1-phenylhex-5-yn-2-yl)carbamate, as illustrated in Scheme 1 above. However, the present disclosure describes the development of non-naturally occurring (i.e., engineered) KREDs with improved properties in carrying out the conversion of Scheme 1. These improved properties include, among others, increased activity, increased selectivity for certain diastereoisomers, increased stability (e.g., thermal and solvent), high percent substrate conversion (esp., in presence of high substrate loadings), enhanced polypeptide expression, and various combinations of improvements thereof.

For the purposes of the descriptions herein, it will apparent to the skilled artisan that compound (2) has two chiral centers and can exist in at least two different diastereomeric forms (e.g., compounds (2a) and (2b)). Consequently, reduction by the ketoreductase can result in at least four different stereoisomeric forms of product (e.g., compounds (1a), (1b), (1c) and (1d)), as shown in Scheme 3.

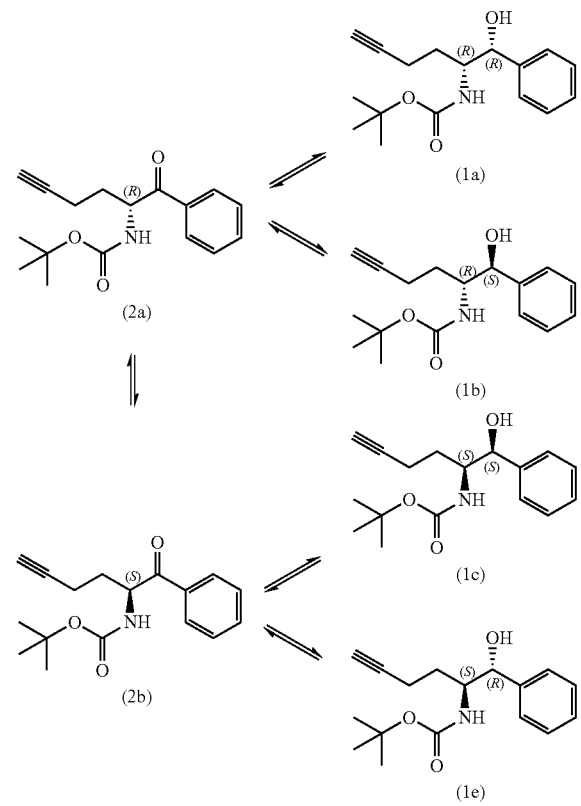

Scheme 3

Accordingly, as used herein, a reference to compound (2) or its structural analogs without any specified stereomeric structure refers to any mixtures, including racemic mixtures, or pure preparations of the stereoisomeric forms of the compound that are substrates for the engineered ketoreductases disclosed herein (e.g., compounds (2a) and (2b)). Similarly, a reference to product compound (1) or its structural analogs without any indication of a specific stereomeric structure refers to any mixtures of the stereomeric forms of product compound (1) formed in the ketoreductase reaction (e.g., compounds (1a), (1b), (1c), and (1d)). Moreover, the engineered ketoreductases of the present disclosure can also carry out the reverse reaction to convert compound (1) to the corresponding ketone of compound (2), and promote equilibration between the two substrate compounds (2a) and (2b), as illustrated in Scheme 2.

The non-naturally occurring polypeptides of the present disclosure are ketoreductases engineered to have improved properties as compared to the naturally occurring ketoreductase of SEQ ID NO:2 or the engineered ketoreductase of SEQ ID NO:4. The engineered ketoreductase polypeptides are adapted for efficient conversion of compound (2) to compound (1) and have one or more residue differences as compared to the naturally occurring ketoreductase of SEQ ID NO:2, or the reference engineered ketoreductase polypeptide of SEQ ID NO: 4, which has the following 11 amino acid differences relative to the naturally occurring ketoreductase of SEQ ID NO:2 from *Lactobacillus kefir*: A94G; S96V; E145F; F147M; L153T; Y190P; L195M; V196L; L199Y; I226V; and Y249W. These residue differences are associated with improvements in enzyme properties, particularly increased activity, increased stereoselectivity, increased stability, and tolerance of increased substrate and/or product concentration (e.g., decreased product inhibition).

In some embodiments, the engineered ketoreductase polypeptides are capable of converting the substrate compound (2) to compound (1) with an activity that is increased at least about 1.2 fold, 1.5 fold, 2 fold, 3 fold, 4 fold, 5 fold, 10 fold, 20 fold, 30 fold, 40 fold, 50 fold, 100 fold, 200 fold, 500 fold, 1000 fold, 5000 fold, 10000 fold or more relative to the activity of the reference polypeptide of SEQ ID NO: 4 under suitable reaction conditions. In some embodiments, the engineered ketoreductase polypeptides are capable of converting the substrate of compound (2) to compound (1) with a percent conversion of at least about 40%, at least about 50%, at least about 60%, at least about 70%, at least about 80%, or at least about 90%, at least about 95%, at least about 98%, at least about 99%, in a reaction time of about 48 h, about 36 h, about 24 h, or even shorter length of time, under suitable reaction conditions.

In some embodiments, the engineered ketoreductase polypeptides described herein exhibit diastereoselectivity for syn compounds (1a) and (1c) over anti compounds (1b) and (1d) under suitable reaction conditions

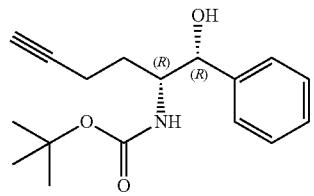
(1a)

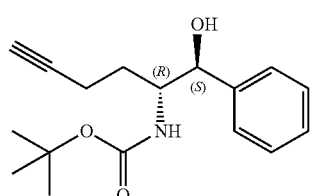
(1b)

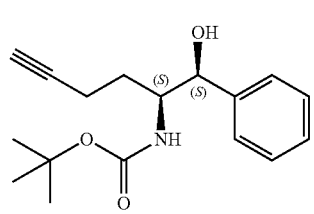
(1c)

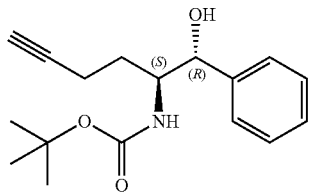
(1d)

In some embodiments, the engineered ketoreductase polypeptides are capable of converting compound (2) to syn compounds (1a) and (1c) (i.e., [1a+1c]) in a diastereomeric ratio greater than 10:1, 20:1, 30:1, 40:1, 50:1, 60:1, 70:1, 80:1, 90:1, or 100:1 or greater over anti compounds (1b) and (1d) (i.e., [1b+1d]). In some embodiments, the engineered ketoreductase polypeptides are capable of converting substrate compound (2) to product compounds (1a) and (1c) (i.e., [1a+1c]) in a diastereomeric ratio greater than 50:1 over compounds (1b) and (1d) (i.e., [1b+1d] under suitable reaction conditions.

In some embodiments, the engineered ketoreductases are capable of converting substrate compound (2) to product compound (1a) in diastereomeric excess over compound (1c). In some embodiments, the engineered ketoreductases are capable of converting compound (2) to compound (1a) in diastereomeric excess of at least 10%, 20%, 30%, 40%, 50%, 60%, 70%, 80%, 90%, or greater over compound (1c) under suitable reaction conditions.

In some embodiments, the engineered ketoreductase polypeptides exhibit diastereoselectivity for compounds (1b) and (1d) over compounds (1a) and (1c). Thus, in some embodiments, the engineered ketoreductases are capable of converting compound (2) to compounds (1b) and (1d) in diastereomeric excess of compounds (1a) and (1c) under suitable reaction conditions.

As further discussed below, the diastereoselectivity of the engineered ketoreductases and the equilibration between the substrate compounds can be used in a dynamic kinetic resolution process to prepare certain diastereomers in excess, and in some instances, to prepare substantially pure preparations of the diastereomer or diastereomers.

In some embodiments, the engineered ketoreductase polypeptides are capable of converting compound (2) to compound (1) with increased tolerance for the presence of substrate relative to the reference polypeptide of SEQ ID NO: 4 under suitable reaction conditions. Accordingly, in some embodiments the engineered ketoreductase polypeptides are capable of converting the substrate of compound (2) to compound (1) in the presence of a substrate loading concentration of at least about 1 g/L, about 5 g/L, about 10 g/L, about 20 g/L, about 30 g/L, about 40 g/L, about 50 g/L, about 70 g/L, about 100 g/L, about 125 g/L, about 150 g/L. about 175 g/L or about 200 g/L or more with a percent conversion of at least about 40%, at least about 50%, at least about 60%, at least about 70%, at least about 80%, at least about 90%, at least about 95%, at least about 98%, or at least about 99%, in a reaction time of about 72 h, about 48 h, about 36 h, about 24 h, or even shorter length of time, under suitable reaction conditions.

The suitable reaction conditions under which the above-described improved properties of the engineered polypeptides carry out the conversion can be determined with respect to concentrations or amounts of polypeptide, substrate, cofactor, buffer, co-solvent, pH, and/or conditions including temperature and reaction time, as further described below and in the Examples.

The exemplary engineered polypeptides associated with their improved properties for conversion of compound (2) to compound (1) include one or more residue differences as compared to SEQ ID NO:4 at the following residue positions: X7; X17; X23; X27; X29; X40; X60; X64; X71; X87; X94; X95; X96; X105; X113; X122; X127; X131; X144; X145; X147; X150; X152; X153; X157; X173; X195; X196; X198; X199; X206; X208; X216; X221; X243; X245; and X249. The specific amino acid differences at each of these positions that are associated with the improved properties of the exemplary polypeptides of Tables 2A, 2B, and 2C include: X7S; X17M; X17Q; X17R; X23V; X27L; X29G; X40R; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X206F; X206L; X208R; X216R; X221S; X243S; X245I; X249F; X249G; and X249Y.

Structure and function information for exemplary engineered ketoreductase polypeptides of the present disclosure are shown below in Tables 2A, 2B and 2C. The odd numbered sequence identifiers (i.e., "SEQ ID NO:") refer to the nucleotide sequence encoding the amino acid sequence provided by the even numbered SEQ ID NOs, and the sequences are provided in the electronic Sequence Listing file accompanying this disclosure, which is hereby incorporated by reference herein. The amino acid residue differences are based on comparison to the reference polypeptide sequence of SEQ ID NO: 4, which is an engineered ketoreductase polypeptide having the following 11 amino acid differences relative to the naturally occurring ketoreductase of *Lactobacillus kefir* (SEQ ID NO: 2): A94G; S96V; E145F; F147M; L153T; Y190P; L195M; V196L; L199Y; I226V; and Y249W. The "syn:cis diastereomeric ratio" (also referred to herein as "d.r.") is the ratio of the two possible syn diastereomeric products compound (1a) and compound (1c) to the two possible anti diastereomer products compound (1b) and compound (1d). The diastereomeric ratio can be calculated from the formula, [1a+1c]/[1b+1d].

In the screening of ketoreductases herein, the engineered polypeptide of SEQ ID NO: 4 was found to convert compound (2) to compound (1a) and (1c) with a d.r. of >100 (under reaction condition E) but with lower activity than the engineered ketoreductases selected for improved properties in the conversion of substrate compound (2) to product compounds (1a) and (1c). Thus, the engineered polypeptide of SEQ ID NO:4 was used as the starting point for the further evolution of engineered polypeptides that had increased activity in converting substrate compound (2) to product compounds (1a) and (1c) and with high d.r. The activity of each engineered polypeptide was determined using a high-throughput (HTP) assay (as a primary screen). The HTP assay values in Table 2A were determined using *E. coli* clear cell lysates in 96 well-plate format of ~200 µL volume per well following assay reaction conditions as noted in the table. In some cases, a secondary shake-flask powder (SFP) and/or downstream processed (DSP) powder assay was used to assess the properties of the engineered ketoreductases. The SFP and DSP forms provide a more purified powder preparation of the engineered polypeptides. For example, the engineered ketoreductase in the SFP preparations are approximately 30% of the total protein. The SFP assay values in Table 2B were determined using SFP of the engineered polypeptides in a 2 mL vial format using reaction conditions noted in the table. The DSP assay values in Table 2C were determined using DSP powders of the engineered polypeptides in a 2 mL or 5 mL vial format using reaction conditions noted in the table. Further details of the HTP, SFP, and DSP preparations and assays are described in the Examples.

TABLE 2A

| SEQ ID NO: (nt/aa) | Amino Acid Differences (relative to SEQ ID NO: 4) | Activity (relative to SEQ ID NO: 4) | Assay[1] |
|---|---|---|---|
| 3/4 | n/a | 1.0 | i |
| 5/6 | V96L | 4.4 | i |
| 7/8 | M195A | 3.5 | i |
| 9/10 | M206F | 4.9 | i |
| 17/18 | H40R; G94P; M206F | 112.7 | ii |
| 19/20 | H40R; V95M; M206F | 81.3 | ii |
| 21/22 | H40R; I144V; M206F | 77.5 | ii |
| 23/24 | H40R; L196M; M206F | 77.0 | ii |
| 25/26 | H40R; D198S; M206F; | 323.8 | ii |
| 27/28 | H40R; A64V; V87L; M147Q; Y199H; M206F; | 137.8 | ii |
| 29/30 | H40R; A64V; M147Q; Y199H; M206F | 121.4 | ii |
| 33/34 | L17Q; H40R; A64V; T71P; G94P; V95M; T122A; I144V; M147I; N157C; L196M; D198S; M206F; W249Y | 25190.1 | iii |
| 35/36 | L17Q; H40R; A64V; T71P; G94P; I144V; M147I; N157C; L196M; M206F; W249F | 23882.6 | iii |
| 37/38 | L17M; H40R; A64V; V87L; G94P; I144V; N157C; L196M; D198S; Y199H; M206F; W249F | 22691.3 | iii |
| 39/40 | L17R; H40R; A64V; V87L; G94P; I144V; M147I; D150Y; N157C; L196M; D198S; M206F | 10801.3 | iii |
| 41/42 | L17Q; I23V; H40R; A64V; T71P; V87L; G94P; V95M; I144V; M147I; T153G; N157C; L196M; D198S; M206F; W249F | 29528.6 | iii |
| 43/44 | L17R; H40R; A64V; T71P; G94P; V95M; I144V; D150Y; L196M; D198S; M206F | 11467.5 | iii |
| 45/46 | V96Y | 1.5 | i |
| 47/48 | F145L | 2.1 | i |
| 49/50 | M195G | 13.8 (opposite d.r.) | i |
| 51/52 | M206L | 2.3 | i |
| 53/54 | Y199H | 2.4 | i |
| 55/56 | L17Q; H40R; M206F | 346.6 | ii |

TABLE 2A-continued

| SEQ ID NO: (nt/aa) | Amino Acid Differences (relative to SEQ ID NO: 4) | Activity (relative to SEQ ID NO: 4) | Assay[1] |
|---|---|---|---|
| 57/58 | L17R; H40R; M206F | 248.1 | ii |
| 59/60 | E29G; H40R; T71P; M206F | 49.1 | ii |
| 61/62 | H40R; G94A; M206F | 68.9 | ii |
| 63/64 | H40R; G94S; M206F | 107.6 | ii |
| 65/66 | H40R; N131S; M206F | 35.5 | ii |
| 67/68 | H40R; D150Y; M206F | 48.7 | ii |
| 69/70 | H40R; T152G; M206F | 55.7 | ii |
| 71/72 | H40R; N157C; M206F | 313.9 | ii |
| 73/74 | H40R; M195G; M206F | 500.9 (opposite d.r.) | ii |
| 75/76 | H40R; V113I; M206F | 19.0 | ii |
| 77/78 | H40R; L196M; M206F | 74.2 | ii |
| 79/80 | H40R; M206F; W249G | 27.5 | ii |
| 81/82 | L17M; H40R; A64V; V87L; V96Y; M147L; Y199H; M206F | 154.8 | ii |
| 83/84 | L17M; H40R; V87L; M147L; D173L; Y199H; M206F | 202.6 | ii |
| 85/86 | L17M; H40R; A64V; V87L; M147Q; D173L; Y199H; M206F | 587.4 | ii |
| 87/88 | L17M; H40R; V87L; V96L; Y199H; M206F | 147.9 | ii |
| 89/90 | L17M; H40R; V96L; M147Q; M206F | 90.5 | ii |
| 91/92 | L17M; H40R; A64V; V87L; V96Y; M147Q; Y199H; M206F | 71.4 | ii |
| 93/94 | L17M; H40R; V87L; V96L; M147Q; Y199H; M206F | 100.3 | ii |
| 95/96 | H40R; V96L; M147Q; D173L; M206F | 38.6 | ii |
| 97/98 | H40R; Y199H; M206F | 63.6 | ii |
| 99/100 | H40R; V87L; M147Q; D173L; M206F | 27.3 | ii |
| 101/102 | H40R; M147Q; M206F | 31.7 | ii |
| 103/104 | L17M; H40R; V87L; V96Y; D173L; M206F | 40.8 | ii |
| 105/106 | L17M; H40R; A64V; Y199H; M206F; N221S | 351.6 | ii |
| 107/108 | L17M; H40R; M206F | 101.0 | ii |
| 109/110 | L17M; H40R; A64V; V96Y; M147I; D173L; Y199H; M206F | 241.2 | ii |
| 111/112 | L17M; H40R; V96L; M147Q; M206F; W249Y | 213.1 | ii |
| 113/114 | L17M; H40R; A64V; M147Q; D173L; Y199H; M206F | 242.0 | ii |
| 115/116 | L17M; H40R; A64V; V87L; V96Y; M147I; D173L; M206F | 257.8 | ii |
| 117/118 | H40R; A64V; V87L; V96Y; M147Q; Y199H; M206F; W249Y | 91.7 | ii |
| 119/120 | L17M; H40R; A64V; M147Q; Y199H; M206F; W249F | 612.5 | ii |
| 121/122 | L17M; H40R; A64V; M147Q; D173L; M206F | 211.7 | ii |
| 123/124 | H40R; A64V; M147Q; D173L; Y199H; M206F | 89.7 | ii |
| 125/126 | L17M; H40R; A64V; M147L; M206F | 267.4 | ii |
| 127/128 | L17M; H40R; V87L; M147Q; Y199H; M206F | 170.2 | ii |
| 129/130 | L17M; H40R; A64V; V96L; M147I; Y199H; M206F; | 444.1 | ii |
| 131/132 | G7S; H40R; V60I; A64V; Q127R; M206F; H216R; V245I | 185.7 | ii |
| 133/134 | L17R; H40R; A64V; T71P; G94P; I144V; M147I; N157C; L196M; D198S; M206F; F243S | 8985.6 | iii |
| 135/136 | L17R; H40R; A64V; T71P; V87L; G94P; I144V; M147I; D150Y; N157C; L196M; D198S; M206F | 11808.6 | iii |
| 137/138 | L17Q; H40R; A64V; V87L; G94P; V95M; I144V; M147I; D150Y; N157C; L196M; D198S; M206F | 11931.9 | iii |
| 139/140 | L17R; H40R; A64V; V87L; G94P; I144V; M147I; D150Y; N157C; L196M; D198S; M206F; Q208R | 11538.1 | iii |
| 141/142 | L17Q; H40R; G94P; I144V; M147I; N157C; L196M; D198S; M206F; W249Y | 12100.3 | iii |
| 143/144 | L17M; H40R; A64V; T71P; G94P; I144V; M147I; N157C; L196M; D198S; M206F; W249Y | 11180.5 | iii |
| 145/146 | L17Q; H40R; A64V; T71P; G94P; V95M; I144V; M147I; N157C; L196M; M206F | 5635.6 | iii |
| 147/148 | L17R; H40R; A64V; G94P; I144V; M147Q; D150Y; N157C; L196M; M206F | 9200.2 | iii |
| 149/150 | L17M; H40R; A64V; T71P; G94P; I144V; M147I; N157C; L196M; D198S; M206F | 8707.5 | iii |
| 151/152 | L17R; H40R; T71P; V87L; G94P; I144V; M147I; D150Y; N157C; L196M; M206F | 7487.5 | iii |
| 153/154 | L17M; H40R; A64V; T71P; G94P; E105G; I144V; M147I; D150Y; N157C; L196M; Y199H; M206F | 6634.1 | iii |
| 155/156 | L17R; H40R; G94P; I144V; M147I; N157C; L196M; D198S; Y199H; M206F | 5827.1 | iii |
| 157/158 | L17R; H40R; A64V; G94P; V95M; I144V; D150Y; L196M; M206F; W249Y | 10168.4 | iii |
| 159/160 | L17Q; H40R; G94P; V95M; I144V; M147Q; L196M; D198S; Y199H; M206F; W249F | 5869.0 | iii |
| 161/162 | L17Q; H40R; A64V; V87L; G94P; I144V; M147I; N157C; L196M; D198S; Y199H; M206F | 6201.2 | iii |
| 163/164 | L17Q; F27L; H40R; A64V; T71P; G94P; V95M; I144V; M147I; L196M; D198S; M206F; W249Y | 5838.0 | iii |
| 165/166 | L17Q; H40R; A64V; T71P; G94P; I144V; N157C; L196M; M206F; W249Y | 5883.6 | iii |

TABLE 2A-continued

| SEQ ID NO: (nt/aa) | Amino Acid Differences (relative to SEQ ID NO: 4) | Activity (relative to SEQ ID NO: 4) | Assay[1] |
|---|---|---|---|
| 167/168 | L17R; H40R; T71P; V87L; G94P; I144V; M147I; N157C; L196M; M206F; W249F | 6007.8 | iii |
| 169/170 | L17Q; H40R; A64V; T71P; G94P; I144V; M147I; L196M; D198S; M206F | 5487.0 | iii |
| 171/172 | L17R; H40R; A64V; G94P; V95M; I144V; N157C; L196M; Y199H; M206F; W249F | 8629.4 | iii |

[1]HTP assay conditions:
i: Cells were lysed by shaking for 1 h at 250 rpm and room temperature in 300 μL of lysis buffer containing 0.2M borate, 0.5 g/L lysozyme, and 0.4 g/L polymyxin B sulfate at pH 10.5. The reaction conditions comprised: 20 g/L substrate compound (2), 60 μL clear cell lysate from cells containing the ketoreductase polypeptide lysed in 300 μL lysis buffer, 30% IPA (v/v), 0.5 g/L NADP, 0.2M borate, pH 9.5 and incubated at 35° C. for 24 h.
ii: Cells were lysed by shaking for 1 h at 250 rpm and room temperature in 300 μL of lysis buffer containing 0.2M borate, 0.5 g/L lysozyme, and 0.4 g/L polymyxin B sulfate at pH 10.5. The reaction conditions comprised: 50 g/L substrate compound (2), 20 μL clear cell lysate from cells containing the ketoreductase polypeptide lysed in 300 μL lysis buffer, 50% IPA (v/v), 0.1 g/L NADP, 0.2M borate, pH 10 and incubated at 45° C. for 24 h.
iii: Cells were lysed by shaking for 1 h at 250 rpm and room temperature in 300 μL of lysis buffer containing 0.2M borate, 0.5 g/L lysozyme, and 0.4 g/L polymyxin B sulfate at pH 10.5. The reaction conditions comprised: 50 g/L substrate compound (2), 40 μL clear cell lysate from cells containing the ketoreductase polypeptide lysed in 300 uL lysis buffer, 50% IPA (v/v), 0.1 g/L NADP, 0.2M borate, pH 10 and incubated at 55° C. for 24 h.

TABLE 2B

| SEQ ID NO: (nt/aa) | Amino Acid Differences (relative to SEQ ID NO: 4) | Activity (relative to SEQ ID NO: 4) | d.r. | Assay[2] |
|---|---|---|---|---|
| 3/4 | n/a | 1.0 | 25 | A |
| 5/6 | V96L | 6.5 | 15 | A |
| 7/8 | M195A | 4.5 | 11 | A |
| 9/10 | M206F | 7.0 | 39 | A |
| 11/12 | H40R; V96L | 33.0 | 9 | B |
| 13/14 | H40R; M206F | 37.4 | 15 | B |
| 15/16 | H40R; M195A | 16.0 | 7 | B |
| 13/14 | H40R; M206F | 3.5 | >100 | C |
| 17/18 | H40R; G94P; M206F | 28.3 | >100 | C |
| 19/20 | H40R; V95M; M206F | 18.2 | 83 | C |
| 21/22 | H40R; I144V; M206F | 18.1 | 55 | C |
| 23/24 | H40R; L196M; M206F | 36.9 | >100 | C |
| 25/26 | H40R; D198S; M206F | 51.9 | >100 | C |
| 27/28 | H40R; A64V; V87L; M147Q; Y199H; M206F | 27.2 | 51 | C |
| 29/30 | H40R; A64V; M147Q; Y199H; M206F | 20.0 | 34 | C |
| 31/32 | H40R; G94P; I144V; L196M; M206F | No activity in 45° C. assay | n/a | D |
| 33/34 | L17Q; H40R; A64V; T71P; G94P; V95M; T122A; I144V; M147I; N157C; L196M; D198S; M206F; W249Y | 345.6 | >100 | D |
| 35/36 | L17Q; H40R; A64V; T71P; G94P; 144V; M147I; N157C; L196M; M206F; W249F | 341.7 | >100 | D |
| 37/38 | L17M; H40R; A64V; V87L; G94P; I144V; N157C; L196M; D198S; Y199H; M206F; W249F | 343.1 | 78 | D |
| 39/40 | L17R; H40R; A64V; V87L; G94P; I144V; M147I; D150Y; N157C; L196M; D198S; M206F | 234.4 | >100 | D |
| 41/42 | L17Q; I23V; H40R; A64V; T71P; V87L; G94P; V95M; I144V; M147I; T153G; N157C; L196M; D198S; M206F; W249F | 341.3 | 83 | D |
| 43/44 | L17R; H40R; A64V; T71P; G94P; V95M; I144V; D150Y; L196M; D198S; M206F | 203.4 | >100 | D |

[2]SFP Assay Conditions:
A: In a 2 mL vial: 5 g/L substrate compound (2), 5 g/L SFP of ketoreductase polypeptide, 30% IPA (v/v), 0.5 g/L NADP, 0.2M borate, pH 9.5 (buffer) and incubated at 35° C. for 24 h.
B: In a 2 mL vial: 5 g/L substrate compound (2), 5 g/L SFP of ketoreductase polypeptide, 30% IPA (v/v), 0.5 g/L NADP, 0.2M borate pH 9.5 (buffer) and incubated at 35° C. 6 h.
C: In a 2 mL vial: 40 g/L substrate compound (2), 5 g/L SFP of ketoreductase polypeptide, 50% IPA (v/v), 0.1 g/L NADP, 0.2M borate, pH 10.2 (reaction) and incubated at 35° C. for 24 h.
D: In a 2 mL vial: 40 g/L substrate compound (2), 2 g/L SFP of ketoreductase polypeptide, 50% IPA (v/v), 0.1 g/L NADP, 0.2M borate, pH 10 (buffer) and incubated at 45° C. for 22 h.

TABLE 2C

| SEQ ID NO: (nt/aa) | Amino Acid Differences (relative to SEQ ID NO: 4) | Activity (relative to SEQ ID NO: 4) | d.r. | Assay[3] |
|---|---|---|---|---|
| 3/4 | n/a | 1.0 | >100 | E |
| 9/10 | M206F | 6.0 | >100 | E |
| 13/14 | H40R; M206F | 29.7 | 30 | E |
| 13/14 | H40R; M206F | 80.7 | 14 | F |
| 17/18 | H40R; G94P; M206F | 73.5 | >100 | F |
| 21/22 | H40R; I144V; M206F | 253.1 | 42 | F |
| 23/24 | H40R; L196M; M206F | 264.0 | >100 | F |
| 25/26 | H40R; D198S; M206F | 74.9 | >100 | F |
| 31/32 | H40R; G94P; I144V; L196M; M206F | 470.5 | 51 | F |
|  |  | No activity in 45° C. assay | n/a | G |
| 33/34 | L17Q; H40R; A64V; T71P; G94P; V95M; T122A; I144V; M147I; N157C; L196M; D198S; M206F; W249Y | 1629.1 | >100 | G |
| 35/36 | L17Q; H40R; A64V; T71P; G94P; I144V; M147I; N157C; L196M; M206F; W249F | 1620.0 | >100 | G |
| 37/38 | L17M; H40R; A64V; V87L; G94P; I144V; N157C; L196M; D198S; Y199H; M206F; W249F | 1660.0 | 87 | G |
| 41/42 | L17Q; I23V; H40R; A64V; T71P; V87L; G94P; V95M; I144V; M147I; T153G; N157C; L196M; D198S; M206F; W249F | 1669.1 | 88 | G |

[3]DSP Assay Conditions:
E: 100 g/L substrate compound (2), 5 g/L DSP powder of ketoreductase polypeptide, 30% IPA (v/v), 0.1 g/L NADP, 0.2M borate, pH 9.5 (buffer), and incubated at 35° C. for 24 h.
F: 40 g/L substrate compound (2), 1 g/L DSP powder of ketoreductase polypeptide, 50% IPA (v/v), 0.1 g/L NADP, 0.2M borate, pH 10.3 (reaction), and incubated at 35° C. for 22 h.
G: 100 g/L substrate compound (2), 1 g/L DSP powder of ketoreductase polypeptide, 50% IPA (v/v), 0.1 g/L NADP, 0.2M borate, pH 10.0 (buffer) and incubated at 45° C. for 22 h.

In light of the properties of the exemplary polypeptides, improvements in enzyme properties (e.g., activity in conversion of compound (2) to compounds (1a) and (1c)) are associated with residue differences as compared to SEQ ID NO:4 at residue positions X7; X17; X23; X27; X29; X40; X60; X64; X71; X87; X94; X95; X96; X105; X113; X122; X127; X131; X144; X145; X147; X150; X152; X153; X157; X173; X195; X196; X198; X199; X206; X208; X216; X221; X243; X245; and X249. The specific residue differences at each of these positions that are associated with the improved properties include: X7S; X17M; X17Q; X17R; X23V; X27L; X29G; X40R; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X206F; X206L; X208R; X216R; X221S; X243S; X245I; X249F; X249G; and X249Y. Increases in enzyme activity are associated with residue differences at residue positions X60; X71; X94; X95; X96; X127; X144; X152; X196; X199; X206; X216; and X245. Substrate binding function which affects, in part, enzyme activity and diastereoselectivity, particularly formation of product compounds (1a) and (1c) over compounds (1b) and (1d), are associated with residue differences at residue positions X40; X94; X95; X96; X144; X145; X150; X152; X153; X157; X195; X196; X198; X199; X206; and X249. Cofactor NADP binding is associated with residue differences at residue position X40 and affects enzyme activity. Increases in the diastereomeric ratio of compounds (1a) and (1c) over compounds (1b) and (1d) are associated with residue differences at residue positions X17; X64; X71; X87; X147; X157; X196; X206 and X249. Some decrease in diastereomeric ratio is associated with residue differences at residue position X144, but the reduction in d.r. is compensated by a significant increase in enzyme activity. Change in diastereoselectivity to formation of compounds (1b) and (1d) in diastereomeric excess over compounds (1a) and (1c) is associated with X195G. Increases in enzyme stability, particularly at increased temperature (e.g., activity at 35° C. versus activity at 45° C.), are associated with, among others, residue differences at residue positions X17; X64; X71; X87; X94; X147; X147; X147; X157, X198; and X249. As will be appreciated by the skilled artisan, the foregoing residue positions and the specific amino acid residues for each residue position can be used individually or in various combinations to synthesize engineered ketoreductase polypeptides having desired improved properties, including, among others, enzyme activity, stereoselectivity and stability.

In light of the guidance provided herein, it is further contemplated that any of the exemplary engineered polypeptides of SEQ ID NO: 4, 6, 8, 10, 12, 14, 16, 18, 20, 22, 24, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 96, 98, 102, 104, 106, 108, 110, 114, 116, 122, 124, 126, 128, 130, 132, 136, 138, 140, 142, 144, 146, 148, 150, 152, 154, 156, 158, 160, 162, 164, 168, 170 and 172, and in particular the engineered polypeptides of SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172 can be used as the starting amino acid sequence for synthesizing other engineered ketoreductase polypeptides, for example by subsequent rounds of evolution by adding new combinations of various amino acid differences from other polypeptides in Tables 2A, 2B and 2C, and other residue positions described herein. Further improvements may be generated by including amino acid differences at residue positions that had been maintained as unchanged throughout earlier rounds of evolution.

Accordingly, in some embodiments, the ketoreductase polypeptide capable of carrying out the conversion of substrate compound (2), tert-butyl(1-oxo-1-phenylhex-5-yn-2-yl)carbamate, to the product compound (1), tert-butyl(1- hydroxy-1-phenylhex-5-yn-2-yl)carbamate, with at least 1.5 fold the activity of polypeptide SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and the features X40R and X206L or F, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y.

In some embodiments, the ketoreductase polypeptide capable of carrying out the conversion of substrate compound (2) to the product compound (1) with at least 1.5 fold the activity of polypeptide SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more identity to reference sequence SEQ ID NO:2 and the features X40R and X206L or F, with the proviso that when X206 is F, the sequence further comprises one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y.

In some embodiments, the ketoreductase polypeptide capable of converting substrate compound (2) to product compound (1) with at least 1.5 fold the activity of polypeptide SEQ ID NO:4, comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and having the features X40R and X206L or F, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y, and in particular one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y.

In some embodiments, the reference sequence is selected from SEQ ID NO: 4, 14, 36, 42, and 130. In some embodiments, the reference sequence is SEQ ID NO:4. In some embodiments, the reference sequence is SEQ ID NO:36. In some embodiments, the reference sequence is SEQ ID NO:42. In some embodiments, the reference sequence is SEQ ID NO:130.

In some embodiments, the engineered ketoreductase polypeptide having the amino acid sequence identity to a reference sequence as described above comprises the features X40R and X206L.

In some embodiments, the engineered ketoreductase comprises an amino acid sequence having the features X40R and X206L and one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y.

In some embodiments, the engineered ketoreductase polypeptide having the amino acid sequence identity to a reference sequence as described above comprises the features X40R and X206F and one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y.

In some embodiments, the engineered ketoreductase polypeptide having the amino acid sequence identity to a reference sequence as described above comprises the features X40R and X206F, and one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y.

In some embodiments, the engineered ketoreductase polypeptide having the features X40R and X206F, and one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y can further comprise one or more residue differences as compared to SEQ ID NO:4 selected from: X60I, X144V; X145L; and X245I.

In some embodiments, the engineered ketoreductase with the features X40R and X206F and one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y comprises an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase comprises an amino acid sequence having the features X40R and X206F or L and at least one or more residue differences as compared to SEQ ID NO:4 selected from: X17Q/R/M; X64V; X94P; X144V; X147Q/I/L; X157C; and X196M. In some embodiments, the engineered ketoreductase comprises an amino acid sequence having the features X40R and X206F/L and at least X17Q. In some embodiments, the engineered ketoreductase comprises an amino acid sequence having the features X40R and X206F/L and at least X64V. In some embodiments, the engineered ketoreductase comprises an amino acid sequence having the features X40R and X206F/L and at least X94P. In some embodiments, the engineered ketoreductase comprises an amino acid sequence having the features X40R and X206F/L and at least X144V. In some embodiments, the engineered ketoreductase comprises an amino acid sequence having the features X40R and X206F/L and at least X147I. In some embodiments, the engineered ketoreductase comprises an amino acid sequence having the features X40R and X206F/L and at least X157C. In some embodiments, the engineered ketoreductase comprises an amino acid sequence having the features X40R and X206F/L and at least X196M. In each of the foregoing embodiments, additional residue differences at other residue positions described herein can be present in the engineered ketoreductase.

In some embodiments, the engineered ketoreductase comprises an amino acid sequence having at least a combination of residues differences as compared to SEQ ID NO:4 selected from: (a) X40R, X196M, and X206F/L; (b) X40R, X144V, and X206F/L; (c) X40R, X17H/R/Q, and X206F/L; (d) X40R, X94P, and X206F/L; (e) X40R, X196M, and X206F/L; (f) X40R, X198S, and X206F/L; (g) X40R, X17H/R/Q, X94P and X206F/L; (h) X40R, X71P, X157C and X206F/L; (i) X40R, X94P, X144V, X196M and X206F/L; (j) X17H/R/Q, X40R, X64V, X147I/Q/L, and X206F/L; (k) X17H/R/Q, X40R, X64V, X94P, X144V, X147I/Q/L, X157C, X196M and X206F/L; and (l) X17Q, X40R, X64V, X71P, X94P, X144V, X147I, X157C, X196M, X206F, and X249F.

In some embodiments, the engineered ketoreductase polypeptide is capable of converting the substrate compound (2), tert-butyl(1-oxo-1-phenylhex-5-yn-2-yl)carbamate, to the product compound (1), tert-butyl(1-hydroxy-1-phenylhex-5-yn-2-yl)carbamate, with at least 2 fold, 3 fold, 4 fold, 5 fold, 10 fold, 20 fold, 30 fold, 40 fold, 50 fold, 100 fold, 200 fold, 500 fold, 1000 fold, 5000 fold, 10000 fold or more activity relative to the activity of the reference polypeptide of SEQ ID NO: 4. In some embodiments, the engineered ketoreductase polypeptide capable of converting the substrate compound (2) to the product compound (1) with at least 2 fold, 3 fold, 4 fold, 5 fold, 10 fold, 20 fold, 30 fold, 40 fold, 50 fold, 100 fold, 200 fold, 500 fold, 1000 fold, 5000 fold, 10000 fold or more the activity of the reference polypeptide of SEQ ID NO:4 comprises an amino acid sequence having the features H40R and X206F or L, and one or more residue differences as compared to SEQ ID NO:4 selected from: X60I; X71P; X94P; X94A; X95M; X96L; X96Y; X127R; X144V; X145I; X150Y; X152G; X153G; X157C; X195A; X195G; X196M; X198S; X199H; X206F, X216R, X245I, X245F; X249Y; and X249F.

In some embodiments, the engineered ketoreductase polypeptide capable of converting the substrate compound (2) to the product compound (1) with at least 10 fold the activity of reference polypeptide of SEQ ID NO:4, as measured under HTP conditions, comprises an amino acid sequence selected from SEQ ID NO: 18, 20, 22, 24, 26, 28, 30, 34, 36, 38, 40, 42, 44, 50, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase is capable of converting compound (2) to compound (1) with at least 100 fold the activity of SEQ ID NO:4 as measured under HTP conditions. In some embodiments, the engineered ketoreductase capable of converting compound (2) to compound (1) with at least 100 fold the activity of SEQ ID NO:4 comprises an amino acid sequence selected from SEQ ID NO: 34, 36, 38, 40, 42, 44, 134, 136, 138, 140, 142, 144, 146, 148, 150, 152, 154, 156, 158, 160, 162, 164, 166, 168, 170 and 172.

In some embodiments, the engineered ketoreductase capable of converting compound (2) to compound (1) has increased thermal stability as compared to the reference polypeptide of SEQ ID NO:4 or 32. In some embodiments, the engineered ketoreductase polypeptide with increased thermostability comprises an amino acid sequence having one or more residue differences as compared to SEQ ID NO:4 selected from: X17Q; X17R; X17W; X64V; X71P; X87L; X94S; X94P; X147Q; X147I; X147L; X157C, X198S; X249Y; and X249F. In some embodiments, the engineered ketoreductase having increased thermal stability comprises an amino acid sequence having the features H40R and X206F or L, and one or more residue differences as compared to SEQ ID NO:4 selected from: X17Q; X17R; X17W; X64V; X71P; X87L; X94S; X94P; X147Q; X147I; X147L; X157C, X198S; X249Y; and X249F.

In some embodiments, the engineered ketoreductase polypeptides disclosed herein are capable of forming product syn-tert-butyl(1-hydroxy-1-phenylhex-5-yn-2-yl)carbamate compounds (1a) and (1c)

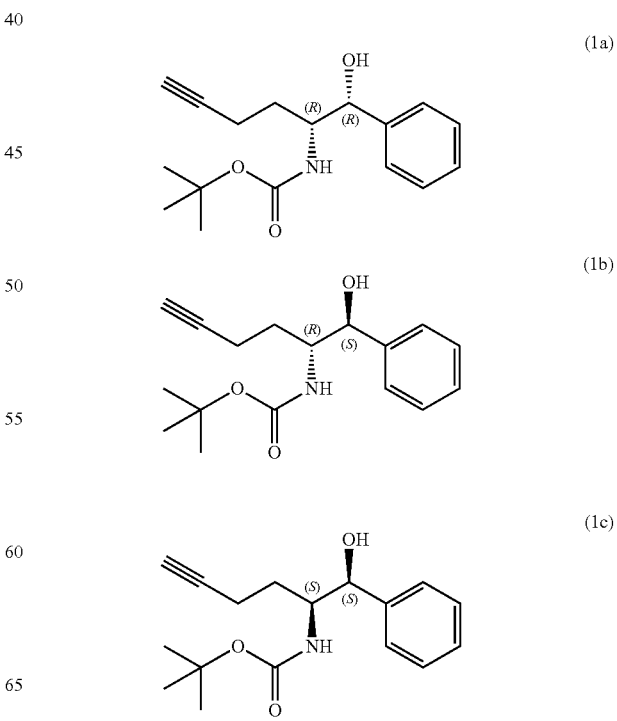

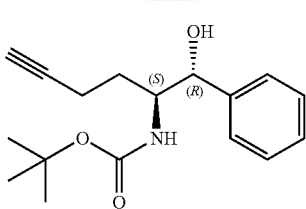

(1d)

in diastereomeric excess of anti-tert-butyl(1-hydroxy-1-phenylhex-5-yn-2-yl)carbamate compounds (1b) and (1d). In some embodiments, the engineered ketoreductase polypeptide diastereoselective for product compounds (1a) and (1c) over compounds (1b) and (1d) comprises an amino acid sequence having the features X40R and 206F or L, and one or more residue differences as compared to SEQ ID NO:4 selected from: X17Q; X64V; X71P; X87L; X147I; X157C; X196M; and X249F.

As noted above, the exemplary engineered ketoreductases indicate that the presence of X195G alters diastereoselectivity to favor formation of product compounds (1b) and (1d) over product compounds (1a) and (1c). Accordingly, in some embodiments of the engineered ketoreductase polypeptides diastereoselective for product compounds (1a) and (1c) over product compounds (1b) and (1d), the presence of X195G is disfavored.

In some embodiments, the engineered ketoreductase polypeptide diastereoselective for product compounds (1a) and (1c) over compounds (1b) and (1d) comprises an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase is capable of forming product compounds (1a) and (1c) in a diastereomeric ratio of at least 50 over compounds (1b) and (1d). In some embodiments, the engineered ketoreductase capable of forming product compounds (1a) and (1c) in a diastereomeric ratio of at least 50 over compounds (1b) and (1d) comprises an amino acid sequence selected from SEQ ID NO: 18, 20, 22, 24, 26, 28, 32, 34, 36, 38, 40, 42 and 44.

In some embodiments, the engineered ketoreductases are capable of forming product compound (1a) in diastereomeric excess over product compound (1c). The amino acid sequences of ketoreductases with diastereoselectivity for compound (1a) over compound (1c) have features similar to the engineered ketoreductases having diastereoselectivity for compounds (1a) and (1c) over compounds (1b) and (1d). Accordingly, in some embodiments, the engineered ketoreductase polypeptide diastereoselective for product compound (1a) over compound (1c) comprises an amino acid sequence having the features X40R and 206F or L, and one or more residue differences as compared to SEQ ID NO:4 selected from: X17Q; X64V; X71P; X87L; X147I; X157C; X196M; and X249F.

In some embodiments, the engineered ketoreductase polypeptides capable of forming product compound (1a) in diastereomeric excess over compound (1c) comprises an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase polypeptides are capable of forming product compounds (1b) and (1d) in diastereomeric excess of compounds (1a) and (1c). In some embodiments, the engineered ketoreductase capable of forming product compounds (1b) and (1d) in diastereomeric excess of compounds (1a) and (1c) comprises an amino acid sequence having at least 80%, 85%, 86%, 87%, 88%, 89%, 90%, 91%, 92%, 93%, 94%, 95%, 96%, 97%, 98%, 99% or more identity to the reference sequence of SEQ ID NO: 4 and having the feature X195G.

In some embodiments, the engineered ketoreductase capable of forming product compounds (1b) and (1d) in diastereomeric excess of compounds (1a) and (1c) comprises an amino acid sequence having the features X40R and X206F or L, and X195G.

In some embodiments, the engineered ketoreductase capable of forming product compounds (1b) and (1d) in diastereomeric excess of compounds (1a) and (1c) comprises an amino acid sequence selected from SEQ ID NO: 50 and 74.

In some embodiments, the engineered ketoreductase capable of converting compound (2) to compound (1) under suitable reaction conditions, comprises an amino acid sequence having at least 80%, 85%, 86%, 87%, 88%, 89%, 90%, 91%, 92%, 93%, 94%, 95%, 96%, 97%, 98%, or 99% identity to one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and the amino acid residue differences as compared to SEQ ID NO:4 present in any one of SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172. In some embodiments, residue differences present in one or more of amino acid sequences selected from SEQ ID NO: 6, 8, 10, 12, 14, 16, 46, 48, 50, 52, and 54 are specifically excluded from the foregoing embodiments.

Accordingly, in some embodiments, the engineered ketoreductase polypeptide capable of converting compound (2) to compound (1) under suitable reaction conditions, comprises an amino acid sequence having at least 80%, 85%, 86%, 87%, 88%, 89%, 90%, 91%, 92%, 93%, 94%, 95%, 96%, 97%, 98%, or 99% identity to one of SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and the amino acid residue differences as compared to SEQ ID NO:4 present in any one of SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In addition to the residue positions specified above, any of the engineered ketoreductase polypeptides disclosed herein can further comprise residue differences relative to the reference polypeptide sequence of SEQ ID NO: 2 or 4 at other residue positions, i.e., residue positions other than X7; X17; X23; X27; X29; X60; X64; X71; X87; X94; X95; X96; X105; X113; X122; X127; X131; X144; X145; X147; X150; X152; X153; X157; X173; X195; X196; X198; X199; X208; X216; X221; X243; X245; and X249. Residue differences at these other residue positions can provide for additional variations in the amino acid sequence without altering the polypeptide's ability to convert substrate compound (2) to product compound (1), in particular with regards to increased activity for forming compounds (1a) and (1c); diastereoselectivity for product compounds (1a) and (1c) over compounds (1b) and (1d); diastereoselectivity for product compound (1a) over compound (1c); and diastereoselectivity for product compounds (1b) and (1d) over compounds (1a) and (1c). Accordingly, in some embodiments, in addition to the amino acid residue differences of any one of the engineered ketoreductase polypeptides selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO:4. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. In some embodiments, the residue differences at other amino acid residue positions can comprise conservative substitutions and/or non-conservative substitutions as compared to a reference sequence of the wild-type polypeptide of SEQ ID NO: 2 or the engineered ketoreductase polypeptide of SEQ ID NO: 4.

Amino acid residue differences at other positions relative to the wild-type sequence of SEQ ID NO: 2 and the effect of these differences on enzyme function are described for other engineered ketoreductase polypeptides disclosed in published PCT applications WO2008103248, WO2009029554, WO2009036404, WO2009042984, WO2010027710, WO2010025238, WO2010025287, WO2010025085, WO/2009/046153, WO2011022548; and WO2011/140219; and U.S. provisional application No. 61/475,103, filed Apr. 13, 2011; each of which is hereby incorporated by reference herein. Accordingly, in some embodiments, one or more of the amino acid differences as compared to the sequence of SEQ ID NO: 2 or 4 can also be introduced into a engineered ketoreductase polypeptide of the present disclosure at residue positions selected from X2; X3; X4; X8; X9; X10; X11; X12; X16; X19; X21; X25; X41; X42; X43; X45; X46; X49; X53; X54; X57; X60; X66; X68; X72; X74; X75; X76; X77; X78; X80; X82; X86; X93; X97; X99; X100; X101; X104; X106; X108; X109; X111; X112; X117; X120; X124; X125; X126; X129; X134; X141; X144; X145; X148; X149; X151; X155; X159; X163; X165; X169; X176; X177; X178; X179; X185; X186; X190; X192; X194; X197; X200; X201; X202; X203; X204; X205; X207; X210; X211; X212; X214; X217; X223; X225; X226; X228; X233; X235; X236; X245; X248; X250; and X251. In particular, the choices of amino acid residues at the forgoing positions can be selected from the following:; X2A/S; X3Y/N/V; X4C; X8R/N; X9G; X10T; X11V/T/F/L; X12I; X16A/G/V/S; X19V; X21F/R; X25N/R/T; X41V/T; X42G; X43A/I/R; X45G; X46R; X49R; X53D/V; X54A; X57V; X60A/I; X66E; X68V; X72R/E/T; X74L; X75N; X76A/I; X77A; X78D; X80T/V; X82S; X86I; X93S/A/T; X97G/E/L/H/I/M/R/T/V; X99L; X100K; X101G/N; X104M; X106G/D; X108H/N/S/D/K; X109R/E; X111M; X112D; X117S/A/G; X120V; X124Q; X125S; X126V; X129T; X134M; X141V; X144V; X145D/S/L/Q/F/Y/A/M/V/K; X148I; X149F; X151A; X155C; X159T; X163I; X165T/N; X169C; X176V; X177R; X178G; X179F; X185S; X186I; X190A/C/P/H/G/F/N/L/E/I/V; X192E/R; X194D/G/N/L/Q/S/R; X197G/E/V/A; X200K/P; X201A/I/L; X202G/I/L/M/W/Y/V/F/N; X203G; X204A/V; X205T/R/V; X207C/I/N/T; X210R; X211R/I/L/T/V; X212S/V; X214T/V; X217F; X223V/G/I; X225V; X226L/T/V; X228A; X233A/G; X235W; X236R; X245I; X248K/R; X250I/Y; and X251T. Guidance on the choice of the amino acid residues at the residue positions can be found in the cited references.

In some embodiments, the present disclosure also provides engineered ketoreductase polypeptides that comprise a fragment of any of the engineered ketoreductase polypeptides described herein that retains the functional activity and/or improved property of that engineered ketoreductase. Accordingly, in some embodiments, the present disclosure provides a polypeptide fragment capable of converting compound (2) to compound (1) under suitable reaction conditions, wherein the fragment comprises at least about 80%, 90%, 95%, 98%, or 99% of a full-length amino acid sequence of a engineered ketoreductase polypeptide of the present disclosure, such as an exemplary engineered ketoreductase polypeptide selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular an exemplary engineered polypeptide selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the engineered ketoreductase polypeptide of the disclosure can have an amino acid sequence comprising a deletion of any one of the engineered ketoreductase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular an exemplary engineered polypeptide selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172. Thus, for each and every embodiment of the engineered ketoreductase polypeptides of the disclosure, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, where the associated functional activity and/or improved properties of the engineered ketoreductase described herein is maintained. In some embodiments, the deletions can comprise, 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered ketoreductase polypeptide of the disclosure can have an amino acid sequence comprising an insertion as compared to any one of the engineered ketoreductase polypeptides described herein, such as the exemplary engineered polypeptides of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular an exemplary engineered polypeptide selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172. Thus, for each and every embodiment of the ketoreductase polypeptides of the disclosure, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered ketoreductase described herein is maintained. The insertions can be to amino or carboxy terminus, or internal portions of the ketoreductase polypeptide.

In some embodiments, the present disclosure provides an engineered ketoreductase polypeptide capable of converting compound (2) to compound (1) under suitable reaction conditions, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular an exemplary engineered polypeptide selected from SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, with the proviso that the amino acid sequence is not identical to (that is, it excludes) any of the exemplary engineered ketoreductase polypeptides amino acid sequences disclosed in published PCT applications WO2008103248, WO2009029554, WO2009036404, WO2009042984, WO2010027710, WO2010025238, WO2010025287, WO2010025085, WO2009046153, WO2011022548; and WO2011/140219; and U.S. provisional application No. 61/475,103, filed Apr. 13, 2011; each of which is hereby incorporated by reference herein.

In the above embodiments, the suitable reaction conditions for the engineered polypeptides can be those described in Table 2A, 2B and 2C. Accordingly, in some embodiments, the suitable reaction conditions are those described for HTP assays, which comprise: 20 or 50 g/L substrate compound (2); 60 μL, 20 μL, or 40 μL cell lysate containing the engineered ketoreductase; 30% or 50% (v/v) isopropyl alcohol; 0.5 g/L or 0.1 g/L NADP, 0.2 M borate, pH 9.5 or pH10; an incubation temperature of 35° C., 45° C. or 55° C.; and a reaction time of 24 h. Guidance for use of these reaction conditions and the ketoreductase polypeptides are provided in, among others, Table 2A.

In some embodiments, the suitable reaction conditions are those described for shake flask powder (SFP) assays, which comprise: 5 g/L or 40 g/L compound (2), 5 g/L or 2 g/L of ketoreductase polypeptide; 30% or 50% (v/v) isopropyl alcohol; 0.5 or 0.1 g/L NADP; 0.2 M borate, pH 9.5, 10 or 10.2; an incubation temperature of 35° C. or 45° C.; and a reaction time of 6 h or 24 h. Guidance for use of these reaction conditions and the ketoreductase polypeptides are provided in, among others, Table 2B.

In some embodiments, the suitable reaction conditions are those described for downstream process powder (DSP) assays, which comprise: 40 g/L or 100 g/L compound (2), 5 g/L or 1 g/L of ketoreductase polypeptide; 30% or 50% (v/v) isopropyl alcohol; 0.1 g/L NADP; 0.2 M borate, pH 9.5 or 10; an incubation temperature of 35° C. or 45° C.; and an reaction time of 22 h to 24 h. Guidance for use of these reaction conditions and the ketoreductase polypeptides are provided in, among others, Table 2C.

In some embodiments, the polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the engineered ketoreductase polypeptides described herein are not restricted to the genetically encoded amino acids. Thus, in addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg);

cyclohexylalanine (Cha); norleucine (Nle); naphthylalanine (NaI); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered ketoreductase polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having ketoreductase activity of the present disclosure can be immobilized on a solid support such that they retain their improved activity, stereoselectivity, and/or other improved properties relative to the reference polypeptide of SEQ ID NO: 4. In such embodiments, the immobilized polypeptides can facilitate the biocatalytic conversion of the substrate of compound (2) or structural analogs thereof to the product of compound (1) or corresponding structural analogs (e.g., as shown in the processes of Schemes 1, 2 and 3 described herein), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered ketoreductase polypeptides of the present disclosure can be carried out using the same engineered ketoreductase polypeptides bound or immobilized on a solid support.

Methods of enzyme immobilization are well-known in the art. The engineered ketoreductase polypeptide can be bound non-covalently or covalently. Various methods for conjugation and immobilization of enzymes to solid supports (e.g., resins, membranes, beads, glass, etc.) are well known in the art and described in e.g.,: Yi et al., "Covalent immobilization of ω-transaminase from Vibrio fluvialis JS17 on chitosan beads," *Process Biochemistry* 42(5): 895-898 (May 2007); Martin et al., "Characterization of free and immobilized (S)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic*, 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein. Solid supports useful for immobilizing the engineered ketoreductases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered ketoreductases of the present disclosure include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the engineered polypeptides can be provided in the form of kits. The polypeptides in the kits may be present individually or as a plurality of polypeptides. The kits can further include reagents for carrying out enzymatic reactions, substrates for assessing the activity of polypeptides, as well as reagents for detecting the products. The kits can also include reagent dispensers and instructions for use of the kits.

In some embodiments, the polypeptides can be provided on the solid support in the form of an array in which the polypeptides are arranged in positionally distinct locations. The array can be used to test a variety of substrate compounds for conversion by the polypeptides. A plurality of supports can be configured on an array at various locations, addressable for robotic delivery of reagents, or by detection methods and/or instruments. Various methods for conjugation to substrates, e.g., membranes, beads, glass, etc. are described in, among others, Hermanson, G. T., Bioconjugate Techniques, $2^{nd}$ Edition, Academic Press; (2008), and Bioconjugation Protocols: Strategies and Methods, In Methods in Molecular Biology, C. M. Niemeyer ed., Humana Press (2004); the disclosures of which are incorporated herein by reference.

In some embodiments, the kits of the present disclosure include arrays comprising a plurality of different engineered ketoreductase polypeptides disclosed herein at different addressable position, wherein the different polypeptides are different variants of a reference sequence each having at least one different improved enzyme property. Such arrays comprising a plurality of engineered polypeptides and methods of their use are described in WO2009008908.

5.4. Polynucleotides, Expression Vectors, and Host Cells Useful for Preparing Engineered Ketoreductase Polypeptides In another aspect, the present disclosure provides polynucleotides encoding the non-naturally occurring ketoreductase polypeptides described herein. These polynucleotides may be operatively linked to one or more heterologous regulatory sequences that control gene expression to create a recombinant polynucleotide capable of expressing the ketoreductase polypeptide. Expression constructs containing a heterologous polynucleotide encoding the engineered ketoreductase polypeptide can be introduced into appropriate host cells to express the corresponding polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved ketoreductase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2A, 2B and 2C, and disclosed in the sequence listing incorporated by reference herein as SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the polynucleotides can be selected and/or engineered to comprise codons that are preferably selected to fit the host cell in which the protein is being produced. For example, preferred codons used in bacteria are used to express the gene in bacteria, e.g., E. coli; preferred codons used in yeast are used for expression in yeast; and preferred codons used in mammals are used for expression in mammalian cells. Since not all codons need to be replaced to optimize the codon usage of the ketoreductases (e.g., because the natural sequence can have preferred codons and use of preferred codons may not be required for all amino acid residues), codon optimized polynucleotides encoding the ketoreductase polypeptides may contain preferred codons at about 40%, 50%, 60%, 70%, 80%, or greater than 90% of codon positions of the full length coding region.

In some embodiments, the polynucleotide encodes a non-naturally occurring polypeptide capable of converting compound (2), or structural analogs thereof, to compound (1) or corresponding structural analogs, where the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference sequence selected from SEQ ID NO: 4, 6, 8, 10, 12, 14, 16, 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular to a reference sequence selected from 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the polynucleotide encodes an engineered ketoreductase polypeptide capable of converting compound (2) or a structural analog thereof to compound (1) or corresponding structural analog, and having any of the specified sequence identity to any of the reference polypeptides described herein, and comprises one or more residue differences as compared to SEQ ID NO:2 or 4 at the following residue positions: X7S; X17M; X17Q; X17R; X23V; X27L; X29G; X40R; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X206F; X206L; X208R; X216R; X221S; X243S; X245I; X249F; X249G; and X249Y. As such, in some embodiments, the polynucleotides encode the ketoreductase polypeptides having any of the specified sequence identity to the reference polypeptides described above and comprising the specified residue differences, including sets of residue differences, as provided in the present disclosure.

In some embodiments, the polynucleotide encodes a ketoreductase polypeptide capable of carrying out the conversion of substrate compound (2) to the product compound (1) with at least 1.5 fold the activity of polypeptide SEQ ID NO:4, where the polypeptide comprises an amino acid sequence having at least 80%, 85%, 86%, 87%, 88%, 89%, 90%, 91%, 92%, 93%, 94%, 95%, 96%, 97%, 98%, 99% or more identity to the reference sequence SEQ ID NO: 2 or 4, and the features X40R and X206L or F, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y; in particular one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y.

In some embodiments, the polynucleotide encodes a ketoreductase polypeptide comprising an amino acid sequence having at least a combination or residues differences as compared to SEQ ID NO:4 selected from: (a) X40R, X196M, and X206F/L; (b) X40R, X144V, and X206F/L; (c) X40R, X17H/R/Q, and X206F/L; (d) X40R, X94P, and X206F/L; (e) X40R, X198S, and X206F/L; (f) X40R, X17H/R/Q, X94P and X206F/L; (g) X40R, X71P, X157C and X206F/L; (h) X40R, X94P, X144V, X196M and X206F/L; (i) X17H/R/Q, X40R, X64V, X147I/Q/L, and X206F/L; (j) X17H/R/Q, X40R, X64V, X94P, X144V, X147I/Q/L, X157C, X196M and X206F/L; and (k) X17Q, X40R, X64V, X71P, X94P, X144V, X147I, X157C, X196M, X206F, and X249F.

In some embodiments, the polynucleotide encodes a ketoreductase polypeptide capable of forming product compounds (1a) and (1c) in diastereomeric excess of compounds (1b) and (1d). In some embodiments, the polynucleotide encodes a ketoreductase polypeptide diastereoselective for product compounds (1a) and (1c) over product compounds (1b) and (1d), wherein the ketoreductase polypeptide comprises an amino acid sequence having the features X40R and 206F or L, and one or more residue differences as compared to SEQ ID NO:4 selected from: X17Q; X64V; X71P; X87L; X147I; X157C; X196M; and X249F.

In some embodiments, the polynucleotide encodes a ketoreductase polypeptide diastereoselective for product compounds (1a) and (1c) over compounds (1b) and (1d), wherein the ketoreductase polypeptide comprises an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the polynucleotide encodes an engineered polypeptide capable of converting substrate compound (2) to product compound (1) with activity that is at least 1.2 fold, 1.5 fold, 2 fold, 3 fold, 4 fold, 5 fold, 10 fold, 20 fold, 30 fold, 40 fold, 50 fold, 100 fold, 200 fold, 500 fold, 1000 fold, 5000 fold, 10000 fold or more increased relative to the activity of the reference polypeptide of SEQ ID NO: 4, wherein the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, with the proviso that the amino acid sequence comprises any one of the set of residue differences as compared to SEQ ID NO: 4 contained in any one of the polypeptide sequences of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, and in particular the polypeptide sequences of SEQ ID NO: 18, 20, 22, 24, 26, 28, 30, 32, 34, 36, 38, 40, 42, 44, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172, as listed in Table 2A, 2B and 2C. As discussed herein, in some embodiments, the reference polypeptide is selected from SEQ ID NO: 4, 14, 36, 42, and 130.

In some embodiments, the polynucleotide encoding the ketoreductase polypeptide is selected from SEQ ID NO: 3, 5, 7, 9, 11, 13, 15, 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171, in particular a polynucleotide selected from SEQ ID NO: 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171.

In some embodiments, the polynucleotides are capable of hybridizing under highly stringent conditions to a polynucleotide selected from SEQ ID NO: 3, 5, 7, 9, 11, 13, 15, 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171, or a complement thereof; in particular a polynucleotide selected from SEQ ID NO: 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171, or a complement thereof, where the highly stringently hybridizing polynucleotides encode a non-naturally occurring polypeptide capable of converting compound (2) to compound (1) with at least 1.2 fold, 1.5 fold, 2 fold, 3 fold, 4 fold, 5 fold, 10 fold, 20 fold, 30 fold, 40 fold, 50 fold, 100 fold, 200 fold, 500 fold, 1000 fold, 5000 fold, 10000 fold or more increased activity relative to the activity of the polypeptide of SEQ ID NO: 4.

In some embodiments, the polynucleotides are capable of hybridizing under highly stringent conditions to a polynucleotide encoding a polypeptide comprising an amino acid sequence of SEQ ID NO: 2 or 4 having the features X40R and X206L or F, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y; in particular one or more residue differences as compared to SEQ ID NO:4 selected from: X7S; X17M; X17Q; X17R; X23V; X27L; X29G; X64V; X71P; X87L; X94A; X94P; X94S; X95M; X96L; X96Y; X105G; X113I; X122A; X127R; X131S; X147I; X147L; X147Q; X150Y; X152G; X153G; X157C; X173L; X195A; X195G; X196M; X198S; X199H; X208R; X216R; X221S; X243S; X249F; X249G; and X249Y.

In some embodiments, the polynucleotides encode the polypeptides described herein but have about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase polypeptides described herein. In some embodiments, the reference polynucleotide is selected from SEQ ID NO: 3, 5, 7, 9, 11, 13, 15, 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171; in particular a polynucleotide selected from SEQ ID NO: 17, 19, 21, 23, 25, 27, 29, 31, 33, 35, 37, 39, 41, 43, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169 and 171.

An isolated polynucleotide encoding a non-naturally occurring polypeptide disclosed herein may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2010.

In some embodiments, the control sequences include among others, promoters, leader sequence, polyadenylation sequence, propeptide sequence, signal peptide sequence, and transcription terminator. Suitable promoters can be selected based on the host cells used. Exemplary bacterial promoters include *E. coli* lac operon, *E. coli* trp operon, bacteriophage λ, *Streptomyces coelicolor* agarase gene (dagA), *Bacillus subtilis* levansucrase gene (sacB), *Bacillus lichenifonnis* alpha-amylase gene (amyL), beta-lactamase gene, and tac promoter; exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease, and mutant, truncated, and hybrid promoters thereof, and exemplary yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present disclosure. For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

In some embodiments, the control sequence may also be a signal peptide coding region that codes for an amino acid sequence linked to the amino terminus of a polypeptide and directs the encoded polypeptide into the cell's secretory pathway. The signal sequence typically depends on the type of host cells being used to express the polypeptide. Effective signal peptide coding regions for bacterial host cells are the signal peptide coding regions obtained from the genes for *Bacillus* NClB 11837 maltogenic amylase, *Bacillus stearothennophilus* alpha-amylase, *Bacillus lichenifonnis* subtilisin, *Bacillus licheniformis* beta-lactamase, *Bacillus stearothennophilus* neutral proteases (nprT, nprS, nprM), and *Bacillus subtilis* prsA. Exemplary signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and

*Humicola lanuginosa* lipase. Useful signal peptides for yeast host cells can be from the genes for *Saccharomyces cerevisiae* alpha-factor and *Saccharomyces cerevisiae* invertase.

It may also be desirable to add regulatory sequences, which allow the regulated expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter. Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide of the present disclosure would be operably linked with the regulatory sequence.

Other control sequences, such as leader sequences, polyadenylation sequences, and transcription terminator sequences can use those available in the art (see Sambrook, supra, and Current Protocols in Molecular Biology, supra).

In another aspect, the present disclosure is also directed to a recombinant expression vector comprising a polynucleotide encoding an engineered ketoreductase polypeptide, and one or more expression regulating regions such as a promoter and a terminator, a replication origin, etc., depending on the type of hosts into which they are to be introduced. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The expression vector preferably contains one or more selectable markers, which permit easy selection of transformed cells. A selectable marker is a gene the product of which provides for biocide or viral resistance, resistance to heavy metals, prototrophy to auxotrophs, resistance to chemical agents (e.g., antibiotics) and the like.

In another aspect, the present disclosure provides a host cell comprising a polynucleotide encoding an engineered ketoreductase polypeptide of the present disclosure, the polynucleotide being operatively linked to one or more control sequences for expression of the ketoreductase polypeptide in the host cell. Host cells for use in expressing the ketoreductase polypeptides encoded by the expression vectors of the present invention are well known in the art and include but are not limited to, bacterial cells, such as *E. coli*, *Lactobacillus*, *Streptomyces* and *Salmonella typhimurium* cells; fungal cells, such as yeast cells; insect cells such as *Drosophila* S2 and *Spodoptera* Sf9 cells; animal cells such as CHO, COS, BHK, 293, and Bowes melanoma cells; and plant cells. Exemplary host cells are *Escherichia coli* BL21 and W3110.

Appropriate culture mediums and growth conditions for the above-described host cells are well known in the art. Polynucleotides for expression of the ketoreductase may be introduced into host cells by various methods known in the art (e.g., electroporation, biolistic particle bombardment, liposome mediated transfection, calcium chloride transfection, and protoplast fusion).

In the embodiments herein, the non-naturally occurring, engineered ketoreductase polypeptides and nucleotides encoding such polypeptides can be prepared using methods commonly used by those skilled in the art. As noted above, the naturally-occurring amino acid sequence and corresponding polynucleotide encoding the ketoreductase enzyme of *Lactobacillus kefir* for use in generating engineered ketoreductases are available as Genbank Acc. No. AAP94029.1; GI: 33112056. In some embodiments, the parent polynucleotide sequence is codon optimized to enhance expression of the ketoreductase in a specified host cell.

The engineered ketoreductase polypeptides can be obtained by subjecting the polynucleotide encoding the naturally occurring ketoreductase to mutagenesis and/or directed evolution methods (see, e.g., Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; U.S. Pat. Nos. 6,537,746; 6,117,679; 6,376,246; and 6,586,182; and U.S. Pat. Publ. Nos. 20080220990A1 and 20090312196A1; each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, Methods Mol. Biol. 57:369-74; Smith, 1985, Ann. Rev. Genet. 19:423-462; Botstein et al., 1985, Science 229:1193-1201; Carter, 1986, Biochem. J. 237:1-7; Kramer et al., 1984, Cell 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; and Stemmer, 1994, Nature 370:389-391. All publications are incorporated herein by reference.

In some embodiments, the clones obtained following mutagenesis treatment are screened for engineered ketoreductases having a desired enzyme property. Measuring ketoreductase enzyme activity from the expression libraries can be performed using standard techniques, such as separation of the product (e.g., by HPLC or GC) and detection of the product by measuring UV absorbance of the separated substrate and products and/or by detection using tandem mass spectroscopy (e.g., MS/MS). Clones containing a polynucleotide encoding the desired engineered polypeptides are then isolated, sequenced to identify the nucleotide sequence changes (if any), and used to express the enzyme in a host cell. Exemplary assays are provided below in the Examples.

Where the sequence of the polypeptide is known, the polynucleotides encoding the enzyme can be prepared by standard solid-phase methods, according to known synthetic methods, e.g., the classical phosphoramidite method described by Beaucage et al., 1981, Tet Lett 22:1859-69, or the method described by Matthes et al., 1984, EMBO J. 3:801-05. In some embodiments, fragments of up to about 100 bases can be individually synthesized, then joined (e.g., by enzymatic or chemical litigation methods, or polymerase mediated methods) to form any desired continuous sequence.

In some embodiments, the present disclosure also provides methods for preparing or manufacturing the non-naturally occurring polypeptides capable of converting compound (2) to compound (1), wherein the methods comprise culturing a host cell capable of expressing a polynucleotide encoding the non-naturally occurring polypeptide under culture conditions suitable for expression of the polypeptide. In some embodiments, the polypeptides can be expressed in cell free expression systems, for example those described in Kudlicki et al., Cell Free Expression, 1st Ed., Landes Biosciences (2007) and Cell Free Protein Synthesis: Methods and Protocols, 1st Ed., Spirin et al., eds., Wiley-VCH (2007), all of which are incorporated herein by reference. In some embodiments, the method for preparing or manufacturing the non-naturally occurring ketoreductase polypeptide further comprises the step of isolating the polypeptide. The non-naturally occurring polypeptides can be expressed in appropriate cells, as described above, and isolated (or recovered) from the host cells, the culture medium, and/or expression medium using any one or more of the well known techniques used for protein purification, including, among others, lysozyme treatment, sonication, filtration, salting-out, ultra-centrifugation, and chromatography. Chromatographic techniques for isolation of the ketoreductase polypeptide include, among others, reverse phase chromatography high performance liquid chromatography, ion exchange chromatography, gel electrophoresis, and affinity chromatography.

In some embodiments, the non-naturally occurring polypeptides of the disclosure can be prepared and used in various forms including but not limited to crude extracts (e.g., cell-free lysates), powders (e.g., shake-flask powders), lyophilizates, and substantially pure preparations (e.g., DSP powders), as further illustrated in the Examples below.

In some embodiments, the non-naturally occurring polypeptide can be prepared and used in purified form, for example a substantially purified form. Generally, conditions for purifying a particular enzyme will depend, in part, on factors such as net charge, hydrophobicity, hydrophilicity, molecular weight, molecular shape, etc., and will be apparent to those having skill in the art. To facilitate purification, it is contemplated that in some embodiments the engineered ketoreductase polypeptides can be expressed as fusion proteins with purification tags, such as His-tags having affinity for metals, or antibody tags for binding to antibodies, e.g., myc epitope tag.

5.5. Methods of Using the Ketoreductases and Product Compounds

In another aspect, the engineered ketoreductase polypeptides disclosed herein can be used in a process for the conversion of the substrate compound (2), or structural analogs thereof, to the product of compound (1) or the corresponding structural analogs. Generally, structural analogs of compound (1) are encompassed within structural formula (I),

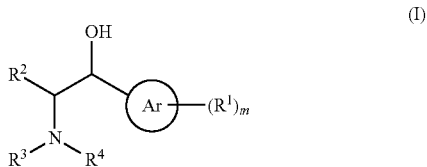

wherein

Ar is a 5 to 7-membered carbocyclic or heterocyclic ring;

each occurrence of $R^1$ is independently selected from halo, —COO$R^a$, —C(O)$R^b$, —O$R^b$, —SO$_2$, —S$R^c$, —S(O)$R^d$, —N$R^e R^f$, —C(O)N$R^g R^h$, —NO$_2$, —CN, alkyl, heteroalkyl, cycloalkyl, cycloalkylalkyl, heterocycloalkyl, heterocycloalkylalkyl, aryl, arylalkyl, heteroaryl and heteroarylalkyl, wherein $R^a$, $R^b$, $R^c$, $R^d$, $R^e$, $R^f$, $R^g$, and $R^h$ are each independently selected from H and an optionally substituted alkyl, heteroalkyl, cycloalkyl, cycloalkylalkyl, heterocycloalkyl, heterocycloalkylalkyl, aryl, arylalkyl, heteroaryl, and heteroarylalkyl;

$R^2$ is selected from an optionally substituted alkyl, alkenyl, alkynyl, heteroalkyl, cycloalkyl, cycloalkylalkyl, cycloalkylalkenyl, cycloalkylalkynyl, heterocycloalkyl, heterocycloalkylalkyl, heterocycloalkylalkenyl, heterocycloalkylalkynyl, aryl, arylalkyl, arylalkenyl, arylalkynyl, heteroaryl, heteroarylalkyl, heteroarylalkenyl, heteroarylalkynyl, alkylthio, alkylsulfinyl, and arylsulfinyl;

$R^3$ and $R^4$ are, independently of the other, selected from H, an optionally substituted alkyl, cycloalkyl, cycloalkylalkyl, heterocycloalkyl, heterocycloalkylalkyl, aryl, arylalkyl, heteroaryl, heteroarylalkyl, alkyloxycarbonyl, arylalkyloxycarbonyl, heteroarylalkyloxycarbonyl, and a protecting group, or one of $R^3$ and $R^4$ forms an optionally substituted 5 to 7-membered heterocyclic ring with $R^2$, and m is 0 to 10.

In some embodiments, the process for the conversion of the substrate of compound (2), or structural analogs thereof, to the product of compound (1) or the corresponding structural analog, can be carried out wherein the substrate of compound (2) is a deuterated version of the compound (2) (i.e., a molecule having the same structure as compound (2) but with one or more the hydrogen atoms of compound (2) substituted with a deuterium atom). Some examples of deuterated versions of pharmaceutical compounds are described in e.g., U.S. Pat. Nos. 5,846,514, 6,503,921, 6,613,739, and 7,705,036. Similarly, the processes for the conversion of a structural analog described herein, including the conversion of the various compounds of formula (II) to the corresponding compounds of formula (I) described below can be carried out using deuterated versions of these compounds.

Accordingly, in some embodiments, a process for the preparation of a compound of formula (I) comprises contacting a compound of formula (II),

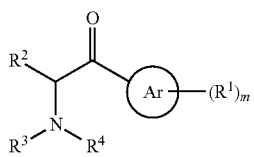

(II)

wherein

R¹, R², R³, R⁴, and m are as defined above, with an engineered ketoreductase polypeptide disclosed herein in presence of cofactor NADPH or NADH under suitable reaction conditions.

In some embodiments of the process, Ar is a 5 to 7-membered aryl or heteroaryl group. In some embodiments, Ar is selected from thienyl, phenyl, and pyridyl.

In some embodiments, m is 1, 2, 3, or 4. In some embodiments, R¹ is halo, in particular bromine or fluorine. In some embodiments, the halo group is fluorine.

In some embodiments of the process, the product compound of formula (I) comprises the compound of formula (Ia),

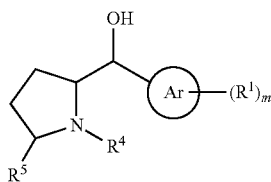

(Ia)

wherein

Ar, R¹, R⁴ and m are as defined above;

R⁵ is an optionally substituted alkyl, alkenyl, alkynyl, heteroalkyl, cycloalkyl, cycloalkylalkyl, cycloalkylalkenyl, cycloalkylalkynyl, heterocycloalkyl, heterocycloalkylalkyl, aryl, arylalkyl, heteroaryl, and heteroarylalkyl.

Accordingly, in some embodiments, a process for preparing the compound of formula (Ia) comprises contacting the substrate compound of formula (IIa),

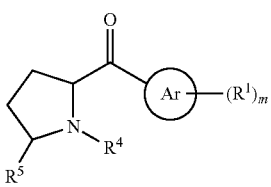

(IIa)

wherein Ar, R¹, R⁴, R⁵ and m are as defined above, with an engineered ketoreductase polypeptide described herein in presence of cofactor NADPH or NADH under suitable reaction conditions.

In some embodiments of the process, the product compound of formula (II) comprises the compound of formula (Ib),

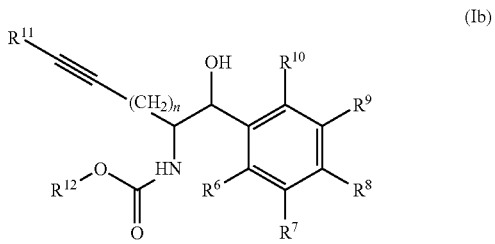

(Ib)

wherein $R^6$, $R^7$, $R^8$, $R^9$, and $R^{10}$ are each independently selected from H, halo, —COOR$^a$, —C(O)R$^b$, —OR$^c$, —SO$_2$, —SR$^d$, —S(O)R$^e$, —NR$^f$R$^g$, —C(O)NR$^h$R$^i$, —NO$_2$, —CN, alkyl, heteroalkyl, cycloalkyl, cycloalkylalkyl, heterocycloalkyl, heterocycloalkylalkyl, aryl, arylalkyl, heteroaryl and heteroarylalkyl, wherein R$^a$, R$^b$, R$^c$, R$^d$, R$^e$, R$^f$, R$^g$, R$^h$ and R$^i$ are independently selected from H and an optionally substituted alkyl, heteroalkyl, cycloalkyl, cycloalkylalkyl, heterocycloalkyl, heterocycloalkylalkyl, aryl, arylalkyl, heteroaryl, and heteroarylalkyl;

n is 1 to 4, $R^{11}$ is selected from H and an optionally substituted alkyl, heteroalkyl, cycloalkyl, cycloalkylalkyl, aryl, arylalkyl, heteroaryl, and heteroarylalkyl; and $R^{12}$ is selected from H, an optionally substituted alkyl, cycloalkyl, cycloalkylalkyl, heterocycloalkyl, heterocycloalkylalkyl, aryl, arylalkyl, heteroaryl, heteroarylalkyl, and a protecting group.

Accordingly, in some embodiments, a process for preparing the product compound of formula (Ib) comprises contacting the substrate compound of formula (IIb)

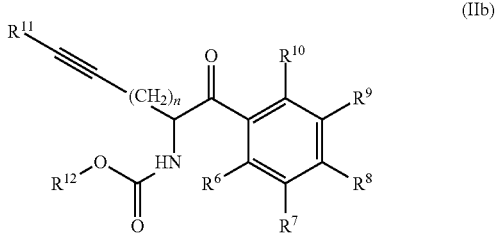

(IIb)

wherein $R^6$, $R^7$, $R^8$, $R^9$, $R^{10}$, $R^{11}$, $R^{12}$ and n are as defined above, with an engineered ketoreductase polypeptide described herein in presence of cofactor NADPH or NADH under suitable reaction conditions.

In some embodiments, $R^{11}$ of the compound of formula (IIb) comprises an optionally substituted phenyl.

In some embodiments, n of the compound of formula (IIb) comprises 2, 3 or 4.

In some embodiments of the process, the product compound of formula (Ib) comprises compounds of formula (Ib1) and (Ib3), and the process forms product compounds of formula (Ib1) and (Ib3) in diastereomeric excess of compounds of formula (Ib2) and (Ib4),

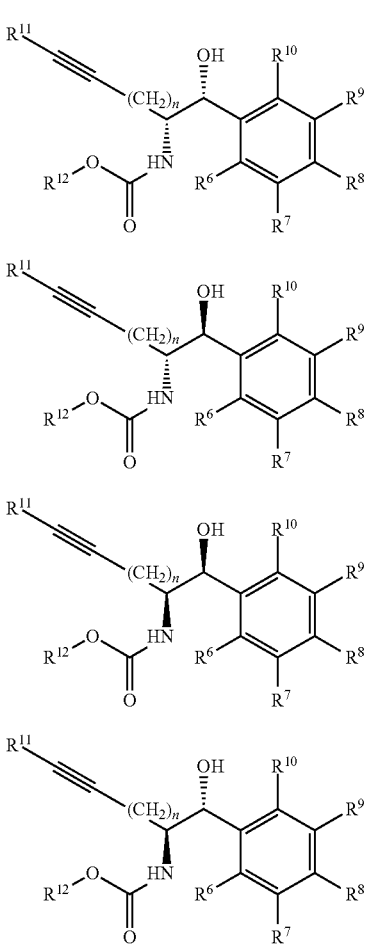

wherein
$R^6$, $R^7$, $R^8$, $R^9$, $R^{10}$, $R^{11}$, $R^{12}$ and n are as in defined for formula (Ib).

Accordingly, in some embodiments, a process for preparing the compounds of formula (Ib1) and (Ib3) in diastereomeric excess of compounds of formula (Ib2) and (Ib4) comprises contacting the substrate compound of formula (IIb)

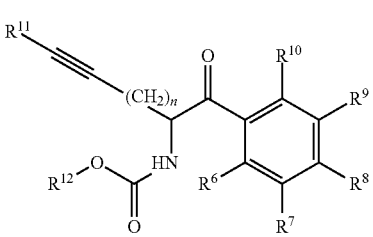

wherein
$R^6$, $R^7$, $R^8$, $R^9$, $R^{10}$, $R^{11}$, $R^{12}$ and n are as in defined for formula (Ib);
with an engineered ketoreductase with diastereoselectivity for compounds of formula (Ib1) and (Ib3) over compounds of formula (Ib2) and (Ib4) in presence of cofactor NADPH or NADH under suitable reaction conditions.

In some embodiments of the process, the compound of formula (IIb) comprises a mixture of compounds of formula (IIb1) and (IIb2)

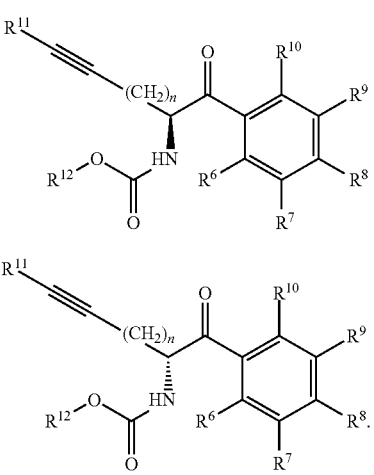

In some embodiments of the process, the compound of formula (IIb) comprises a racemic mixture of compounds of formula (IIb1) and (IIb2).

In some embodiments of the process using compound of formula (IIb), n is selected from 2, 3 or 4. In some embodiments, n is 2. In some embodiments, n is 2 and $R^6$, $R^7$, $R^8$, $R^9$, $R^{10}$ and $R^{11}$ are H.

In some embodiments of the process, the product compound of formula (Ib) comprises compound of formula (Ic)

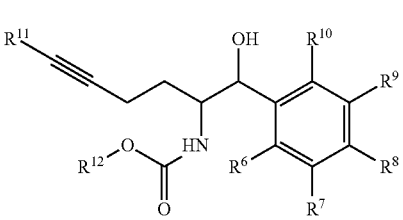

wherein
$R^6$, $R^7$, $R^8$, $R^9$, $R^{10}$, $R^{11}$ and $R^{12}$ are as defined for the compound of formula (Ib).

Accordingly, in some embodiments, a process for preparing the product compound of formula (Ic) comprises contacting the substrate compound of formula (IIc)

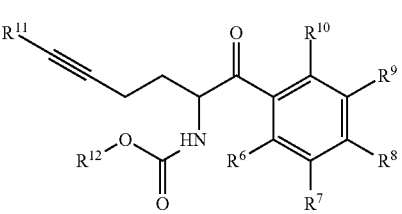

wherein
$R^6$, $R^7$, $R^8$, $R^9$, $R^{10}$, $R^{11}$ and $R^{12}$ are as defined for the compound of formula (Ib)

with an engineered ketoreductase polypeptide described herein in presence of cofactor NADPH or NADH under suitable reaction conditions.

In some embodiments of the process, the product compound of formula (Ib) comprises compounds of formula (Ic1) and (Ic3), and the process forms product compounds of formula (Ic1) and (Ic3) in diastereomeric excess of compounds of formula (Ic2) and (Ic4),

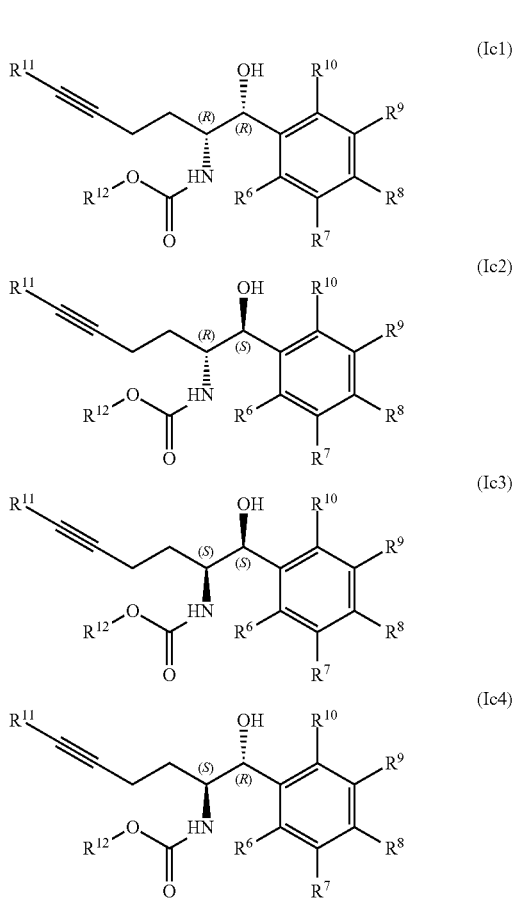

wherein
$R^6$, $R^7$, $R^8$, $R^9$, $R^{10}$, $R^{11}$ and $R^{12}$ are as defined for the compound of formula (Ib).

Accordingly, in some embodiments, a process for preparing the product compounds of formula (Ic1) and (Ic3) in diastereomeric excess of the compounds of formula (Ic2) and (Ic4) comprises contacting the substrate compound of formula (IIc)

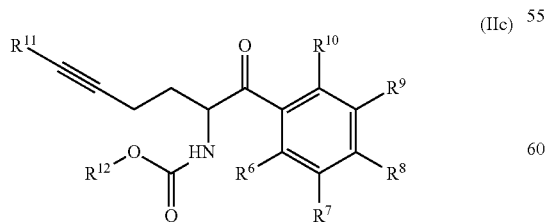

wherein
$R^6$, $R^7$, $R^8$, $R^9$, $R^{10}$, $R^{11}$ and $R^{12}$ are as defined for the compound of formula (Ib);

with an engineered ketoreductase polypeptide having diastereoselectivity for the product compounds of formula (Ic1) and (Ic3) over the compounds of formula (Ic2) and (Ic4) in presence of cofactor NADPH or NADH under suitable reaction conditions.

In some embodiments of the process, the compound of formula (IIc) comprises a mixture of compounds of formula (IIc1) and (IIc2),

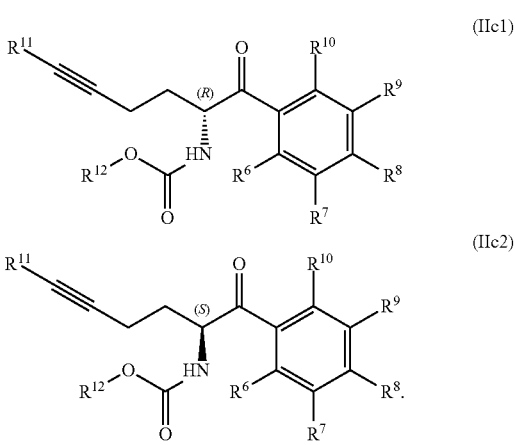

In some embodiments of the process, the compound of formula (IIb) comprises a racemic mixture of the compounds of formula (IIb1) and (IIb2).

In some embodiments of the process, the product compound of formula (Ib) comprises compound of formula (Id),

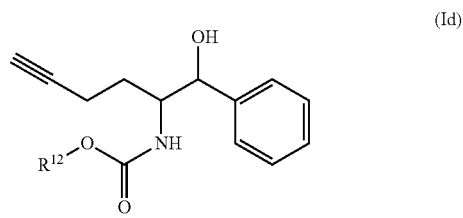

wherein
$R^{12}$ is as defined for the compound of formula (Ib).

Accordingly, in some embodiments, a process for preparing the product compound of formula (Id) comprises contacting the substrate compound of formula (IId),

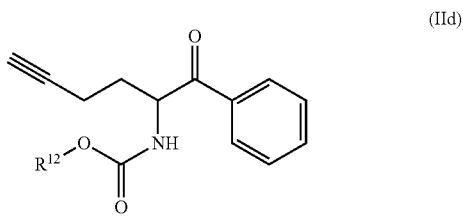

wherein
$R^{12}$ is as defined for the compound of formula (Ib);
with an engineered ketoreductase polypeptide described herein in presence of cofactor NADPH or NADH under suitable reaction conditions.

In some embodiments of the process, the product compound of formula (Ib) comprises compounds of formula (Id1) and (Id3), and the process forms product compounds of formula (Id1) and (Id3) in diastereomeric excess of compounds of formula (Id2) and (Id4),

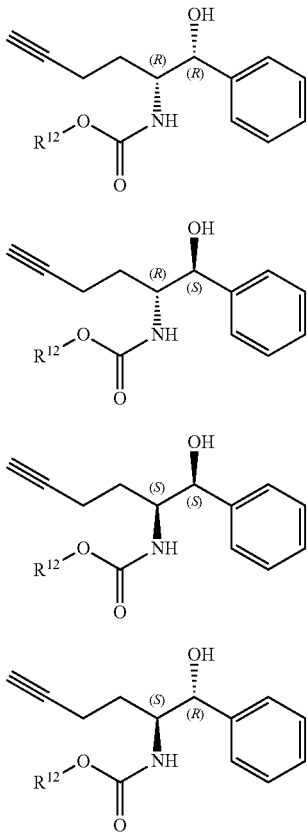

wherein $R^{12}$ is as defined for the compound of formula (Ib).

Accordingly, in some embodiments, a process for preparing the product compounds of formula (Id1) and (Id3) in diastereomeric excess of compounds of formula (Id2) and (Id4) comprises contacting the substrate compound of formula (IId)

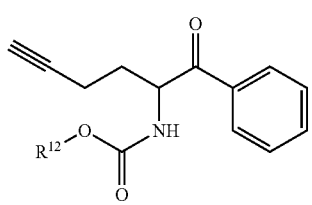

wherein $R^{12}$ is as defined for the compound of formula (Ib);

with an engineered ketoreductase polypeptide having diastereoselectivity for the product compounds of formula (Id1) and (Id3) over the compounds of formula (Id2) (Id4) in presence of cofactor NADPH or NADH under suitable reaction conditions.

In some embodiments of the process, the compound of formula (IId) comprises a mixture of compounds of formula (IId1) and (IId2).

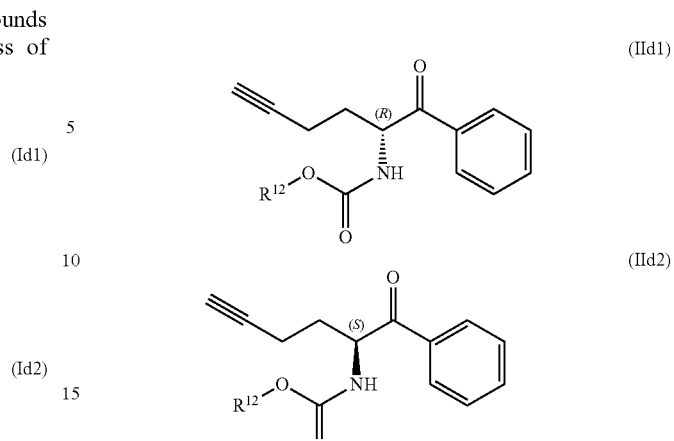

In some embodiments of the process, the compound of formula (IId) comprises a racemic mixture of compounds of formula (IId1) and (IId2).

In some embodiments of the processes for preparing compounds of formula (Ib1) and (Ib3) in diastereomeric excess of the compounds (Ib2) and (Ib4), the compounds of formula (Ic1) and (Ic3) in diastereomeric excess of the compounds (Ic2) and (Ic4) or the compounds of formula (Id1) and (Id3) in diastereomeric excess of the compounds (Id2) and (Id4), the group $R^{12}$ is selected from methyl, ethyl, n-propyl, isopropyl,-butyl, iso-butyl, sec-butyl, and tert-butyl. In some embodiments, $R^{12}$ is tert-butyl.

In some embodiments, exemplary engineered ketoreductases with diastereoselectivity for product compounds of formula (Ib1) and (Ib3) over the product compounds of formula (Ib2) and (Ib4) include a ketoreductase polypeptide comprising an amino acid sequence selected from SEQ ID NO: 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments of the processes above, the product compounds of formula (Id1) and (Id3) are formed in diastereomeric ratio of at least 50 over compounds of formula (Id2) and (Id4). In some embodiments, exemplary engineered ketoreductases capable of forming product compounds of formula (Id1) and (Id3) in diastereomeric ratio of at least 50 over compounds of formula (Id2) and (Id4) include a polypeptide comprising an amino acid sequence selected from SEQ ID NO: 18, 20, 22, 24, 26, 28, 32, 34, 36, 38, 40, 42 and 44.

In some embodiments the process, the product compound of formula (Ib) comprises compound of formula (Ib1), and the product compound of formula (Ib1) is formed in diastereomeric excess of compound of formula (Ib3)

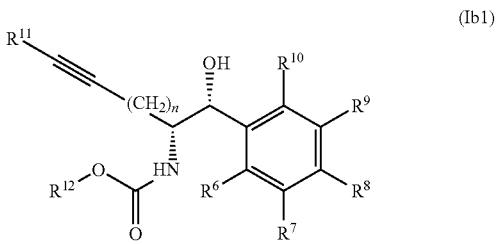

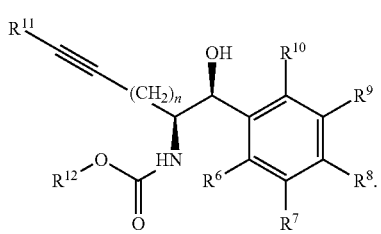

(Ib3)

wherein, $R^6$, $R^7$, $R^8$, $R^9$, $R^{10}$, $R^{11}$, $R^{12}$ and n are as provided above. In some embodiments, n is selected from 2, 3 or 4. In some embodiments, n is 2. In some embodiments, n is 2 and $R^6$, $R^7$, $R^8$, $R^9$, $R^{10}$ and $R^{11}$ are H.

Accordingly, in some embodiments, a process for preparing the compound of formula (Ib1) in diastereomeric excess of the compound of formula (Ib3) comprises contacting the substrate compound of formula (IIb)

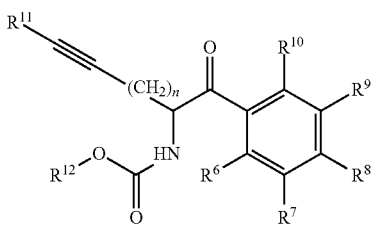

(IIb)

with an engineered ketoreductase diastereoselective for the product compound of formula (Ib1) over the compound of formula and (Ib3) in presence of cofactor NADPH or NADH under suitable reaction conditions.

In some embodiments of the process for preparing the compound of formula (Ib1) in diastereomeric excess of the compound of formula (Ib3), the substrate compound (IIb) comprises a mixture of compounds of formula (IIb1) and (IIb2).

In some embodiments of the above process, the substrate compound (IIb) comprises a racemic mixture of compounds of formula (IIb1) and (IIb2).

In some embodiments of the process, the product compound of formula (Ib1) comprises compound of formula (Ic1), and the compound formula (Ic1) is formed in diastereomeric excess of compound of formula (Ic3)

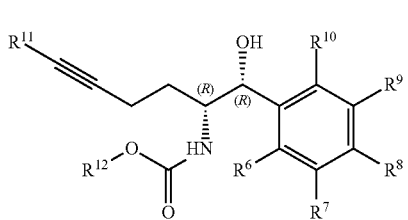

(Ic1)

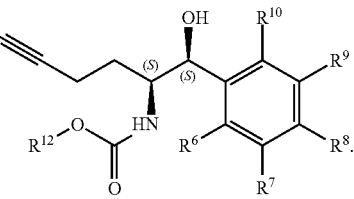

(Ic3)

Accordingly, in some embodiments, the process for preparing compound of formula (Ic1) in diastereomeric excess of compound of formula (Ic3) comprises contacting the substrate compound of formula (IIc)

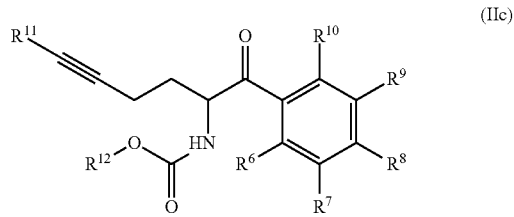

(IIc)

wherein $R^6$, $R^7$, $R^8$, $R^9$, $R^{10}$, $R^{11}$, and $R^{12}$ are as defined for the compound of formula (Ib);

with an engineered ketoreductase with an engineered ketoreductase diastereoselective for having diastereoselectivity for the product compound of formula (Ic1) over the compound of formula (Ic3) in presence of cofactor NADPH or NADH under suitable reactions.

In some embodiments of the process for preparing compound formula (Ic1) in diastereomeric excess of compound of formula (Ic3), the substrate compound (IIc) comprises a mixture of compounds of formula (IIc1) and (IIc2).

In some embodiments of the above process, the substrate compound (IIc) comprises a racemic mixture of compounds of formula (IIc1) and (IIc2).

In some embodiments of the process, the product compound of formula (Ib) comprises the compound of formula (Id1), and the compound of formula (Id1) is formed in diastereomeric excess of compound of formula (Id3)

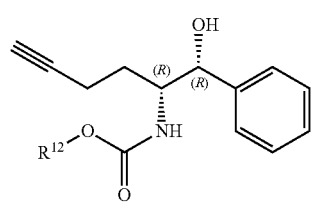

(Id1)

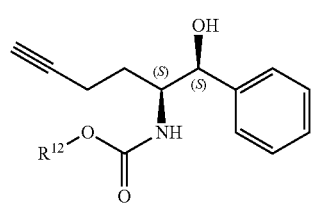

(Id3)

wherein
$R^{12}$ is as defined for the compound of formula (Ib).

Accordingly, in some embodiments, a process for preparing the compound of formula (Id1) in diastereomeric excess of compound of formula (Id3) comprises contacting the substrate compound of formula (IId)

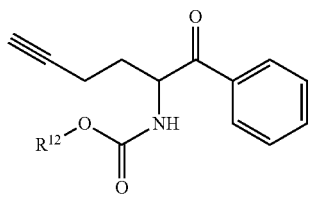
(IId)

wherein

R$^{12}$ is as defined for the compound of formula (Ib);

with an engineered ketoreductase having diastereoselectivity for the product compound of formula (Id1) over the compound of formula (Id3) in presence of NADPH or NADH under suitable reaction conditions.

In some embodiments of the process for preparing the compound of formula (Id1) in diastereomeric excess of compound of formula (Id3), the compound of formula (IId) comprises a mixture of substrate compounds of formula (IId1) and (IId2).

In some embodiments of the process, the compound of formula (IId) comprises a racemic mixture of substrate compounds of formula (IId1) and (IId2).

In some embodiments of the above processes for preparing the compound of formula (Ib1) in diastereomeric excess of the compound of formula (Ib3), the compound of formula (Ic1) in diastereomeric excess of the compound of formula (Ic3), or the compound of formula (Id1) in diastereomeric excess of the compound of formula (Id3), the group R$^{12}$ is selected from methyl, ethyl, n-propyl, isopropyl,-butyl, iso-butyl, sec-butyl, and tert-butyl. In some embodiments, R$^{12}$ is tert-butyl.

In some embodiments, exemplary engineered ketoreductases with diastereoselectivity for product compounds of formula (Ib1) and (Ib3) over the compounds of formula (Ib2) and (Ib4), product compounds of formula (Ic1) and (Ic3) over the compounds of formula (Ic2) and (Ic4), or product compounds of formula (Id1) and (Id3) over the compounds of formula (Id2) and (Id4), include a polypeptide comprising an amino acid sequence selected from 18, 20, 22, 24, 26, 28, 30, 32, 34, 36, 38, 40, 42, 44, 56, 58, 60, 62, 64, 66, 68, 70, 72, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170 and 172.

In some embodiments, the product compounds of the ketoreductase reaction can be modified to provide other useful intermediates in the synthesis of drug compounds. Accordingly, in some embodiments, the hydroxyl group of the product compounds can be processed to have a protecting group. Such protected product compounds, include the compounds of formula (I'), (Ia'), (Ib'), (Ic'), and (Id') below:

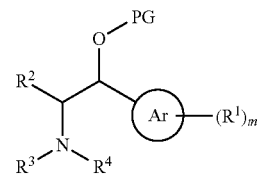
(I')

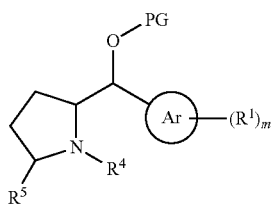
(Ia')

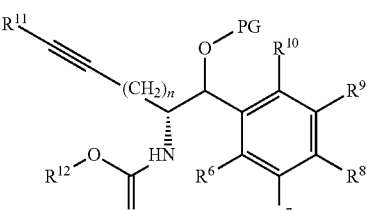
(Ib')

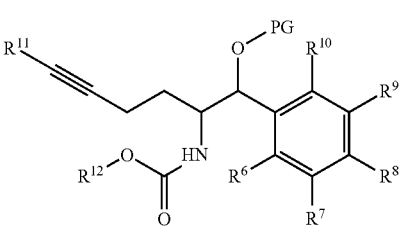
(Ic')

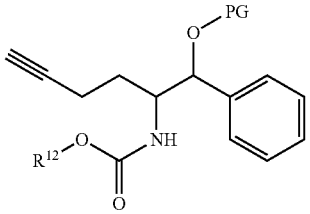
(Id')

wherein,

Ar, R$^1$, R$^2$, R$^3$, R$^4$, R$^5$, R$^6$, R$^7$, R$^8$, R$^9$, R$^{10}$, R$^{11}$, and R$^{12}$ are as defined previously; and PG is a protecting group.

Accordingly, in some embodiments, a process for preparing compound (I'), (Ia'), (Ib'), (Ic'), or (Id') can comprise a step of modifying the product compound (I), (Ia), (Ib), (Ic), or (Id), respectively, with a protecting group.

In the above embodiments where a substituent comprises a protecting group, the protecting group can be any suitable protecting group for the relevant functional group. For example, an amine protecting group can be selected from, among others, tert-butyloxycarbonyl (Boc), 9-fluorenylmethyloxycarbonyl (Fmoc), trichloroethyl chloroformate (Troc), p-methoxybenzyl carbonyl (Moz), 3,4-dimethoxybenzyl (DMPM), p-methoxybenzyl (Pmb), tosyl (Ts) and carbobenzyloxy (Cbz). A carboxyl protecting group can be selected from, among others, alkyl esters (e.g., tert-butyl ester), arylalkyl esters (e.g., benzyl ester), silyl ester, and oxazoline. A hydroxyl protecting group can be selected from, among others, alkyloxy (e.g., methyl ether), alkyloxyalkyl (e.g., methoxymethyl ether: MOM), methoxyethoxymethyl ethers (MEM), methyl thiomethyl ethers (MTM), benzyloxymethyl ethers (BOM), tetrahydropyranyl ether (THP), p-methoxybenzyl ethers (PMB), trityl ethers, methoxytrityl ethers, and silyl ethers (e.g., trimethylsilyl ethers: TMS). Other suitable protecting groups are described in Wuts and Greene, "Greene's Protective Groups in Organic Synthesis," 4$^{th}$ Ed., Wiley Interscience (2006), incorporated herein by reference.

In the embodiments herein and illustrated in the Examples, the present disclosure contemplates ranges of suitable reaction conditions that can be used in the processes, including but not limited to ranges of pH, temperature, buffer, solvent system, substrate loading, mixture of substrate compound stereoisomers, polypeptide loading, cofactor loading, pressure, and reaction time. Further suitable reaction conditions for carrying out the process for biocatalytic conversion of substrate compounds to product compounds using an engineered ketoreductase polypeptide described herein can be readily optimized by routine experimentation that includes, but is not limited to, contacting the engineered ketoreductase polypeptide and substrate compound under experimental reaction conditions of concentration, pH, temperature, solvent conditions, and detecting the product compound, for example, using the methods described in the Examples provided herein.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments of the processes, the suitable reaction conditions comprise a substrate compound loading concentration of at least about 1 to about 200 g/L, about 10 g/L to about 200 g/L, about 20 g/L to about 200 g/L, about 40 g/L to about 200 g/L, about 50 g/L to about 200 g/L, about 75 g/L to about 200 g/L, about 100 g/L to about 200 g/L, about 125 g/L to about 200 g/L, about 150 g/L to about 200 g/L or about 75 g/L to about 150 g/L. In some embodiments, the suitable reaction conditions comprise a substrate compound loading concentration of at least about 1 g/L, about 10 g/L, about 20 g/L, about 40 g/L, about 50 g/L, about 75 g/L, about 100 g/L, about 125 g/L, about 150 g/L, about 175 g/L, or about 200 g/L, or even greater. The values for substrate loadings provided herein are based on the molecular weight of compound (2); however it also contemplated that the equivalent molar amounts of various hydrates and salts of compound (2) also can be used in the process. In addition, substrates compounds covered by compound of formulas (II), (IIa), (IIb), (IIc), and (IId) can also be used in appropriate amounts, in light of the amounts used for compound (2) and the relevant solvent conditions.

The improved activity and/or stereoselectivity of the engineered ketoreductase polypeptides disclosed herein provides for processes wherein higher percentage conversion can be achieved with lower concentrations of the engineered polypeptide. It also reduces the amount of residual protein that may need to be removed in subsequent steps for purification of product compound (e.g., compound (1)). In some embodiments of the process, the suitable reaction conditions comprise an engineered ketoreductase polypeptide concentration of about 0.1 to about 20 g/L, about 0.1 to about 10 g/L, about 0.5 to about 10 g/L, about 1.0 to about 10 g/L, about 0.1 to about 5 g/L, about 0.1 g/L to about 2 g/L, or about 0.1 g/L to about 1.0 g/L. In some embodiments, the suitable reaction conditions comprise an engineered ketoreductase polypeptide concentration of about 20 g/L or less, about 15 g/L or less, about 10 g/L or less, about 5 g/L or less, about 4 g/L or less, about 2 g/L or less, about 1 g/L or less, about 0.5 g/L or less, about 0.2 g/L or less, or about 0.1 g/L.

During the course of the ketoreductase reactions, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, carbonate, phosphate, triethanolamine buffer, and the like. In some embodiments, the buffer is borate. In some embodiments, the suitable reaction conditions comprise a buffer solution of borate, where the borate concentration is from about 0.01 to about 0.4 M, about 0.05 to about 0.4 M, about 0.1 to about 0.3 M, or about 0.1 to about 0.2 M. In some embodiments, the reaction condition comprises a borate concentration of about 0.01, about 0.02, about 0.03, about 0.04, about 0.05, about 0.07, about 0.1, about 0.12, about 0.14, about 0.16, about 0.18, about 0.2, about 0.3, or about 0.4 M. In some embodiments, the reaction conditions comprise water as a suitable solvent with no buffer present.

In the embodiments of the process, the reaction conditions can comprise a suitable pH. As noted above, the desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH of about a pH of about 6 to about 12, a pH or about 6 to about 11, a pH of about 7 to about 11, a pH of about 7 to about 10, a pH of about 8 to about 10, a pH of about 9 to about 10, a pH of about 8 to about 9.5, or a pH of about 8 to about 9. In some embodiments, the reaction conditions comprise a solution pH of about 6, a pH of about 6.5, a pH of about 7, a pH of about 7.5, a pH of about 8, a pH of about 8.5, a pH of about 9, a pH of about 9.5, a pH of about 10, a pH of about 10.5, a pH of about 11, a pH of about 11.5, or a pH of about 12. A person of ordinary skill in the art can use an appropriate pH or a range of pH by considering, by way of example and not limitation, stability and activity of the ketoreductase, stability of substrate and product, and stability of the cofactor.

In the embodiments of the processes herein, a suitable temperature can be used for the reaction conditions, for example, taking into consideration the increase in reaction rate at higher temperatures, the activity of the enzyme during the reaction, and as further described below, increase rate of equilibration (e.g., racemization) of the substrate diastereomers for dynamic kinetic resolution reactions. For example, the engineered polypeptides of the present disclosure have increased stability relative to naturally occurring ketoreductase polypeptide e.g., the wild type polypeptide of SEQ ID NO: 2, and in some embodiments, the engineered ketoreductase of SEQ ID NO:32, which allow the engineered polypeptides to be used at higher temperatures for increased conversion rates and improved substrate solubility in the reaction solution. Accordingly, in some embodiments, the suitable reaction conditions comprise a temperature of about 20° C. to about 60° C., about 25° C. to about 60° C., about 30° C. to about 60° C., about 35° C. to about 60° C., about 40° C. to about 60° C., about 45° C. to about 60° C., about 45° C. to about 55° C., or about 50° C. to about 55° C. In some embodiments, the suitable reaction conditions can comprise an ambient temperature (e.g., 25° C.) or a temperature of about 27° C., about 30° C., about 32° C., about 35° C., about 37° C., about 40° C., about 45° C., about 50° C., about 55° C. or about 60° C. In some embodiments, the temperature during the enzymatic reaction can be maintained at a temperature throughout the course of the reaction. In some embodiments, the temperature during the enzymatic reaction can be adjusted over a temperature profile during the course of the reaction.

Generally, the processes are carried out in a solvent. Suitable solvents include water, aqueous buffer solutions, organic solvents, and/or co-solvent systems, which generally comprise aqueous solvents and organic solvents. Suitable solvents include water, aqueous buffer solutions, organic solvents, and/or co-solvent systems, which generally comprise aqueous solvents and organic solvents. The aqueous solvent (water or aqueous co-solvent system) may be pH-buffered or unbuffered. In some embodiments, the processes using the engineered ketoreductase polypeptides are generally carried out in an aqueous co-solvent system comprising an organic solvent (e.g., ethanol, isopropyl alcohol (IPA), dimethyl sulfoxide (DMSO), ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). The organic solvent component of an aqueous co-solvent system may be miscible with the aqueous component, providing a single liquid phase, or may be partly miscible or immiscible with the aqueous component, providing two liquid phases. Exemplary aqueous co-solvent systems comprises water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

In some embodiments of the process, the suitable reaction conditions comprise an aqueous co-solvent comprising DMSO at a concentration of about 1% to about 50% (v/v), about 1 to about 40% (v/v), about 2% to about 40% (v/v), about 5% to about 30% (v/v), about 10% to about 30% (v/v), or about 10% to about 20% (v/v). In some embodiments of the process, the suitable reaction conditions comprise an aqueous co-solvent comprising DMSO at a concentration of at least about 1%, about 5%, about 10%, about 15%, about 20%, about 25%, about 30%, about 35%, about 40%, about 45%, or about 50% (v/v).

In some embodiments, the processes can be carried out under reaction conditions comprising an aqueous buffer solution, an organic solvent, or a co-solvent system. In some embodiments, the buffer solution is borate, for example, of about 0.025 M to about 0.25 M borate. In some embodiments, the co-solvent system comprises about 95% to about 5% (v/v) of an aqueous buffer solution (e.g., about 0.2 M borate), and about 5% (v/v) to about 95% (v/v) of an organic solvent solution, for example, isopropyl alcohol. In some embodiments, the co-solvent system comprises about 30% (v/v) to about 70% (v/v) of an aqueous buffer solution (e.g., about 0.2 M borate) and about 70% (v/v) to about 30% (v/v) of an organic solvent solution (e.g., IPA). In some embodiments, the reaction conditions comprise water as a suitable solvent with no buffer present.

In some embodiments, the co-solvent system comprises an aqueous buffer solution and IPA, wherein the IPA concentration is about 5% to about 95% (v/v), about 10% to about 90% (v/v), about 15% to about 90% (v/v), about 20% to about 90% (v/v), about 25% to about 80% (v/v), about 25% to about 75% (v/v), about 35% to about 75% (v/v), about 45% to about 75% (v/v), about 55% to about 75% (v/v), about 60% to about 70% (v/v), or about 60% to about 65% (v/v). In some embodiments, the IPA concentration is at least about 25% (v/v), at least about 35% (v/v), at least about 45% (v/v), at least about 55% (v/v), about 60% (v/v), about 65% (v/v), about 70% (v/v), about 75% (v/v), about 80%, about 85% (v/v), about 90% (v/v) or about 95% (v/v). In some embodiments, the reaction conditions comprise a co-solvent system of 0.2 M borate buffer and about 60% (v/v) to about 70% (v/v) IPA. In some embodiments, the reaction conditions comprise a co-solvent system of about 0.2 M borate buffer and about 90% (v/v) IPA, about 0.2 M borate buffer and about 85% (v/v) IPA, about 0.2 M borate buffer and about 80% (v/v) IPA, about 0.2 M borate buffer and about 75% (v/v) IPA, about 0.2 M borate buffer and about 70% (v/v) IPA, about 0.2 M borate buffer and about 65% (v/v) IPA, about 0.2 M borate buffer and about 65% (v/v) IPA, about 0.2 M borate buffer and about 60% (v/v) IPA, about 0.2 M borate buffer and about 55% (v/v) IPA, or about 0.2 M borate buffer and about 50% (v/v) IPA.

As described above, the process of converting the various substrate compounds to their corresponding product compounds using the engineering ketoreductase polypeptides can take advantage of the equilibration of the stereoisomers of the substrate compounds, for example compounds (IIc1) and (IIc2) and the high stereoselectivity of the engineered ketoreductase polypeptides disclosed herein to carry out a dynamic kinetic resolution (DKR) dynamic, also referred to as kinetic asymmetric transformation (DKAT), whereby the amount of a specific stereoisomer or stereoisomers formed is greater than the amount of corresponding stereomeric substrate or substrates, e.g., compound (IIc1) and compound (IIc2), present at the beginning of the reaction.

Accordingly, in some embodiments, a process for preparing product compound of formula (Ib1) in diastereomeric excess of compound of formula (Ib3),

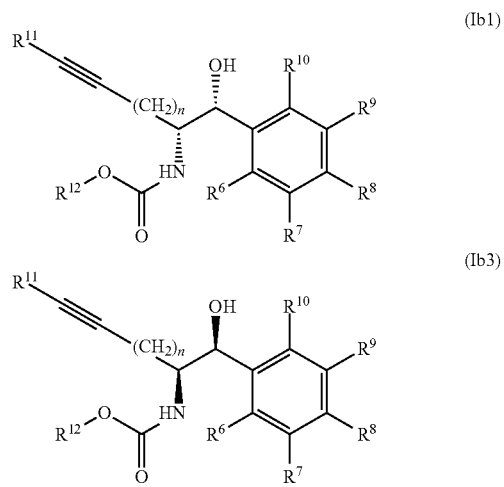

wherein,
$R^6$, $R^7$, $R^8$, $R^9$, $R^{10}$, $R^{11}$, $R^{12}$ and n are as defined above for the compound of formula (Ib);

comprises contacting the substrate compound of formula (IIb)

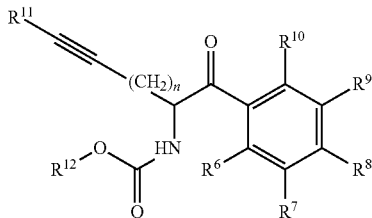
(IIb)

with an engineered ketoreductase diastereoselective for the product compounds of formula (Ib1) and (Ib3) over the compounds of formula (Ib2) and (Id4) in presence of cofactor NADPH or NADH under suitable reaction conditions for equilibration of substrate compounds of formula (IIb1) and (IIb2)

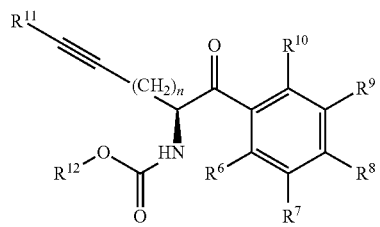
(IIb1)

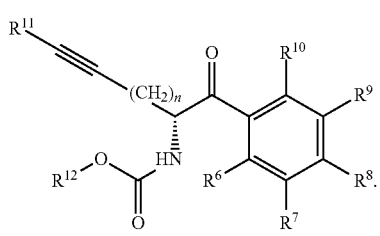
(IIb2)

In some embodiments of the above process, the substrate compound (IIb) comprises a mixture of compounds of formula (IIb1) and (IIb2).

In some embodiments of the above process, the substrate compound (IIb) comprises a racemic mixture of compounds of formula (IIb1) and (IIb2).

In some embodiments of the process, the product compound of formula (Ib1) comprises compound of formula (Ic1), and product compound of formula (Ic1) is formed in diastereomeric excess of compound of formula (Ic3)

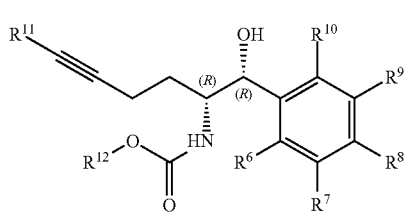
(Ic1)

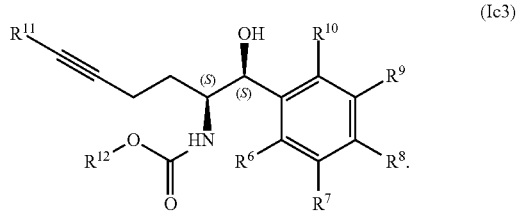
(Ic3)

Accordingly, in some embodiments, the process for preparing compound of formula (Ic1) in diastereomeric excess of compound of formula (Ic3) comprises contacting the substrate compound of formula (IIc)

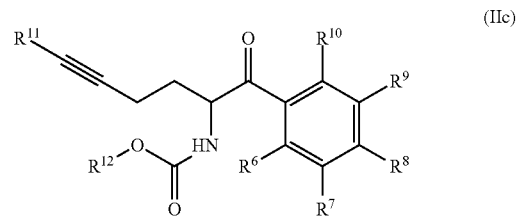
(IIc)

wherein
$R^6$, $R^7$, $R^8$, $R^9$, $R^{10}$, $R^{11}$, and $R^{12}$ are as defined for the compound of formula (Ib);

with an engineered ketoreductase with an engineered ketoreductase diastereoselective for the product compounds of formula (Ic1) and (Ic3) over the compounds of formula (Ic2) and (Ic4) in presence of cofactor NADPH or NADH under suitable reaction conditions for equilibration of substrate compounds of formula (IIc1) and (IIc2)

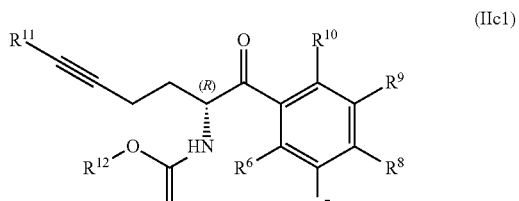
(IIc1)

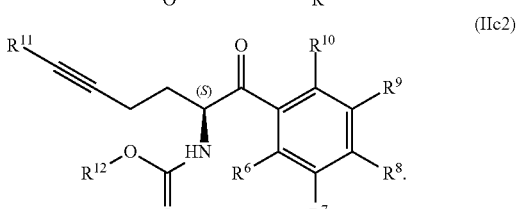
(IIc2)

In some embodiments of the above process, the substrate compound (IIc) comprises a mixture of compounds of formula (IIc1) and (IIc2).

In some embodiments of the above process, the substrate compound (IIc) comprises a racemic mixture of compounds of formula (IIc1) and (IIc2).

In some embodiments of the process, the product compound of formula (Ib) comprises the compound of formula (Id1), and product compound of formula (Id1) is formed in diastereomeric excess of compound of formula (Id3)

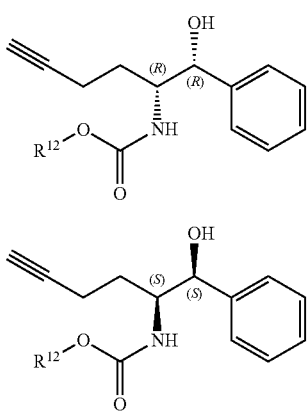

(Id1)

(Id3)

wherein
R$^{12}$ is as defined for the compound of formula (Ib).

Accordingly, in some embodiments, a process for preparing the compound of formula (Id1) in diastereomeric excess of compound of formula (Id3) comprises contacting the substrate compound of formula (IId)

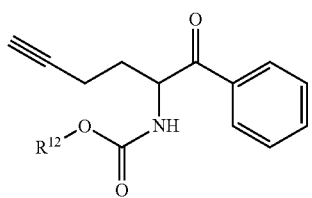

(IId)

with an engineered ketoreductase having diastereoselectivity for the product compounds of formula (Id1) and (Id3) over the compounds of formula (Id2) and (Id4) in presence of NADPH or NADH under suitable reaction conditions for equilibration of substrate compounds of formula (IId1) and (IId2)

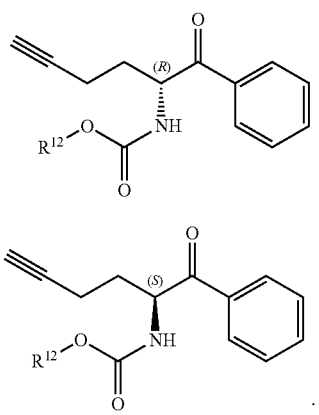

(IId1)

(IId2)

In some embodiments of the process for preparing the compound of formula (Id1) in diastereomeric excess of compound of formula (Id3), the compound of formula (IId) comprises a mixture of substrate compounds of formula (IId1) and (IId2).

In some embodiments of the process for preparing the compound of formula (Id1) in diastereomeric excess of compound of formula (Id3), the compound of formula (IId) comprises a racemic mixture of substrate compounds of formula (IId1) and (IId2).

Because the equilibration of substrate compounds, e.g., (IIb1) and (IIb2); (IIc1) and (IIc2); or (IId1) and (IId2) in the ketoreductase reaction is favored at conditions of pH 9 or higher and at temperatures of 45° C. or higher, in some embodiments, the suitable conditions for a DKR or DKAT can comprise a solution pH of at least pH 9, at least 9.5, at least pH 10.0, at least pH 10.5, at least pH 11.0, at least pH 11.5, and a solution temperature of at least 45° C., at least 50° C., at least 55° C., at least 60° C., or at least 65° C.

In some embodiments of the above processes, the reaction conditions for equilibration of substrate compounds comprise a pH of about 9 to about 12 and a temperature of about 45° C. to about 60° C. In some embodiments of the above processes, the reaction conditions for equilibration of substrate compounds comprise a pH of about 10 to about 12 and a temperature of about 50° C. to about 65° C.

Generally, the ketoreductase mediated reductions use an electron donor. In some embodiments, the electron donor is a cofactor. Suitable cofactors include, but are not limited to, NADP$^+$ (nicotinamide adenine dinucleotide phosphate), NADPH (the reduced form of NADP$^+$), NAD$^+$ (nicotinamide adenine dinucleotide) and NADH (the reduced form of NAD$^+$). Typically, the reduced form of the cofactor is added to the reaction mixture, and thus in some embodiments, the processes are carried out in presence of an electron donor selected from NADPH cofactor or NADH cofactor. In some embodiments, the electron donor is NADPH cofactor. In some embodiments, the process can be carried out wherein the reaction conditions comprise an NADH or NADPH cofactor concentration of about 0.01 to about 1 g/L, about 0.03 to about 0.8 g/L, about 0.05 to about 0.5 g/L, about 0.1 to about 0.3 g/L, about 0.05 to about 0.2 g/L, or about 0.1 to about 0.2 g/L. In some embodiments, the process is carried out under NADH or NADPH cofactor concentration of about 1 g/L, about 0.8 g/L, about 0.5 g/L, about 0.3 g/L, about 0.2 g/L, about 0.1 g/L, about 0.05 g/L, or about 0.01 g/L.

In some embodiments of the process, an optional cofactor recycling system, also referred to as a cofactor regeneration system, can be used to regenerate cofactor NADPH/NADH from NADP+/NAD+ produced in the enzymatic reaction. A cofactor regeneration system refers to a set of reactants that participate in a reaction that reduces the oxidized form of the cofactor (e.g., NADP to NADPH). Cofactors oxidized by the polypeptide reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, which catalyzes the reduction of the oxidized form of the cofactor by the reductant. Cofactor regenerating systems to regenerate NADH or NADPH from NAD$^+$ or NADP$^+$, respectively, are known in the art and can be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropyl alcohol) alcohol and secondary alcohol dehydrogenase, phosphite and phosphite dehydrogenase, molecular hydrogen and hydrogenase, and the like. These systems may be used in combination with either $NADP^+/NADPH$ or $NAD^+/NADH$ as the cofactor. Electrochemical regeneration using hydrogenases may also be used as a cofactor regeneration system, for examples, those described in U.S. Pat. Nos. 5,538,867 and 6,495,023, both of which are incorporated herein by reference. Chemical cofactor regeneration systems comprising a metal catalyst and a reducing agent (for example, molecular hydrogen or formate) may also be suitable. See, e.g., PCT publication WO 2000/053731, which is incorporated herein by reference.

In some embodiments, the cofactor regeneration system comprises glucose dehydrogenase (GDH), which is a $NAD^+$ or $NADP^+$-dependent enzyme that catalyzes the conversion of D-glucose and $NAD^+$ or $NADP^+$ to gluconic acid and NADH or NADPH, respectively. Glucose dehydrogenases suitable for use in the practice of the processes herein include naturally occurring glucose dehydrogenases as well as non-naturally occurring glucose dehydrogenases. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring glucose dehydrogenases generated using, for example, mutagenesis, directed evolution, and the like and are provided in PCT publication WO 2005/018579, and US publication Nos. 2005/0095619 and 2005/0153417. All of these sequences are incorporated herein by reference.

In some embodiments, the cofactor regeneration system comprises a formate dehydrogenase, which is a $NAD^+$ or $NADP^+$-dependent enzyme that catalyzes the conversion of formate and $NAD^+$ or $NADP^+$ to carbon dioxide and NADH or NADPH, respectively. Formate dehydrogenases suitable for use as cofactor regenerating systems in the ketoreductase reactions described herein include naturally occurring and non-naturally occurring formate dehydrogenases. Suitable formate dehydrogenases are described in PCT publication WO 2005/018579, incorporated herein by reference. Formate may be provided in the form of a salt, typically an alkali or ammonium salt (for example, $HCO_2Na$, $KHCO_2NH_4$, and the like), in the form of formic acid, typically aqueous formic acid, or mixtures thereof. A base or buffer may be used to provide the desired pH.

In some embodiments, the cofactor regenerating system comprises a secondary alcohol dehydrogenase, which is an $NAD^+$ or $NADP^+$-dependent enzyme that catalyzes the conversion of a secondary alcohol and $NAD^+$ or $NADP^+$ to a ketone and NADH or NADPH, respectively. Secondary alcohol dehydrogenases suitable for use as cofactor regenerating system include naturally occurring and non-naturally occurring ketoreductases. Naturally occurring secondary alcohol dehydrogenases include known alcohol dehydrogenases from, by way of example and not limitation, *Thermoanerobium brockii, Rhodococcus erythropolis, Lactobacillus kefir*, and *Lactobacillus brevis*, and non-naturally occurring secondary alcohol dehydrogenases include engineered alcohol dehydrogenases derived therefrom. In some embodiments, non-naturally occurring ketoreductases engineered for thermo- and solvent stability can be used. Such ketoreductases are described in the present application and the patent publications US 20080318295A1; US 20090093031A1; US 20090155863A1; US 20090162909A1; US 20090191605A1; US 20100055751A1; WO/2010/025238A2; WO/2010/025287A2; and US 20100062499A1; each of which are incorporated by reference herein.

As will be apparent from this disclosure, the engineered ketoreductase polypeptides described herein are capable of converting IPA to acetone to regenerate the cofactor NADH/NADPH or NAD+/NADP+, respectively. Thus, in some embodiments of the processes for carrying out the conversion of compound (2), or structural analogs thereof, to compound (1), or its corresponding structural analogs, the ketoreductase of the cofactor regeneration system is the engineered ketoreductase polypeptides of present disclosure, and used with a secondary alcohol as a reductant to recycle the NADPH or NADH cofactor in the reaction mixture.

Suitable secondary alcohols useful in cofactor regenerating systems include lower secondary alkanols and aryl-alkyl carbinols. Exemplary lower secondary alcohols include, but are not limited to, isopropanol, 2-butanol, 3-methyl-2-butanol, 2-pentanol, 3-pentanol, 3,3-dimethyl-2-butanol, and the like. In some embodiments, the secondary alcohol is isopropanol (IPA). Suitable aryl-alkyl carbinols include unsubstituted and substituted 1-arylethanols.

In some embodiments, the processes can be carried out without adding NADPH or NADH cofactor during the reaction and without any other enzyme systems present (e.g., glucose dehydrogenase, or formate dehydrogenase).

In some embodiments, the processes of the disclosure can be carried out wherein no cofactor recycling enzyme is present other than the engineered ketoreductase polypeptide. For example, the reaction conditions can comprise an IPA concentration of about 45-75% (v/v), an NADPH or NADH cofactor loading of about 0.01-0.5 g/L, and wherein no cofactor recycling enzyme is present other than the engineered ketoreductase polypeptide.

In some embodiments where the cofactor recycling system produces a volatile product, such as acetone from isopropanol, the volatile product can be removed, for example, by sparging the reaction solution with a non-reactive gas or by applying a vacuum to lower the reaction pressure to remove the volatile product present in the gas phase. A non-reactive gas is any gas that does not react with the reaction components. Various non-reactive gases include nitrogen and noble gases (e.g., inert gases). In some embodiments, the non-reactive gas is nitrogen gas. For example, acetone formed by oxidation of isopropanol can be removed by sparging the reaction solution with nitrogen gas or applying a vacuum to the reaction solution and removing the acetone from the gas phase by an acetone trap, such as a condenser or other cold trap.

In the embodiments herein, the ketoreductase polypeptides used in the processes and any additional enzymes of the optional cofactor regeneration system may be added to the reaction mixture in the form of the purified enzymes, whole cells transformed with gene(s) encoding the enzymes, and/or cell extracts and/or lysates of such cells.

In some embodiments, the gene(s) encoding the ketoreductase polypeptides and the optional cofactor regeneration enzymes can be transformed into host cells separately or together into the same host cell for expression of the enzymes. Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste). In some embodiments, the transformed cells can be immobilized on a solid support and the conversion reactions carried by contacting the immobilized cells with the substrate compound.

Generally, the order of addition of reactants (e.g., substrate, cofactor, polypeptide, etc.) is not critical to the processes of the present disclosure. The reactants may be added together at the same time to a solvent (e.g., monophasic solvent, biphasic aqueous co-solvent system, and the like), or alternatively, some of the reactants may be added separately, and some together at different time points.

In some embodiments, the processes can be carried out using any combination of a mixture and reaction conditions disclosed above or elsewhere herein. Accordingly, in some embodiments, the processes described herein comprise the following reaction conditions: (a) engineered ketoreductase polypeptide concentration of about 1 g/L to about 10 g/L; (b) substrate compound at a loading concentration of about 50 g/L to about 200/g/L; (c) NADP(H) concentration of about 0.1 g/L to about 0.5 g/L; (d) a co-solvent solution of an aqueous buffer and about 30% to about 70% (v/v) of IPA; and (e) a temperature of 35° C. to about 60° C.

In some embodiments, the processes described herein comprise the following reaction conditions: (a) engineered ketoreductase polypeptide concentration of about 0.1 g/L to about 1 g/L; (b) substrate compound at a loading concentration of about 5 g/L to about 50 g/L; (c) NADP(H) concentration of about 0.01 g/L to about 0.1 g/L; (d) a co-solvent solution of an aqueous buffer, and about 30% to about 70% (v/v) of IPA; and (e) a temperature of about 30° C. to about 45° C.

In some embodiments, in the process for the conversion of substrate compound (2) to product compound (1), compound (2) is at a loading of about 50 g/L to about 200 g/L and the process results in at least about 91%, 92%, 93%, 94%, 95%, 96%, 97%, 98%, 99% or greater conversion of compound (2) to compound (1) in 24 h or less.

In some embodiments, in the process for the conversion of substrate compound (2) to product compound (1a) and (1c), compound (2) is at a loading of about 50 g/L to about 200 g/L and the process results in formation of compound (1a) and (1c) diastereomeric excess of at least about 91%, 92%, 93%, 94%, 95%, 96%, 97%, 98%, 99% or greater over compounds (1b) and (1d) in 24 h or less.

In some embodiments, it is also contemplated that the process comprising the biocatalytic conversion of substrate compounds to product compounds using an engineered ketoreductase polypeptide can further comprise chemical steps of product work-up, extraction, isolation, purification, and/or crystallization, each of which can be carried out under a range of conditions.

Methods, techniques, and protocols for extracting, isolating, forming a salt of, purifying, and/or crystallizing the product compounds from biocatalytic reaction mixtures produced by the above disclosed processes are known to the ordinary artisan and/or accessed through routine experimentation. Additionally, illustrative methods are provided in the Examples below.

Various features and embodiments of the disclosure are illustrated in the following representative examples, which are intended to be illustrative, and not limiting.

6. EXAMPLES

Various features and embodiments of the disclosure are illustrated in the following representative examples, which are intended to be illustrative, and not limiting.

Example 1: Wild-Type Ketoreductase Gene Acquisition and Construction of Expression Vectors The wild-type ketoreductase gene from *L. kefir* (SEQ ID NO: 1) was designed for expression in *E. coli* using standard codon optimization. (Codon-optimization software is reviewed in e.g., "OPTIMIZER: a web server for optimizing the codon usage of DNA sequences," Puigbò et al., Nucleic Acids Res. 2007 July; 35(Web Server issue): W126-31. Epub 2007 Apr. 16.). Genes were synthesized using oligonucleotides and cloned into expression vector pCK110900 (vector depicted as FIG. 3 in US Patent Application Publication 20060195947, which is hereby incorporated by reference herein) under the control of a lac promoter. The expression vector also contained the P15a origin of replication and the chloramphenicol resistance gene. Resulting plasmids were transformed into *E. coli* W3110 (fhu-) using standard methods. Polynucleotides encoding the engineered ketoreductase polypeptides were also cloned into vector pCK110900 for expression in *E. coli* W3110.

The polynucleotide (SEQ ID NO:3) encoding the engineered ketoreductase polypeptide of SEQ ID NO: 4 was obtained by directed evolution of a codon-optimized gene encoding the wild-type ketoreductase of *Lactobacillus kefir* (Genbank acc. No. AAP94029.1; GI: 33112056). SEQ ID NO: 4 has 11 amino acid residue differences (A94G; S96V; E145F; F147M; L153T; Y190P; L195M; V196L; L199Y; I226V; and Y249W) relative to the naturally occurring ketoreductase of SEQ ID NO:2. The polypeptide of SEQ ID NO: 4 was found to convert compound (2) to compound (1a) and (1c) in a diastereomeric ratio about 25 over compound (1b) and (1d) under SFP reaction conditions (Table 2B) and >100 under DSP reaction conditions (Table 2C) but with low enzymatic activity. The polynucleotide of SEQ ID NO: 3 was used as the starting backbone for subsequent rounds of evolution to generate engineered ketoreductase with improved properties. Multiple rounds of directed evolution of the gene encoding SEQ ID NO: 4 (i.e., SEQ ID NO: 3) were carried out. Each round used the gene encoding the most improved engineered polypeptide from each round as the parent "backbone" sequence for the subsequent round of evolution. The resulting engineered ketoreductase polypeptide sequences and specific mutations and relative activities are listed in Table 2A, 2B and 2C.

Example 2: Production of Engineered Ketoreductases

The engineered ketoreductase polypeptides were produced in *E. coli* W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic process disclosed herein.

Fermentation for Shake Flask Powders.

A single microbial colony of *E. coli* containing a plasmid encoding an engineered ketoreductase of interest is inoculated into 50 mL Luria Bertani broth containing 30 µg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM MgSO$_4$) containing 30 µg/ml chloramphenicol, in a 1 liter flask to an optical density at 600 nm (OD600) of 0.2 and allowed to grow at 30° C. Expression of the ketoreductase gene is induced by addition of isopropyl β-D-thiogalactoside ("IPTG") to a final concentration of 1 mM when the OD600 of the culture is 0.6 to 0.8. Incubation is then continued overnight (at least 16 hours). Cells are harvested by centrifugation (5000 rpm, 15 min, 4° C.) and the supernatant discarded.

Production of Ketoreductase Shake-Flask Powders:

The cell pellet is resuspended with an equal volume of cold (4° C.) 100 mM phosphate buffer, pH 9.0 (optionally including 2 mM $MgSO_4$), and harvested by centrifugation as above. The washed cells are resuspended in two volumes of the cold phosphate buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude ketoreductase polypeptide. Alternatively, the cell pellet (before or after washing) can be stored at 4° C. or −80° C.

Fermentation for Production Downstream Process (DSP) Powders.

Larger-scale (~100-120 g) fermentation of the engineered ketoreductases for production of DSP powders can be carried out as a short batch followed by a fed batch process according to standard bioprocess methods. Briefly, ketoreductase expression is induced by addition of IPTG to a final concentration of 1 mM. Following fermentation, the cells are harvested and resuspended in 100 mM triethanolamine-$H_2SO_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

High-Throughput Growth & Expression.

Cells were picked and grown using standard KRED protocol for W3110 with direct induction: (1) Master growth—single colonies were picked from agar Q-trays by Q-bot and grown overnight in LB media containing 1% glucose and 30 µg/mL chloramphenicol (CAM), 30° C., 200 rpm, 85% humidity. (2) Subculture—20 µL of overnight growth were transferred to a deep well plate containing 380 µL 2×YT growth media containing 30 µg/mL CAM, 1 mM IPTG, 1 mM $MgSO_4$, and incubated for ~18 h at 30° C., 200 rpm, 85% humidity. Subculture TB media was made up of TB media (380 µL/well), 30 µg/mL CAM, 1 mM $MgSO_4$, and 1 mM IPTG. Cell cultures were centrifuged at 4000 rpm, 4° C. for 10 min., and the media discarded. Cell pellets were resuspended in 200-400 µL lysis buffer (0.1 M triethanolamine (TEA) buffer, pH 9.0, containing 1 mM $MgSO_4$, 400 µg/mL PMBS and 500 µg/mL Lysozyme).

Example 3: Ketoreductase Activity Assays

HTP Screening Assay.

Standard HTP reaction assays were carried out on 200 µL reaction volume scales in 96-wells deep well plates (reaction assay blocks). The reaction mixtures in each well typically consisted of: 20 g/L or 50 g/L compound (2); 0.05 g/L NADP+; 30% or 50% isopropyl alcohol (IPA); and 10 µL, 20 µL or 60 µL of clear lysates, as further specified in Table 2A.

Reaction Conditions A, B, D, E and G:

Reaction condition G was carried out by adding 2.5 ml of isopropyl alcohol to 500 mg compound (2) in a 20 mL vial followed by 2 mL of 0.2 M borate, pH 10.0, containing 1 mM $MgSO_4$. The resulting mixture was heated to the reaction temperature with stirring for about 15 min. A stock solution of 10 g/L enzyme and 1 g/L of NADP was prepared fresh in 0.2 M borate, pH 10, containing 1 mM $MgSO_4$. The stock solution (500 µL) was added to the reaction mixture to initiate the reaction. The vial was kept tightly closed and the reaction allowed to proceed with stirring (1200 rpm) at the desired temperature. To follow the course of the reaction, 5 µL samples were taken and diluted into 730 mL of acetonitrile (MeCN). After mixing vigorously, the suspension was centrifuged briefly to separate insoluble particles. A sample of the clear supernatant was analyzed by HPLC using the conditions described below. The reagents were adjusted for each of the assay conditions A, B, D, E, and G as specified in Tables 2B and 2C.

Reaction Conditions C and F:

A premix assay solution was prepared by adding 22.5 mL isopropyl alcohol to 33 mL of 0.2 M boric acid, pH 9, containing 1 mM $MgSO_4$. The pH of the premix solution was adjusted to 10.2 with concentrated HCl. For each experiment, 3.7 mL of freshly prepared stock solution was placed in a 20 mL screw cap glass vial, tightly closed, and heated to 35° C. with stirring (1200 rpm). After 15 min, 250 µL of a 100 g/L stock solution of the enzyme powder in 0.2 M borate, pH 9, and 50 µL of a 10 g/L NADP stock solution in sterile water were added to each vial at 35° C. with stirring (1200 rpm) Immediately after addition of the enzyme and NADP, 1 mL of a 200 g/L stock solution of compound (2) in isopropyl alcohol was added to initiate the reaction. The vial was tightly closed and the reaction allowed to proceed with stirring (1200 rpm) at 35° C. To follow the course of the reaction, 15 µL samples were taken and diluted into 730 µL of acetonitrile (MeCN). After mixing vigorously, the suspension was centrifuged briefly to remove insoluble particles. A sample of the clear supernatant was analyzed by HPLC HPLC Analysis:

Samples were analyzed by reverse phase HPLC as follows.

| Column: | Chiralpak IC (4.6 × 150 mm, 5 µm) |
|---|---|
| Temperature: | 25° C. |
| Flow rate | 1 mL/min |
| Mobile Phase: | Isocratic |
| | 60% Solvent A: 2 mM Ammonium Formate, pH 3.5 with formic acid; |
| | 40% Solvent B: Acetonitrile |
| Run time | 15 min |
| Detection | 210 nm |

Substrate and product compounds have the following retention times:

| Compound (1c)/Compound (1d) | 4.8 min |
|---|---|
| Compound (1a) | 5.6 min |
| Compound (1b) | 8.1 min |
| Substrate compounds (2a), (2b), (2c), and (2d) | 10 min and 12 min |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polynucleotide encoding a ketoreductase polypeptide capable of converting substrate compound (2), tert-butyl(1-oxo-1-phenylhex-5-yn-2-yl)carbamate, to product compound (1), tert-butyl(1-hydroxy-1-phenylhex-5-yn-2-yl)carbamate,

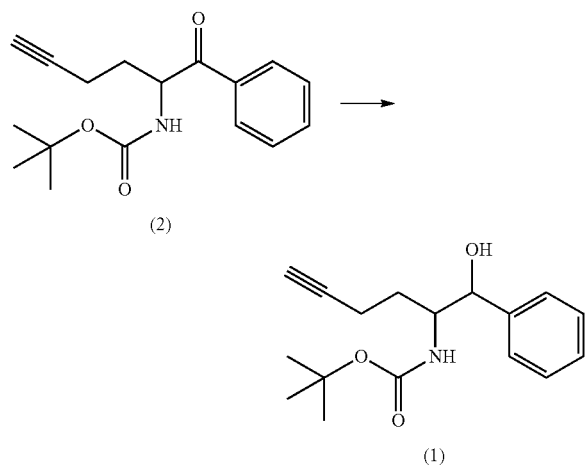

wherein the ketoreductase polypeptide comprises an amino acid sequence having at least 80% sequence identity to SEQ ID NO:4 and comprises a substitution at one or more positions selected from 40, 96, 145, 195, 199, or position 206, with the proviso that when X206 is F, the sequence further comprises one or more residue differences as compared to SEQ ID NO:4 selected from: X7S; X17M; X17Q; X17R; X23V; X27L; X29G; X60I; X64V; X71P; X87L; X94A; X94P; X94S; X95M; X96L; X96Y; X105G; X113I; X122A; X127R; X131S; X144V; X145L; X147I; X147L; X147Q; X150Y; X152G; X153G; X157C; X173L; X195A; X195G; X196M; X198S; X199H; X208R; X216R; X221S; X243S; X245I; X249F; X249G; and X249Y.

2. The engineered polynucleotide encoding the engineered ketoreductase polypeptide of claim 1, wherein the amino acid sequence of said ketoreductase polypeptide comprises at least one substitution selected from X40R, V96L, V96Y, F145L, M195A, M195G, Y199H, M206F, and M206L, and one or more residue differences as compared to SEQ ID NO:4 selected from: X7S; X17M; X17Q; X17R; X23V; X27L; X29G; X60I; X64V; X71P; X87L; X94A; X94P; X94S; X95M; X105G; X113I; X122A; X127R; X131S; X144V; X145L; X147I; X147L; X147Q; X150Y; X152G; X153G; X157C; X173L; X196M; X198S; X208R; X216R; X221S; X243S; X245I; X249F; X249G; and X249Y.

3. The engineered polynucleotide encoding the engineered ketoreductase polypeptide of claim 1, wherein the amino acid sequence of said ketoreductase polypeptide comprises X40R or X206L or F, and at least one or more residue differences as compared to SEQ ID NO:4 selected from: X17Q/R/M; X64V; X94P; X96L/Y; X144V; X147Q/I/L; X157C; X195A/G; X196M; and X199H.

4. The engineered polynucleotide encoding the engineered ketoreductase polypeptide of claim 1, wherein the ketoreductase polypeptide is capable of converting the substrate compound (2) to the product compound (1) with at least 10 fold the activity of the reference polypeptide of SEQ ID NO:4, wherein the amino acid sequence comprises the substitution X40R or X206L or F, and one or more residue differences as compared to SEQ ID NO:4 selected from: X60I; X71P; X94P; X94A; X95M; X96L; X96Y; X127R; X144V; X145I; X150Y; X152G; X153G; X157C; X195A; X195G; X196M; X198S; X199H; X216R, X245I, X245F; X249Y; and X249F.

5. The engineered polynucleotide encoding the engineered ketoreductase polypeptide of claim 1, wherein the ketoreductase polypeptide has increased thermal stability as compared to the reference polypeptide of SEQ ID NO:4 or 32, wherein the amino acid sequence comprises the features X40R or X206L or F, and one or more residue differences as compared to SEQ ID NO:4 selected from: X17Q; X17R; X17W; X64V; X71P; X87L; X94S; X94P; X147Q; X147I; X147L; X157C, X198S; X249Y; and X249F.

6. The engineered polynucleotide encoding the engineered ketoreductase polypeptide of claim 1, wherein the ketoreductase polypeptide is capable of forming product syn-tert-butyl(1-hydroxy-1-phenylhex-5-yn-2-yl)carbamate compounds (1a) and (1c)

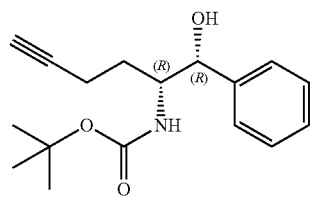
(1a)

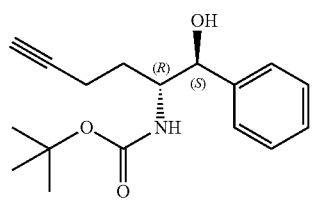
(1b)

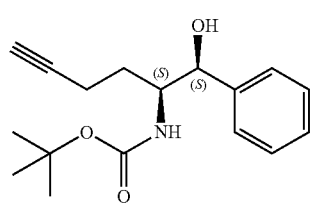
(1c)

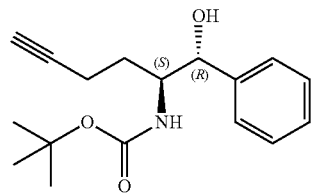
(1d)

in diastereomeric excess of anti-tert-butyl(1-hydroxy-1-phenylhex-5-yn-2-yl)carbamate compounds (1b) and (1d).

7. The engineered polynucleotide encoding the engineered ketoreductase polypeptide of claim 6, wherein the amino acid sequence of the ketoreductase polypeptide comprises or more residue differences as compared to SEQ ID NO:4 selected from: X17Q; X40R; X64V; X71P; X87L; X96L/Y; X147I; X157C; X195A/G; X196M; X199H; X206F/L; and X249F.

8. The engineered polynucleotide encoding the engineered ketoreductase polypeptide of claim 7, wherein said ketoreductase polypeptide is capable of forming product compounds (1a) and (1c) in a diastereomeric ratio of at least 50 over compounds (1b) and (1d).

9. An expression vector comprising the engineered polynucleotide of claim 1.

10. The expression vector of claim 9, comprising at least one control sequence.

11. The expression vector of claim 10, in which the control sequence is a promoter.

12. A host cell comprising the engineered polynucleotide of claim 1.

13. A host cell comprising the expression vector of claim 9.

14. The host cell of claim 12, wherein said host cell is *E. coli*.

15. The host cell of claim 13, wherein said host cell is *E. coli*.

16. A method of preparing the engineered polypeptide comprising culturing the host cell of claim 12, under conditions suitable for expression of the polypeptide, optionally further comprising isolating the engineered polypeptide.

17. A method of preparing the engineered polypeptide comprising culturing the host cell of claim 13, under conditions suitable for expression of the polypeptide, optionally further comprising isolating the engineered polypeptide.

18. A method of preparing the engineered polypeptide comprising culturing the host cell of claim 14, under conditions suitable for expression of the polypeptide, optionally further comprising isolating the engineered polypeptide.

19. A method of preparing the engineered polypeptide comprising culturing the host cell of claim 15, under conditions suitable for expression of the polypeptide, optionally further comprising isolating the engineered polypeptide.

* * * * *